US007994326B2

(12) United States Patent
Silverman et al.

(10) Patent No.: US 7,994,326 B2
(45) Date of Patent: *Aug. 9, 2011

(54) POTENT AND HIGHLY SELECTIVE HETEROAROMATIC INHIBITORS OF NEURONAL NITRIC OXIDE SYNTHASE

(75) Inventors: Richard B. Silverman, Northbrook, IL (US); Haitao Ji, Evanston, IL (US); Graham R. Lawton, Smithtown, NY (US)

(73) Assignee: Northwestern University, Evanston, IL (US)

( * ) Notice: Subject to any disclaimer, the term of this patent is extended or adjusted under 35 U.S.C. 154(b) by 106 days.

This patent is subject to a terminal disclaimer.

(21) Appl. No.: 11/906,283

(22) Filed: Oct. 1, 2007

(65) Prior Publication Data

US 2008/0108814 A1    May 8, 2008

Related U.S. Application Data

(63) Continuation-in-part of application No. 10/935,911, filed on Sep. 8, 2004, now Pat. No. 7,470,790.

(60) Provisional application No. 60/500,997, filed on Sep. 8, 2003, provisional application No. 60/848,245, filed on Sep. 29, 2006.

(51) Int. Cl.
- *C07D 211/68* (2006.01)
- *C07D 401/00* (2006.01)
- *A01N 43/40* (2006.01)
- *A61K 31/44* (2006.01)

(52) U.S. Cl. ............ 546/193; 546/268.4; 514/318; 514/343

(58) Field of Classification Search .......... 546/193, 546/268.4; 514/318, 343
See application file for complete search history.

(56) References Cited

U.S. PATENT DOCUMENTS

| 7,056,945 | B1 | 6/2006 | Poulos et al. | |
| 7,470,790 | B2 * | 12/2008 | Silverman et al. | 546/278.4 |
| 2003/0119751 | A1 | 6/2003 | Silverman et al. | |
| 2005/0107369 | A1 | 5/2005 | Silverman et al. | |
| 2008/0176907 | A1 * | 7/2008 | Silverman et al. | 514/343 |

FOREIGN PATENT DOCUMENTS

| WO | WO 2005/026111 A2 * | 3/2005 |
| WO | WO 2005026111 A2 * | 3/2005 |

OTHER PUBLICATIONS

Hcaplus 1999:246584.*
Hcaplus 2004:1122234.*
West, Anthony R., Solid State Chemistry and its Applications, Wiley, New York, 1988, pp. 358 & 365.*

* cited by examiner

*Primary Examiner* — Janet L Andres
*Assistant Examiner* — Heidi Reese
(74) *Attorney, Agent, or Firm* — Reinhart Boerner Van Deuren s.c.

(57) ABSTRACT

Peptidomimetic compounds as can inhibit neuronal nitric oxide synthase (nNOS) for potential treatment in neurodegenerative diseases, such as but not limited to stroke, Alzheimer's disease, Parkinson's disease, Huntington's disease.

20 Claims, 9 Drawing Sheets

*Trans* isomers:

P-1

P-2

P-3

*Cis* isomers:

P-4

P-5

*Trans* isomers:

*Cis* isomers:

*Trans* isomers

*Cis* isomers

*Cis* isomers:
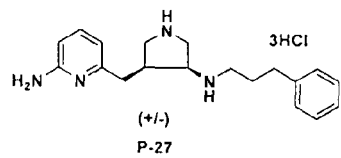
(+/-)
P-27
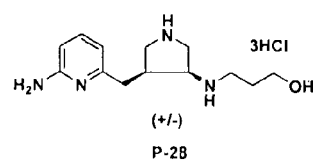
(+/-)
P-28
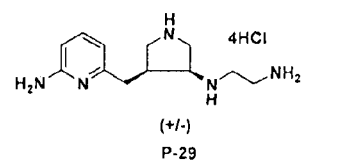
(+/-)
P-29
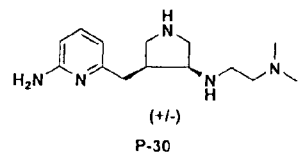
(+/-)
P-30
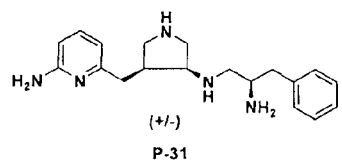
(+/-)
P-31
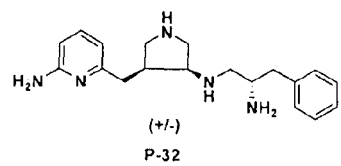
(+/-)
P-32
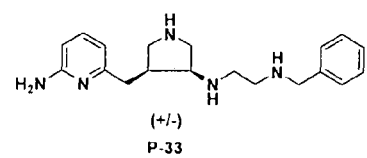
(+/-)
P-33
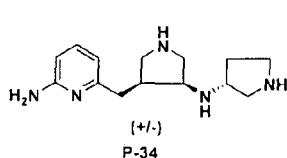
(+/-)
P-34
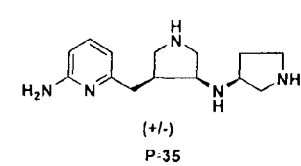
(+/-)
P-35
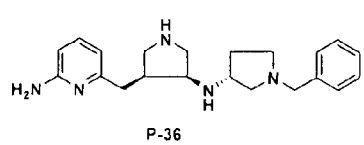
P-36
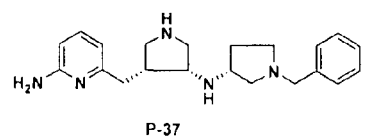
P-37
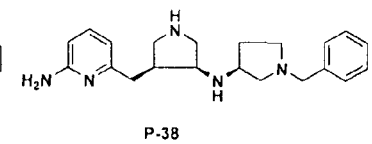
P-38
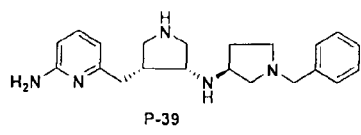
P-39
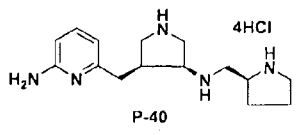
P-40
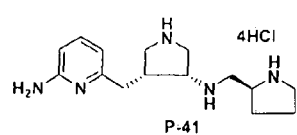
P-41
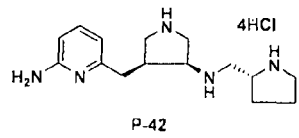
P-42
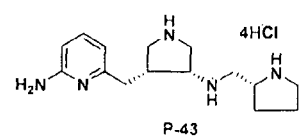
P-43
Fig. 3, con't

POTENT AND HIGHLY SELECTIVE HETEROAROMATIC INHIBITORS OF NEURONAL NITRIC OXIDE SYNTHASE

This application is a continuation-in-part of and claims priority benefit from application Ser. No. 10/935,911, filed Sep. 8, 2004 now U.S. Pat. No. 7,470,790 and prior provisional application Ser. No. 60/500,997, filed Sep. 8, 2003, and prior provisional application Ser. No. 60/848,245, filed Sep. 29, 2006, each of which is incorporated herein by reference in its entirety.

The United States Government has certain rights to this invention pursuant to grant No. GM049725 from the National Institutes of Health to Northwestern University.

BACKGROUND OF INVENTION

Nitric oxide (NO) is synthesized enzymatically from arginine in numerous tissues and cell types by a family of enzymes, collectively known as nitric oxide synthase (NOS, E.C. 1.14.13.39). Three principal isoforms of this enzyme have been isolated and characterized, each associated with different physiological functions: the immune response (inducible NOS or iNOS), smooth muscle relaxation (endothelial NOS or eNOS), and neuronal signaling (neuronal NOS or nNOS). All of these isoforms utilize NADPH, FAD, FMN, (6R)-5,6,7,8-tetrahydrobiopterin and heme as cofactors.

Overproduction of NO has been a factor in numerous disease states. NO overproduction by nNOS has been implicated in strokes, migraine headaches, Parkinson's disease, Alzheimer's disease, and with tolerance to and dependence on morphine. iNOS-mediated overproduction of NO has been associated with development of colitis, tissue damage and inflammation, and rheumatoid arthritis.

Animal studies and early clinical trials suggest that NOS inhibitors could be therapeutic in many of these disorders; however, because of the importance of nitric oxide to physiological functioning, potent as well as isoform-selective inhibitors are essential. nNOS inhibition has been targeted for treatment of strokes and Parkinson's disease, and iNOS inhibition for the treatment of septic shock and arthritis. Although there may be pathologies associated with overactivity of eNOS, blood pressure homeostasis is so critical that most investigators believe that therapeutically useful NOS inhibitors should not inhibit eNOS.

Excellent inhibitory potency and selectivity for nNOS over eNOS and iNOS have been achieved with certain prior art nitroarginine dipeptide amides that have an amine-containing side chain (cpds. 1-3 in the cited reference). See Huang, H.; Martasek, P.; Roman, L. J.; Masters, B. S. S.; Silverman, R. B. $N^{\omega}$-Nitroarginine-Containing Dipeptide Amides. Potent and Highly Selective Inhibitors of Neuronal Nitric Oxide Synthase. *J. Med. Chem.* 1999, 42, 3147-53.

The most potent nNOS inhibitor among these compounds is L-Arg$^{NO2}$-L-Dbu-NH$_2$ (1) ($K_i$=130 nM), which also shows excellent selectivity over eNOS (>1500-fold) and 192-fold selectivity over iNOS. Further peptidomimetic modifications are, however, invariably necessary before such compounds can be therapeutically useful. Generally, peptides have poor bioavailability and, for that reason, are often unsuccessful as drug candidates.

SUMMARY OF INVENTION

Figure 1:
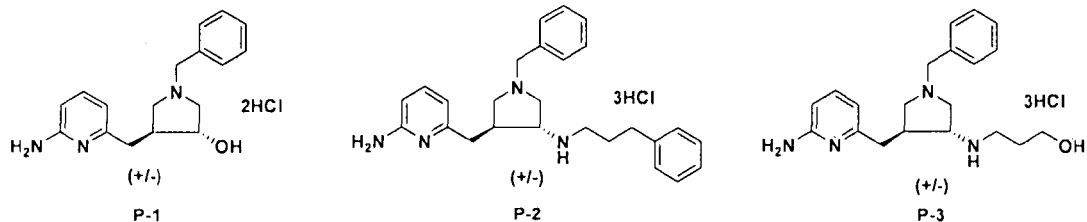
FIGS. 1-3 provide cis and trans isomers of compounds in accordance with this invention.
Figure 1:
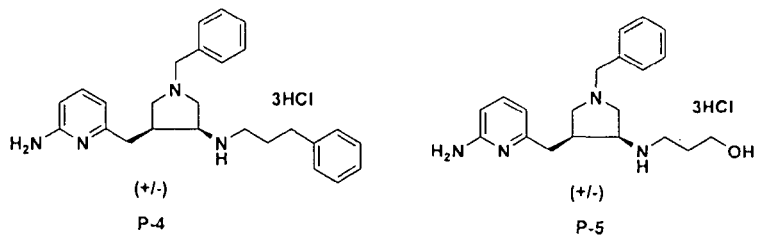

In light of the foregoing, it is an object of the present invention to provide compounds and related methods of use for the selective inhibition of neuronal nitric oxide synthase, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more small molecule and/or non-peptide compounds exhibiting selective nNOS, inhibition, over other enzyme isoforms.

It is an object of the present invention to provide one or more conformationally-constrained compounds for selective NOS inhibition.

It can also be an object of this invention to provide such non-peptide, conformationally-constrained compounds for in vitro use and study under conditions promoting nitric oxide production, indicative of one or more mammalian disease states.

Alternatively, it is an object of the present invention to provide a molecular structure or such compounds enabling in vivo treatment of such disease states.

Other objectives, features, benefits and advantages of the present invention will be apparent from this summary and its descriptions of certain embodiments of such compounds, and will be readily apparent to those skilled in the art having knowledge of the synthetic techniques described therewith. Such objectives, features, benefits and advantages will be apparent from the above as taken into conjunction with the accompanying examples, data, figures and all reasonable inferences to be drawn therefrom.

Crystal structures of the oxygenase domain of the three NOS isoforms were previously determined. A new de novo molecular design method was then developed to design the nNOS inhibitors of this invention. Residues in the active site of nNOS considered important for ligand binding were analyzed by the Multiple Copy Simultaneous Search (MCSS) method. The structural differences in the active site among the three NOS isoforms were also analyzed by the GRID/CPCA method. Then, the molecules were constructed by the LUDI library design and LUDI fragment connection. The suitable LUDI fragment library was constructed according to the results of GRID and MCSS analysis. The designed molecules were then docked into the active site using the commercially-available AutoDock 3.0 program. The binding scores were evaluated by the Cscore program. Finally, a property-based drug design strategy was used to evaluate the ADME effect of the molecules. If the binding score and/or property score of the molecules did not meet the requirements, the molecule was re-constructed, re-docked and re-scored, until the new molecules gave satisfactory results.

Considerations in the design of the present selective nNOS inhibitors include, whether: (1) the molecules interact with the key residues that have been identified in nNOS; (2) the molecules interact with residues that give selectivity for both nNOS/eNOS and for nNOS/iNOS; (3) the molecules are conformationally-constrained, especially, in a constrained conformation that matches the nNOS-isoform selectivity; (4) the molecules are orally absorbed and pass through the blood-brain barrier. Such an approach provided two advantages: (a) A strategy for the production of new molecules and lead compounds; (b) Results of active site analysis can be easily merged into a process for new molecular design.

Accordingly, the present invention relates, in part, to compounds of a formula.

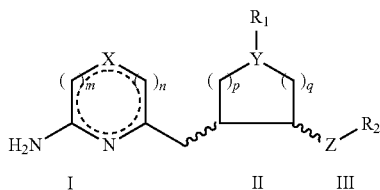

Such a compound can be considered as in the context of substructures I, II and III, as shown. Substructure I comprises an amino-substituted nitrogen-containing aromatic ring, where X can be CH, N, O, or S; and m, and n can be 0 or 1, provided at least one of m and n is 1. Substructure II comprises a five- or six-membered ring, where Y can be N or CH; and p and q can be 1 or 2, provided at least one of p and q is 1 and both p and q are not concurrently 2. Further, $R_1$ can be H, alkyl, amino, hydroxy, or a substituted alkyl (e.g., but not limited to aminoalkyl or hydroxyalkyl) moiety. Substructure III can be an alkyl, substituted alkyl, alkylhydroxy (Z═O), substituted alkylhydroxy (Z═O), alkylamine (Z═NH) or a substituted alkylamine (Z═NH) moiety (e.g., but not limited to linear, cyclic alkylamine).

The structure of such a compound is limited only by choice of starting material or reagent and enroute to substructures I, II and/or III. Likewise, the present compounds are without stereochemical limitation. As illustrated below, such compounds and/or their intermediates are available as racemic mixtures from which isomers can be resolved or are diastereomers, from which cis and/or trans isomers can be separated. Further, it will be understood by those skilled in the art that the compounds of this invention can comprise an acid salt of any such compound. Without limitation, certain embodiments can be partially or fully protonated, comprising a primary, secondary and/or tertiary amine, whereby the counter ion(s) is a conjugate base of a protic acid.

Without regard to compound charge or stereochemistry, in certain embodiments, m and n are 1 and X is CH, such that substructure I can comprise an amino-substituted pyridinyl moiety. Regardless, in certain embodiments, Y is N, p is 1 or 2, and Z is NH, such that substructure II comprises, respectively, an amino-substituted pyrrolidinyl or piperazinyl moiety. Alternatively, Y can be CH and substructure II can comprise a cyclopentyl or cyclohexyl moiety, where p and q can be 1 or 2, provided at least one of p and q is 1. Regardless, $R_1$ can be as described above or as illustrated elsewhere herein. $R_2$, in certain embodiments, can comprise an aminoalkyl moiety pendant to the aforementioned amino (Z is NH) substituent. Accordingly, $R_2$ can comprise any primary, secondary, or tertiary, linear or cyclic aminoalkyl group.

Alternatively, this invention can be directed to compounds of a formula.

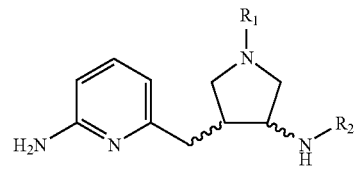

Without limitation, certain embodiments are as provided above in conjunction with the foregoing discussion regarding $R_1$ and $R_2$. Likewise, such compounds are not restricted by charge or stereochemistry.

In part, the present invention can also provide a method of inhibiting neuronal nitric oxide synthase, such a method comprises contacting a neuronal nitric oxide synthase with an effective amount of any of the present compounds, including but not limited to those illustrated by the following examples, referenced figures and/or accompanying synthetic schemes. More specifically, as also supported herein, the present invention can provide a method for selective inhibition of neuronal nitric oxide synthase. Such a method can comprise: (1) providing a compound of this invention; and (2) contacting a nitric oxide synthase with such a compound, such contact selectively inhibiting neuronal nitric oxide synthase over inducible and endothelial isoforms.

The present invention can also relate, in part, to compounds of a formula.

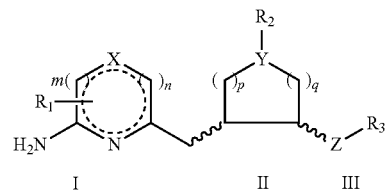

Such a compound can be considered as in the context of substructures I, II and III, as shown. Substructure I can comprise an amino-substituted nitrogen-containing aromatic ring, where X can be CH, N, O, or S; m and n can independently be 0, 1 or 2 and/or as described elsewhere herein, $R_1$ can be H, halogen, $CH_3$, and/or $CF_3$. Substructure II can comprise a five-, six- or seven-membered ring, where Y can be O, N, $^+NR_4$ or C, and p and q can be 1 or 2 and/or as described elsewhere herein. Further, $R_2$ and $R_4$ can independently be selected from H, alkyl, amino, hydroxy, or a substituted alkyl (e.g., but not limited to aminoalkyl or hydroxyalkyl) moiety. Substructure III can comprise Z which can be selected from NH, O, NHCO, that can be substituted ($R_3$) with alkyl, substituted alkyl, hydroxyalkyl, arylalkylaminoalkyl, arylalkyloxaalkyl, arylalkylamidoalkyl (where the amido group is either NHCO or CONH), aminoalkyl, or a substituted aminoalkyl moiety (e.g., but not limited to linear, cyclic alkylamine).

The structure of such a compound is limited only by choice of starting material or reagent and enroute to substructures I, II and/or III. Likewise, the present compounds are without stereochemical limitation. As illustrated below, such compounds and/or their intermediates are available as racemic mixtures from which isomers can be resolved or are diastereomers, from which cis and/or trans isomers can be separated. Further, it will be understood by those skilled in the art that the compounds of this invention can comprise an acid salt of any such compound. Without limitation, certain embodiments can be partially or fully protonated, comprising a primary, secondary and/or tertiary amine, whereby the counter ion(s) is a conjugate base of a protic acid.

Without regard to compound charge or stereochemistry, in certain embodiments, m and n can be 1 and X can be CH, such that substructure I can comprise an amino-substituted pyridinyl moiety, as shown below. $R_1$ can be H, $CH_3$, halogen, and/or $CF_3$. Regardless, in certain embodiments, Y can be N or $^+NR_4$, p and q can be 1 or 2, and Z can be N or O, such that substructure II can comprise, respectively, an amino-substituted piperidinyl or piperazinyl moiety. Alternatively, Y can be CH and substructure II can comprise a cyclopentyl or cyclohexyl moiety, where p and q can be 1 or 2. Regardless, $R_2$ can be as described above or as illustrated elsewhere herein. $R_3$, in certain embodiments, can comprise an aminoalkyl moiety pendant to the aforementioned amino (Z is N or O) substituent. Accordingly, $R_3$ can comprise any primary, secondary, or tertiary, linear or cyclic aminoalkyl group.

In part, this invention can be directed to a neuronal nitric oxide synthase inhibitor compound of a formula

Figure 10:
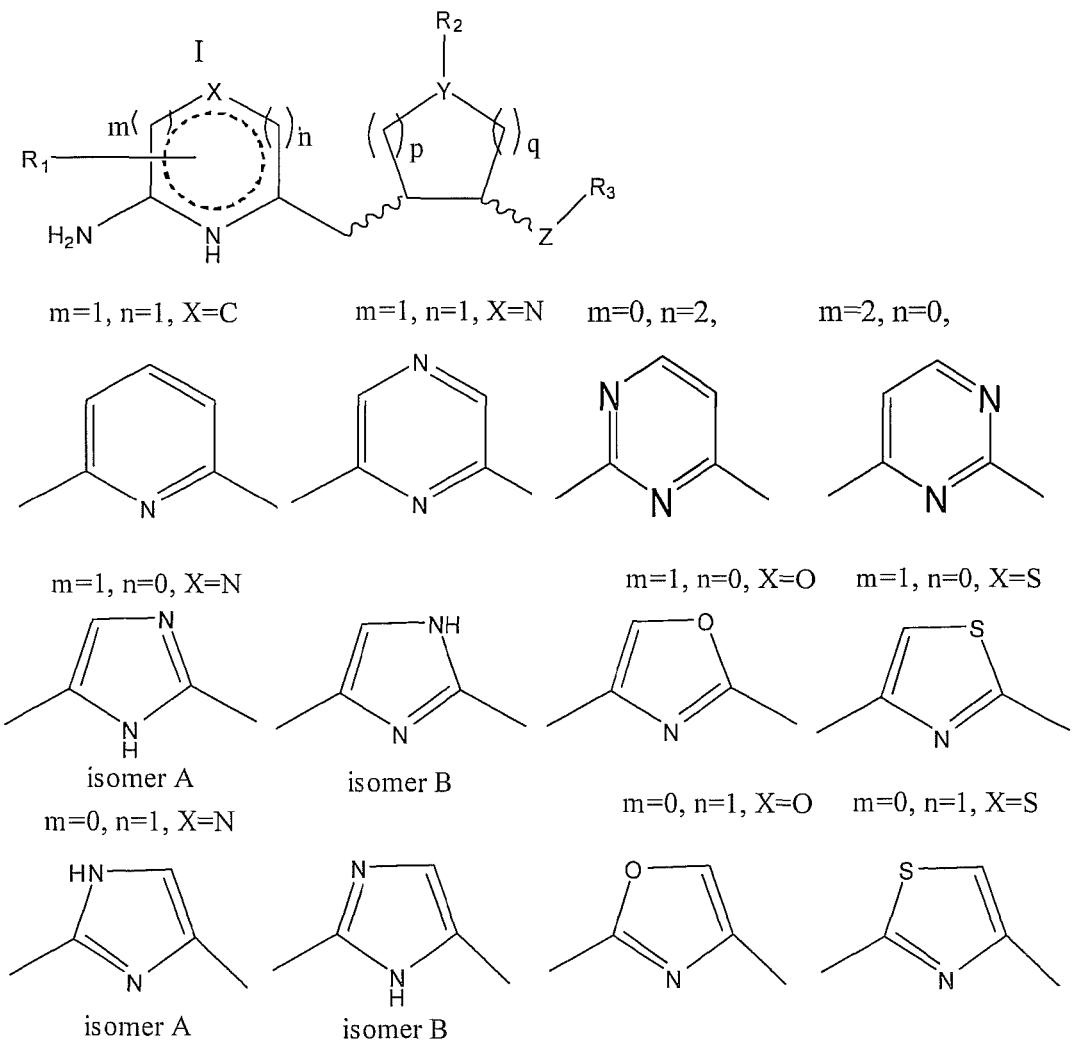
FIG. 10 shows several non-limiting, representative structural formulae of substructure I, below.

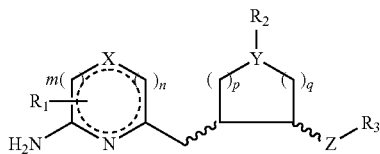

wherein X can be selected from CR, N, O and S, and R can be selected from H, methyl and substituted methyl (e.g., fluoro-substituted, etc.) moieties; m and n can be integers independently selected from 0, 1 and 2, can be described as $0 < (m+n) \leq 2$ such that substructure I can comprise a 5- or 6-member ring and the heterocyclic ring can be aromatic. Regardless, Y can be selected from CH, O and N; p and q can be integers independently selected from 0, 1 and 2, and can be described as $1 < (p+q) \leq 4$ such that substructure II can comprise a 5-, 6- or 7-member ring; and Z can be selected from NH, O, $^+NR_4$ and NHC(O). Notwithstanding identity of X, Y and Z, $R_1$ can be selected from H, alkyl, substituted alkyl (e.g., fluoro-, etc.) and halogen moieties; $R_2$ can be selected from H, alkyl, amino, hydroxyl, and substituted alkyl moieties; $R_3$ can be selected from alkyl, substituted alkyl, hydroxyalkyl, substituted hydroxyalkyl, arylalkylaminoalkyl, substituted arylalkylaminoalkyl, arylalkyloxaalkyl substituted arylalkyloxaalkyl, arylalkylamidoalkyl, substituted arylalkylamidoalkyl, aminoalkyl, and substituted aminoalkyl moieties; and $R_4$ can be H. Such a compound can be cis or trans with respect to the stereocenters and present as a salt, hydrate and/or solvate thereof. With reference to substructure I, above, several non-limiting embodiments of the present compounds can comprise aromatic substructures of the sort shown in FIG. 10.

In certain embodiments, X can be CH, and m and n can be 1. In a subset of such embodiments, Y can be N or $^+NR_4$, and p and q can be 1. In turn, as a subset thereof, Z can be NH or O, and $R_3$ can comprise a moiety selected from aminoalkyl and substituted aminoalkyl moieties. Regardless, such an $R_3$ moiety can comprise one or more primary, secondary, tertiary, linear or cyclic amino groups; and, independently, $R_2$ can be either H or an aminoalkyl moiety. With any such embodiment, where Y is $^+NR_4$, $R_4$ can be H.

In certain other embodiments, X can be CR and R can be methyl. In a subset of such embodiments, Y can be N or $^+NR_4$, and p and q can be 1. In turn, as a subset thereof, Z can be NH or O; $R_2$ can be selected from H, aminoalkyl and substituted aminoalkyl moieties; and $R_3$ can be selected from aminoalkyl, substituted aminoalkyl, arylalkylaminoalkyl and substituted arylalkylaminoalkyl moieties. Likewise, any combination of $R_2$ and $R_3$ moieties can be present where Y can be CH, and p and q can be 1, and where Z can be NH or O.

In part, this invention can also be directed to a neuronal nitric oxide synthase inhibitor compound of a formula

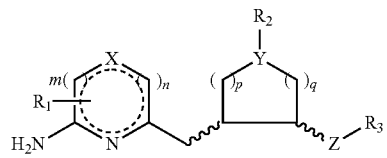

wherein X can be CR and R can be selected from H, methyl, and substituted methyl (e.g., fluoro-, etc.) moieties; m and n can be integers independently selected from 0-2 and/or as described above, and at least one of m and n can be 1, and the heterocyclic ring can be aromatic. Regardless, Y can be selected from CH, $^+NR_4$ and N; p and q can be integers independently selected from 0, 1 and 2 and/or as described above; and Z can be selected from NH, O and NHC(O). Notwithstanding, identity of X, Y, and Z, $R_1$ can be selected from H, alkyl, substituted alkyl (e.g., fluoro-, etc.) and halogen moieties; $R_2$ can be selected from H, alkyl, substituted alkyl, aminoalkyl, substituted aminoalkyl, hydroxyalkyl, and substituted hydroxyalkyl moieties; $R_3$ can be selected from alkyl, substituted alkyl, hydroxyalkyl, substituted hydroxyalkyl, aminoalkyl, substituted aminoalkyl, arylalkylaminoalkyl and substituted arylalkylaminoalkyl moieties; and $R_4$ can be H. Such a compound can be cis or trans with respect to the stereocenters and present as a salt, hydrate and/or solvate thereof. Reference is again made to FIG. 10, for several non-limiting substructural formulae.

In certain embodiments, $R_1$ can be selected from various alkyl moieties, and m and n can be 1. In a subset of such embodiments, $R_2$ can be H, and Z can be selected from NH and O with $R_3$ selected from phenylethylaminoalkyl and substituted phenylethylaminoalkyl moieties. In certain other embodiments, $R_1$ can be selected from H and methyl moieties, and $R_2$, $R_3$, Z and Y can independently vary as described elsewhere herein.

In part, this invention can also be directed to a neuronal nitric oxide synthase inhibitor compound of a formula

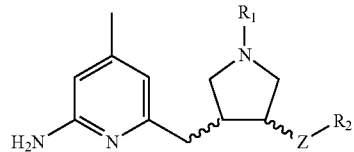

wherein $R_1$ can be selected from H, alkyl, substituted alkyl, aminoalkyl, substituted aminoalkyl, hydroxyalkyl, and substituted hydroxyalkyl moieties; Z can be selected from NH, O and NHC(O); and $R_2$ can be selected from alkyl, substituted alkyl, hydroxyalkyl, substituted hydroxyalkyl, aminoalkyl, substituted aminoalkyl, arylalkylaminoalkyl and substituted arylalkylaminoalkyl moieties. Such a compound can be cis or trans with respect to the stereocenters and present as a salt, hydrate and/or solvate thereof. In certain embodiments, $R_1$ is H, and $R_2$ can be selected from arylalkylaminoalkyl and substituted arylalkylaminoalkyl moieties, whether Z is NH, O or NHC(O).

In part, the present invention can also provide a method of inhibiting neuronal nitric oxide synthase, such a method comprises contacting a neuronal nitric oxide synthase with an effective amount of any of the present compounds, including but not limited to those illustrated by the following examples, referenced figures and/or accompanying synthetic schemes. More specifically, as also supported herein, the present invention can provide a method for selective inhibition of neuronal nitric oxide synthase. Such a method can comprise: (1) providing a compound of this invention; and (2) contacting a nitric oxide synthase with such a compound, such contact selectively inhibiting neuronal nitric oxide synthase over inducible and endothelial isoforms.

Selective inhibition of nNOS was demonstrated for representative compounds of this invention, using procedures and protocols well-known to those skilled in the art. All of the NOS isoforms used were recombinant enzymes overexpressed in *E. coli* from different sources. Nitric oxide formation from NOS was monitored by the hemoglobin capture assay as described in the literature. The apparent $IC_{50}$ values demonstrating such inhibition were obtained by measuring percent inhibition in the presence of 10 μM L-arginine with at least three concentrations of inhibitor.

Certain embodiments of this invention can comprise compounds of a non-peptide structure, but as can be considered peptidomimetic, in that they can provide a possibility to increase in vivo biological activities through certain structural modification(s). Crystal structures of nNOS, iNOS, and eNOS oxygenase domains can be employed as a basis for inhibitor design. Fragment-based structure optimization, with the assistance of computer modeling, can be used to explore nNOS inhibitory potency and selectivity during the hibitor design. Such a property-based structure optimization can be used to increase the probability of such inhibitors to pass biomembranes, in particular, without limitation, the blood-brain barrier, and/or to increase their bioavailability.

Accordingly, compounds of this invention can be used in vitro for nNOS inhibition and/or in the treatment or evaluation for treatment of various neurodegeneration, including that from stroke, Alzheimer's disease, Parkinson's disease, and Huntington's disease.

EXAMPLES OF THE INVENTION

The following non-limiting examples and data illustrate various aspects and features relating to the compounds and/or methods of the present invention, including the preparation and use of various nitric oxide synthase inhibitor compounds, as are available through the synthetic methodologies described herein. In comparison with the prior art, the present compounds and related methods provide results and data which are surprising, unexpected and contrary thereto. While the utility of this invention is illustrated through the preparation and use of several compounds, it will be understood by those skilled in the art that comparable results are obtainable with various other compounds, as are commensurate with the scope of this invention.

Examples 1-8 can be considered in conjunction with Scheme I, below.

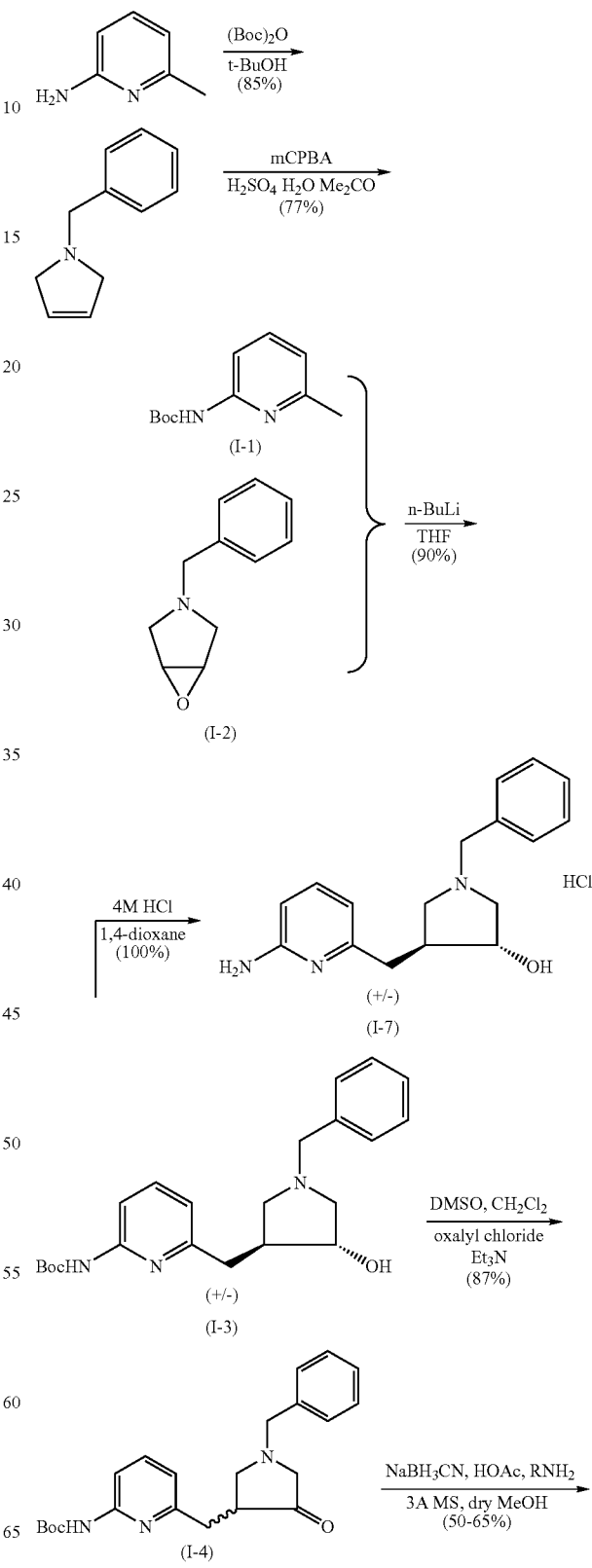

Scheme I

-continued

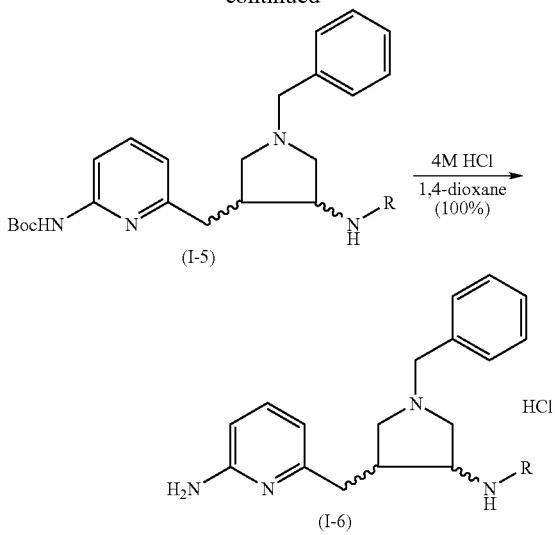

Example 1

Synthesis of (6-methyl-pyridin-2-yl)-carbamic acid tert-butyl ester (I-1)

A solution of 2-amino-6-picoline (0.025 mol) in 50 mL of melted t-butanol was treated with di-tert-butyl dicarbonate (0.0275 mol). The temperature was kept about 60° C. After the solution was stirred for 48 h, the solvent was evaporated. The residue was purified by column chromatography (silica gel, 8:2 hexanes to ethyl acetate) to obtain pure (I) in 85% yield.

Example 2

Synthesis of 3-benzyl-6-oxa-3-aza-bicyclo[3.1.0]hexane (I-2)

To an ice-cooled solution of 1-benzyl pyrroline (0.01 mol), 98% $H_2SO_4$ (0.012 mol), water (1.5 g), and acetone (10 mL) in a round bottom flask was added 77% m-CPBA (0.013 mol) with stirring, and allowed to react for about 50 h at room temperature. After completion of the reaction (TLC monitor), acetone was evaporated under reduced pressure, and the mixture was neutralized by 1M NaOH, and extracted with toluene (30 mL×3). The precipitates that appeared were filtered, and the filtrate was repeatedly washed with water (30 mL×2). After the solvent was evaporated under reduced pressure, pure product was obtained in 77% yield via column chromatography (silica gel, $CH_2Cl_2$:EtOAc:MeOH, 7.5:2.00:0.5).

Example 3

Synthesis of [6-(1-benzyl-4-hydroxy-pyrrolidin-3-ylmethyl)-pyridin-2-yl]-carbamic acid tert-butyl ester (I-3)

A solution of (6-methyl-pyridin-2-yl)-carbamic acid tert-butyl ester I-1 (0.00625 mol) in 10 mL THF was cooled in a −78° C. bath (acetone/dry ice). n-BuLi (1.6 M in hexanes, 0.0125 mol) was added during 15 min. under $N_2$. The color of solution was changed from colorless to orange. Then the cooling bath was removed. After 45 min stirring at room temperature, the color solution was changed into dark red. The solution was then returned to the −78° C. bath. 3-Benzyl-6-oxa-3-aza-bicyclo[3.1.0]hexane I-2 (0.005 mol) in 10 mL THF was added during 1 h. After 2 h, the cooling bath was removed. The solution was stirred for 2 h more at room temperature. The reaction was quenched by the addition of ice-cold water (50 ml). The mixture was extracted with $CH_2Cl_2$ (30 ml×3). The combined organic layers were washed with brine and dried over anhydrous $MgSO_4$. The solvent was removed in vacuo and the residue was purified by column chromatography (silica gel, $CH_2Cl_2$: MeOH, 9:1) (90%).

Example 4

Synthesis of [6-(1-benzyl-4-oxo-pyrrolidin-3-ylmethyl)-pyridin-2-yl]-carbamic acid tert-butyl ester (I-4)

To a solution of DMSO (0.02 mol) in 30 mL of anhydrous $CH_2Cl_2$ was added dropwise oxalyl chloride (0.015 mol). The mixture was stirred at −78° C. for 10 min. After this time a solution of [6-(1-benzyl-4-hydroxy-pyrrolidin-3-ylmethyl)-pyridin-2-yl]-carbamic acid tert-butyl ester I-3 (0.01 mol) in 10 mL of anhydrous $CH_2Cl_2$ was added dropwise at a rate to keep the reaction temperature below −60° C. Upon complete addition, the mixture was allowed to stir at −78° C. for 2 h. Then anhydrous triethylamine (0.03 mol) was added dropwise to the mixture. After complete addition, the reaction mixture was allowed to warm to room temperature. The resulting solution was partitioned between 1 M NaOH (40 ml) and the product was extracted with $CH_2Cl_2$ (30 ml×2). All organic layers were combined, washed with brine, dried over anhydrous $Na_2SO_4$, and concentrated in vacuo to yield crude product, which was purified using column chromatography (silica gel, $CH_2Cl_2$:EtOAc, 4:1) (87%).

Example 5

Synthesis of [6-(4-substituted amino-1-benzyl-pyrrolidin-3-ylmethyl)-pyridin-2-yl]-carbamic acid tert-butyl ester (I-5)

To a solution of [6-(1-benzyl-4-oxo-pyrrolidin-3-ylmethyl)-pyridin-2-yl]-carbamic acid tert-butyl ester I-4 (0.001 mol), substituted amine, such as 3-phenyl-propylamine, (0.015 mol), acetic acid (0.0015 mol), and 3 Å molecular sieves (1 g) in dry MeOH (20 mL) was added $NaBH_3CN$ (0.002 mol). Then the reaction was stirred at room temperature under $N_2$ atmosphere for 36 h. TLC monitors the completion of the reaction. The reaction mixture was then filtered, and the filtrate was concentrated in vacuo. The residue was diluted with 1M NaOH (50 mL) and extracted with $CH_2Cl_2$ (50 ml×2). The organic layers were combined, washed with brine, dried over anhydrous $MgSO_4$ and concentrated in vacuo of solvent to give crude product, which was purified by column chromatography (silica gel, hexanes:EtOAc:$Et_3N$, 3:2:0.25 for {6-[1-benzyl-4-(3-phenyl-propylamino)-pyrrolidin-3-ylmethyl]-pyridin-2-yl}-carbamic acid tert-butyl ester) (65%). The cis and trans isomers can be separated with the above eluent. The ratio of cis and trans isomers was 45:55.

Example 6

Synthesis of 6-[1-benzyl-4-(substituted amino)-pyrrolidin-3-ylmethyl]-pyridin-2-ylamine hydrochloride salt (I-6) or 4-(6-amino-pyridin-2-ylmethyl)-1-benzyl-pyrrolidin-3-ol hydrochloride salt (I-7)

[6-(4-Substituted amino-1-benzyl-pyrrolidin-3-ylmethyl)-pyridin-2-yl]-carbamic acid tert-butyl ester (0.0002 mol, I-5), such as 6-[1-benzyl-4-(3-phenyl-propylamino)-pyrrolidin-3-ylmethyl]-pyridin-2-yl}-carbamic acid tert-butyl ester, or [6-(1-benzyl-4-hydroxy-pyrrolidin-3-ylmethyl)-pyridin-2-yl]-carbamic acid tert-butyl ester I-3, was cooled by an ice-water bath under argon. A solution of 4M HCl in 1,4-dioxane was then added slowly with stirring. The ice-water bath was removed after 3 h, and the reaction mixture was stirred at room temperature overnight. After the completion of the reaction, liquids were evaporated under reduced pressure, and the residue was partitioned between water (10 mL) and ethyl acetate (10 mL). The aqueous layer was then washed with ethyl acetate (5 mL×2). After evaporation of water by high vacuum rotorvapor, the residue was dried by a lyophilizer to give the product.

Example 7

Various other compounds, including those of FIG. 1, were prepared in accordance with the synthetic route of Scheme I. All the chemical structures were confirmed by $^1$H NMR, $^{13}$CNMR, and mass spectra. All of the products are racemic mixtures.

Example 8

Without limitation, in accordance with Scheme I and compound I-6, compounds P-3 and P-5 of FIG. 1 were prepared as shown in Scheme Ia.

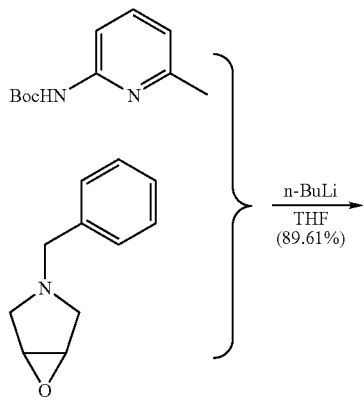

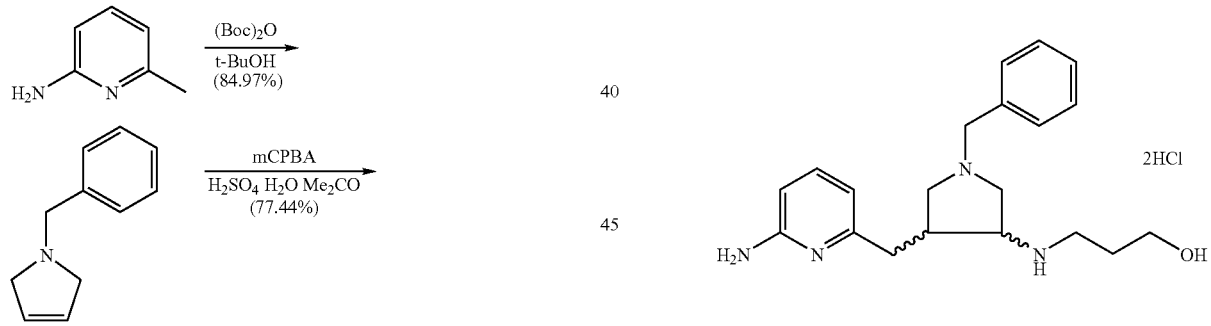

Examples 9-16 can be considered in conjunction with Scheme II, below,

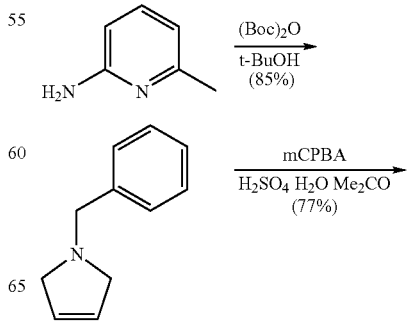

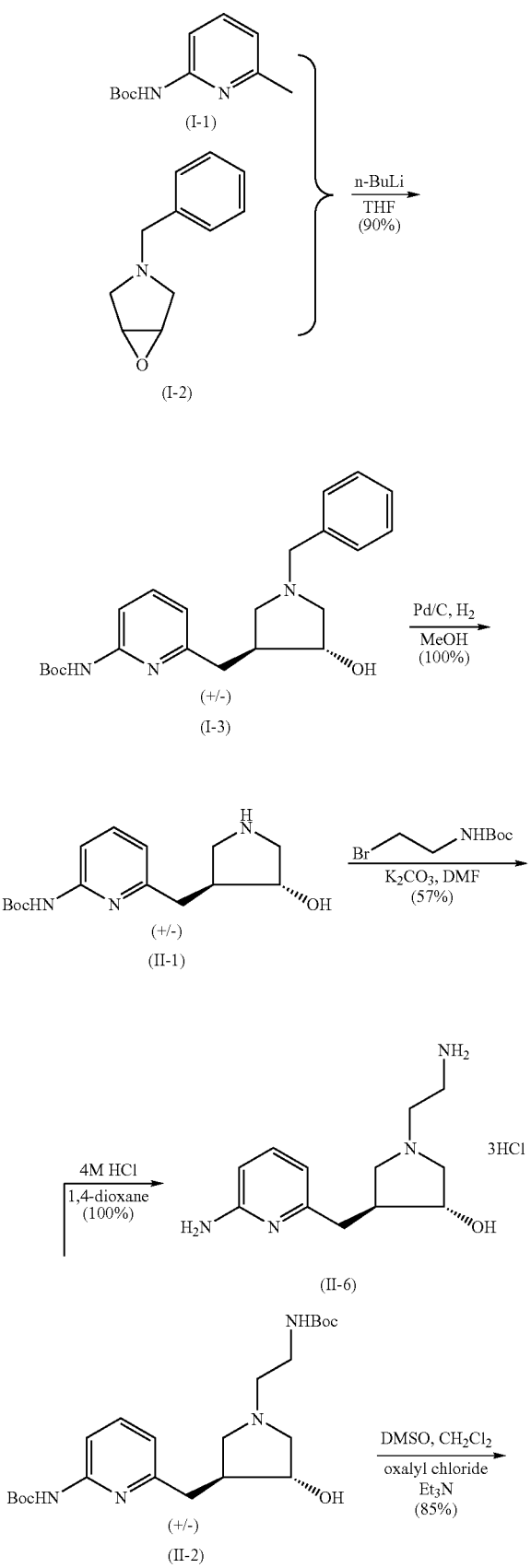
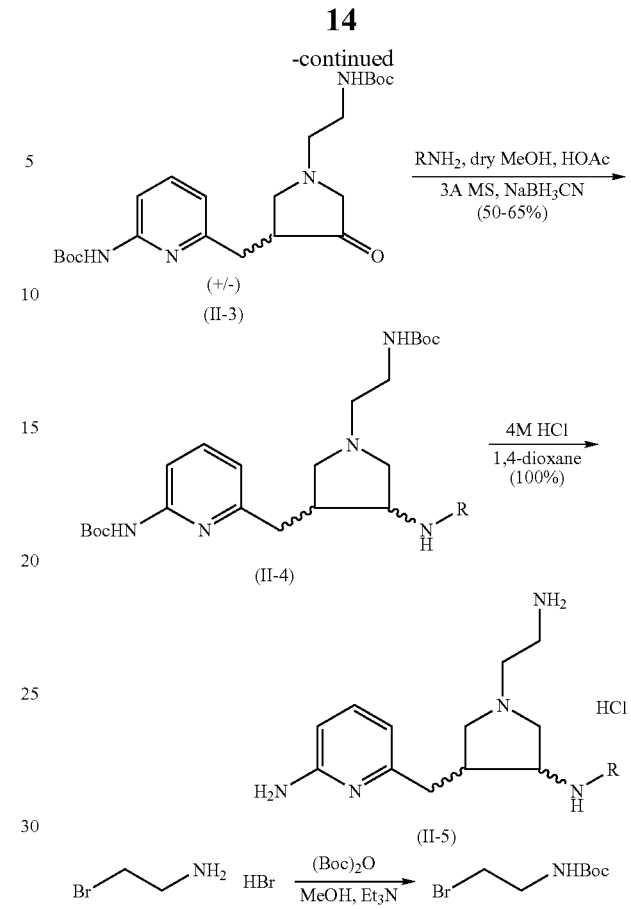

Example 9

Synthesis of [6-(4-hydroxy-pyrrolidin-3-ylmethyl)-pyridin-2-yl]-carbamic acid tert-butyl ester (II-1)

A suspension of [6-(1-benzyl-4-hydroxy-pyrrolidin-3-yl-methyl)-pyridin-2-yl]-carbamic acid tert-butyl ester I-3 (0.002 mol) and 10% Pd—C (0.7 g) in MeOH (30 mL) was stirred at 45° C. under hydrogen overnight. Then, the catalyst was removed by filtration and washed with MeOH (30 mL). The filtrate was concentrated to give II-1. Most of the product was used in the next reaction without further purification (100%). Some was purified by column chromatography (silica gel, CH₂Cl₂:MeOH:Et₃N, 6:30:0.1) to determine NMR and mass spectrum.

Example 10

Synthesis of {6-[1-(2-tert-butoxycarbonylamino-ethyl)-4-hydroxy-pyrrolidin-3-ylmethyl]-pyridin-2-yl}-carbamic acid tert-butyl ester (II-2)

A mixture of [6-(4-hydroxy-pyrrolidin-3-ylmethyl)-pyridin-2-yl]-carbamic acid tert-butyl ester II-1 (0.01 mol), (2-bromo-ethyl)-carbamic acid tert-butyl (0.012 mol), anhydrous K₂CO₃ (0.02 mol) in 50 mL anhydrous DMF was stirred at room temperature overnight. Solids were filtered off. The filtrate was evaporated under reduced pressure. The residue was partitioned between EtOAc and water. The organic layer was washed with brine, dried over anhydrous Na$_2$SO$_4$, and evaporated in vacuo. The obtained residue was purified by column chromatography (silica gel, CH$_2$Cl$_2$: MeOH, 9:1). (57%)

Example 11

The synthetic procedure for {6-[1-(2-tert-butoxycarbonylamino-ethyl)-4-oxo-pyrrolidin-3-ylmethyl]-pyridin-2-yl}-carbamic acid tert-butyl ester (II-3) is analogous to that of [6-(1-benzyl-4-oxo-pyrrolidin-3-ylmethyl)-pyridin-2-yl]-carbamic acid tert-butyl ester (I-4).

Example 12

The synthetic procedure for {6-[4-substituted amino-1-(2-tert-butoxycarbonylamino-ethyl)-pyrrolidin-3-ylmethyl]-pyridin-2-yl}-carbamic acid tert-butyl ester (II-4) is analogous to that for [6-(4-substituted amino-1-benzyl-pyrrolidin-3-ylmethyl)-pyridin-2-yl]-carbamic acid tert-butyl ester (I-5).

Example 13

The synthetic procedure for 6-[4-substituted amino-1-(2-amino-ethyl)-pyrrolidin-3-ylmethyl]-pyridin-2-ylamine hydrochloride salt (II-5) is analogous to that for 6-[1-benzyl-4-(substituted amino)-pyrrolidin-3-ylmethyl]-pyridin-2-ylamine hydrochloride salt (I-6).

Example 14

The synthetic procedure for 1-(2-amino-ethyl)-4-(6-amino-pyridin-2-ylmethyl)-pyrrolidin-3-ol hydrochloride salt (II-6) is analogous to that for 4-(6-amino-pyridin-2-ylmethyl)-1-benzyl-pyrrolidin-3-ol hydrochloride salt (I-7).

Example 15

Synthesis of (2-bromo-ethyl)-carbamic acid tert-butyl ester (II-7)

To a solution of 2-bromoethylamine hydrobromide (0.0049 mol) in MeOH (30 mL), triethylamine (7 mL) and di-tert-butyl dicarbonate (0.0098 mol) was added. The reaction mixture was stirred at 60° C. for 1 h and then at room temperature for 14 h. The reaction mixture was concentrated in vacuo, and then dissolved in CH$_2$Cl$_2$, washed successively with 1M HCl, brine, saturated NaHCO$_3$ aqueous solution and brine, dried over anhydrous MgSO$_4$ and concentrated in vacuo. The residue was purified by column chromatography (silica gel, 100% CH$_2$Cl$_2$) to give pure product as colorless oil (84%).

Example 16

Figure 2:
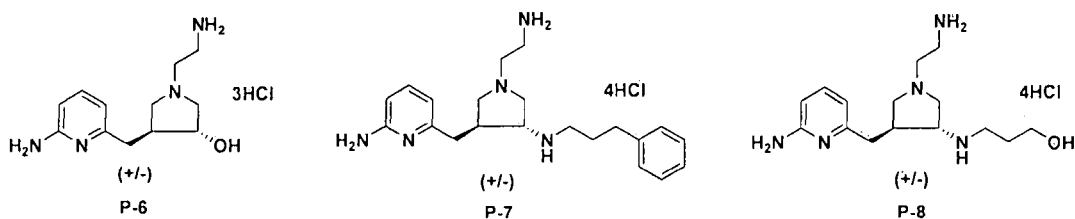
Figure 2:
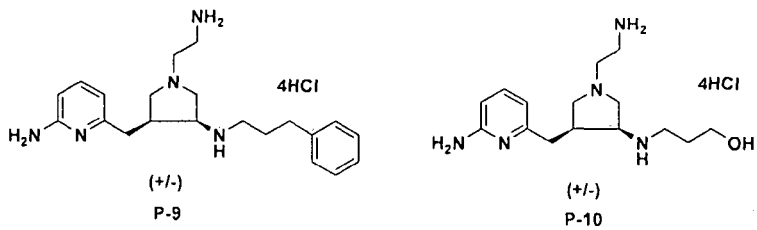

Various other compounds, including those of FIG. 2, were prepared in accordance with the synthetic route of Scheme II. All the chemical structures were confirmed by $^1$H NMR, $^{13}$CNMR, and mass spectra. All of the products are racemic mixtures.

Example 17

In accordance with Scheme II and compound II-5, compounds P-7 and P-9 of FIG. 2 were prepared as provided in Scheme IIa.

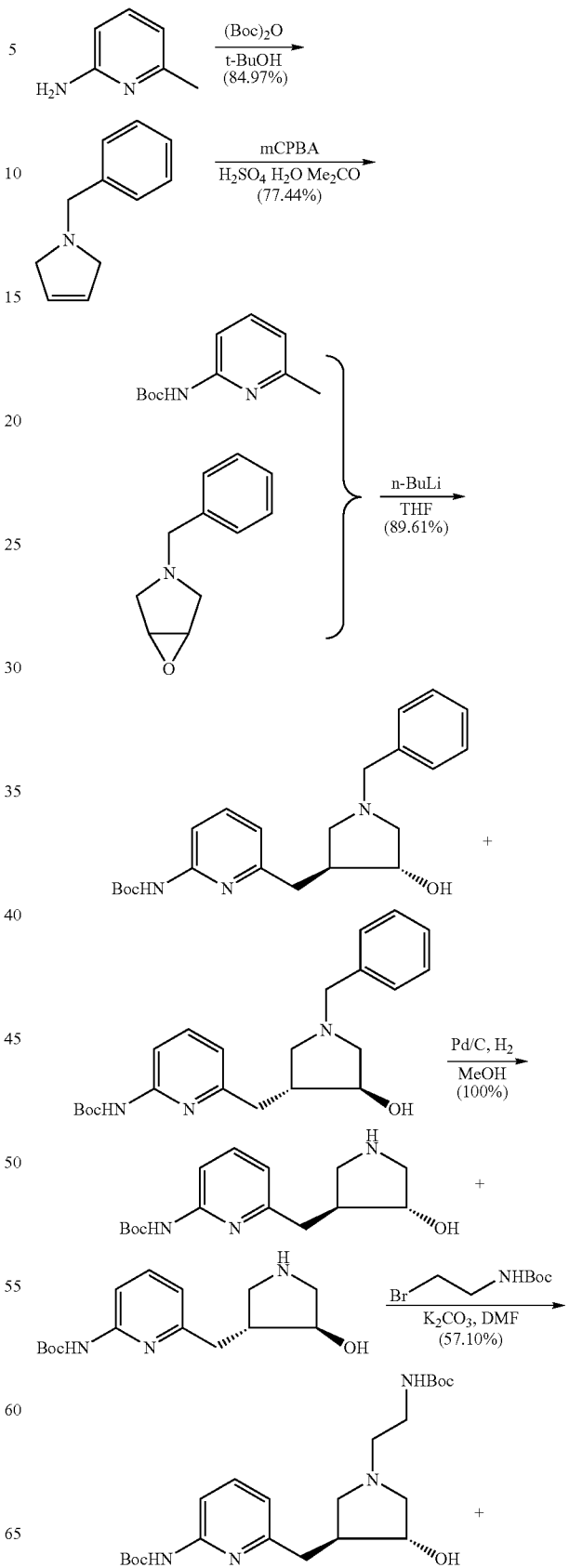

Scheme IIa

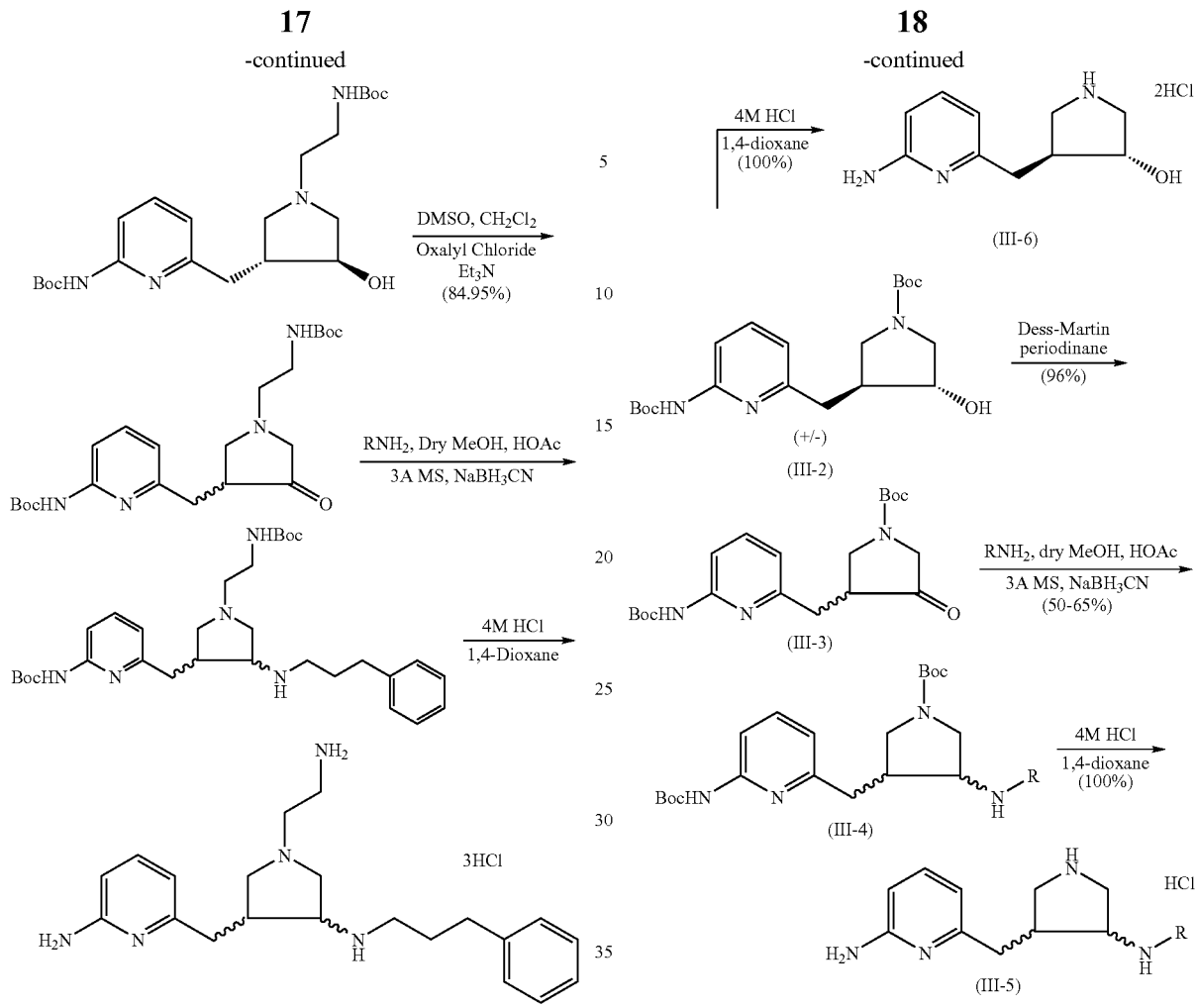

Examples 18-29 can be considered in conjunction with Schemes III and IIIa.

Scheme III

Scheme IIIa

Various amines, RNH$_2$, for use in reductive amination reaction, described in the present synthetic schemes (where Z is NH and R in Scheme IIIa is R$_2$) were prepared as shown. With choice of starting aminoalcohol and/or reagent, each of the benzyl groups of compounds III-8 to III-13 can be, alternatively, substituted at any of the para, meta or ortho positions with a substituent including but not limited to halogen, alkyl or halogenated alkyl. Likewise, via such amines and reductive amination of an oxopyrrolidinyl intermediate, any of the benzyl groups of the compounds of FIG. 3 can be substituted.

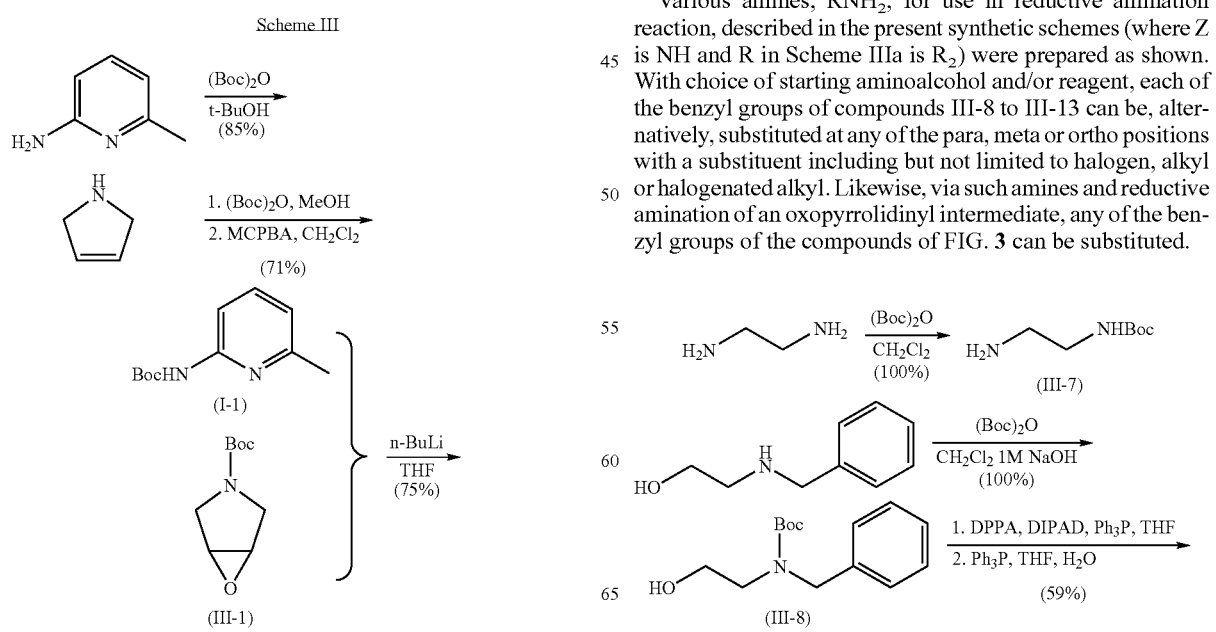

-continued

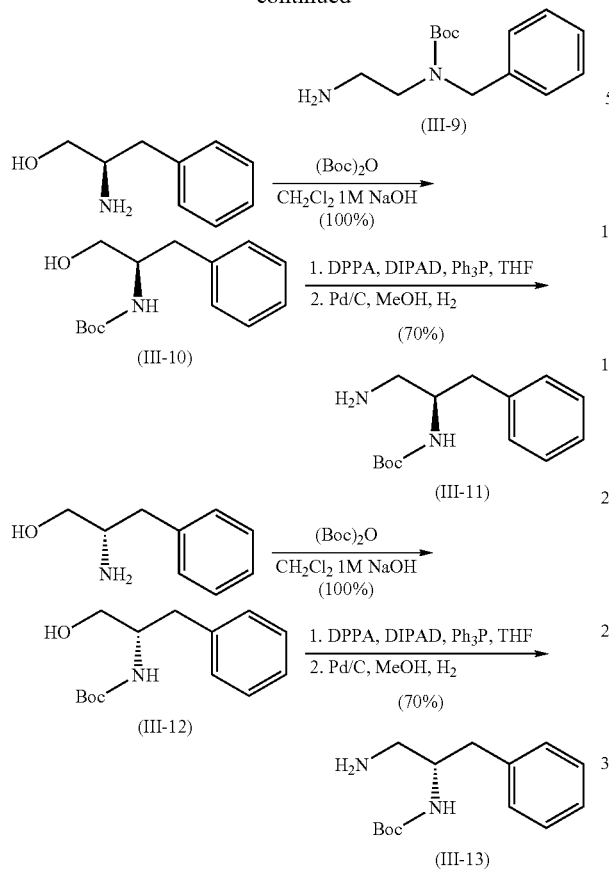

Example 18

Synthesis of 6-oxa-3-aza-bicyclo[3.1.0]hexane-3-carboxylic acid tert-butyl ester (III-1)

Di-tert-butyl dicarbonate (0.015 mol) was added in portions to a solution of 3-pyrroline (0.01 mol, 65% pure) in 20 mL MeOH at 0° C. The reaction mixture was then stirred at room temperature for 24 h. (TLC monitored using 9:1 hexanes/EtOAc). After evaporation of the solvent, the residue was dissolved in 30 mL $CH_2Cl_2$. The reaction mixture was cooled to 0° C. and m-CPBA (0.013 mol, maximum 77% pure) was added in portions. After stirring the mixture at room temperature for 48 h, 20% $Na_2SO_3$ was added and two layers were separated. The aqueous layers were extracted with $CH_2Cl_2$ (20 mL×2). The combined organic extracts were washed with 20% $Na_2SO_3$ (30 mL×2) and water (30 mL×2). The solvent was then removed in vacuo. The residue was purified by column chromatography (silica gel, hexanes:EtOAc, 7:3) to give pure product (71%).

Example 19

The synthetic procedure for 3-(6-tert-butoxycarbonylamino-pyridin-2-ylmethyl)-4-hydroxy-pyrrolidine-1-carboxylic acid tert-butyl ester (III-2) is analogous to that for [6-(1-benzyl-4-hydroxy-pyrrolidin-3-ylmethyl)-pyridin-2-yl]-carbamic acid tert-butyl ester (I-3).

Example 20

Synthesis of 3-(6-tert-butoxycarbonylamino-pyridin-2-ylmethyl)-4-oxo-pyrrolidine-1-carboxylic acid tert-butyl ester (III-3)

To a suspension of Dess-Martin periodinane (0.0014 mol) in 10 mL $CH_2Cl_2$ was added a solution of 3-(6-tert-butoxycarbonylamino-pyridin-2-ylmethyl)-4-hydroxy-pyrrolidine-1-carboxylic acid tert-butyl ester III-2 (0.001 mol) in 5 mL $CH_2Cl_2$ and the reaction mixture was stirred at room temperature for 18 h. 1 M $Na_2S_2O_3$ (10 mL) was added to the reaction, and after stirring for 10 min, the reaction mixture was extracted with $CH_2Cl_2$ (10 mL×3). The combined organic layers were washed with 5% aqueous $NaHCO_3$ (20 mL×3) and brine (20 mL×2). The organic layer was dried over anhydrous $Na_2SO_4$. The solvent was evaporated under reduced pressure. The residue was purified by column chromatography (silica gel, hexanes:EtOAc, 8:2) to give pure product (96%).

Example 21

The synthetic procedure for 3-substituted amino-4-(6-tert-butoxycarbonylamino-pyridin-2-ylmethyl)-pyrrolidine-1-carboxylic acid tert-butyl ester (III-4) is analogous to that for [6-(4-substituted amino-1-benzyl-pyrrolidin-3-ylmethyl)-pyridin-2-yl]-carbamic acid tert-butyl ester (I-5).

Example 22

The synthetic procedure for 6-(4-substituted amino-pyrrolidin-3-ylmethyl)-pyridin-2-ylamine (III-5) is analogous to that for 6-[1-benzyl-4-(substituted amino)-pyrrolidin-3-ylmethyl]-pyridin-2-ylamine (I-6).

Example 23

The synthetic procedure for 4-(6-amino-pyridin-2-ylmethyl)-pyrrolidin-3-ol hydrochloride salt is analogous to that for 4-(6-amino-pyridin-2-ylmethyl)-1-benzyl-pyrrolidin-3-ol hydrochloride salt (I-7).

Example 24

Synthesis of (2-amino-ethyl)-carbamic acid tert-butyl ester (III-7)

A solution of di-tert-butyl dicarbonate (0.01 mol) in dichloromethane (120 mL) was added dropwise to a solution of ethylenediamine (0.06 mol) in 30 mL dichloromethane over 5 h with vigorous stirring. Stirring was continued for a further 24 h at room temperature. After concentration to an oily residue, the reaction mixture was dissolved in aqueous 2M sodium carbonate (60 mL) and extracted with dichloromethane (30 mL×3). The organic layer was washed with 2M sodium carbonate (40 mL×2), and dried over anhydrous $MgSO_4$. The solvent was evaporated under reduced pressure to yield pure product (100%).

Example 25

Synthesis of benzyl-(2-hydroxy-ethyl)-carbamic acid tert-butyl ester (III-8)

A solution of di-tert-butyl dicarbonate (0.01 mol) in $CH_2Cl_2$ (15 mL) was added dropwise to a solution of 2-benzylamino-ethanol (0.01 mol) in 15 mL of CH$_2$Cl$_2$ and 12 mL of 1M NaOH. After stirring 24 h at room temperature, the organic layer was separated, washed with water (25 mL×2) and dried over anhydrous Na$_2$SO$_4$, Removal of solvent under reduced pressure give crude product as an oil, which was purified by column chromatography (silica gel, hexanes:EtOAc, 7:3) (100%).

Example 26

Synthesis of (2-amino-ethyl)-benzyl-carbamic acid tert-butyl ester (III-9)

Triphenylphosphine (0.0125 mol) in dry THF (10 mL) was added to benzyl-(2-hydroxy-ethyl)-carbamic acid tert-butyl ester III-8 in THF (30 mL) at 0° C. under nitrogen via a cannula. Diisopropyl azodicarboxylate (DIPAD) (0.013 mol) was then added dropwise and the solution was stirred for 20 min at 0° C. after the addition of DIPAD. Diphenyl phosphonic azide (DPPA) (0.0125 mol) was added at 0° C. and the solution was stirred for 5 h at room temperature (TLC monitor the amount of III-8). The solution was then concentrated in vacuo and the crude residue was purified by column chromatography to yield azide intermediate (silica gel, hexanes:EtOAc, 9.5:0.5).

To a solution of above azide intermediate in THF (5 mL) were added Ph$_3$P (0.012 mol) and water (0.03 mol) at 0° C. The mixture was stirred 2 h at 0° C. and 21 h at room temperature. The solvent was removed under reduced pressure, and the residue was treated with 10% citric acid (30 mL) and EtOAc (15 mL). The aqueous layer separated was washed EtOAc (10 mL×2). Then the aqueous layer was basified with 2M NaOH and the alkaline solution was extracted with CH$_2$Cl$_2$ (30 mL×3). The extracts were dried over anhydrous MgSO$_4$, and the solvent was then removed under reduced pressure to give pure product.

Example 27

The synthetic procedure for (2R)-2-N-Boc-amino-3-phenyl-1-propanol (III-10) and (2S)-2-N-Boc-amino-3-phenyl-1-propanol (III-12) is analogous to that for benzyl-(2-hydroxy-ethyl)-carbamic acid tert-butyl ester (III-8).

Example 28

Synthesis of (2R)-2-N-Boc-3-phenyl-propane-1,2-diamine (III-11) or (2S)-2-N-Boc-3-phenyl-propane-1,2-diamine (III-13)

Triphenylphosphine (0.0125 mol) in dry THF (10 mL) was added to 2-N-Boc-amino-3-phenyl-1-propanol (III-10 or III-12) in THF (30 mL) at 0° C. under nitrogen via a cannula. Diisopropyl azodicarboxylate (DIPAD) (0.013 mol) was then added dropwise, and the solution was stirred for 20 min at 0° C. after the addition of DIPAD. Diphenyl phosphonic azide (DPPA) (0.0125 mol) was added at 0° C., and the solution was stirred for 5 h at room temperature (TLC monitor the amount of III-10, or III-12). The solution was then concentrated in vacuo and the crude residue was purified by column chromatography to yield azide intermediate (silica gel, hexanes:EtOAc, 9.5:0.5).

The above azide intermediate was dissolved in 10 ml MeOH containing a catalytic amount of 10% Pd/C (0.5 g). The solution was stirred under a H$_2$ atmosphere at room temperature for 24 h. The solution was then filtered through Celite, and the filtrate was concentrated in vacuo. The residue was treated with 10% citric acid (30 mL) and EtOAc (15 mL). The aqueous layer separated was washed EtOAc (10 mL×2). Then the aqueous layer was basified with 2M NaOH and the alkaline solution was extracted with CH$_2$Cl$_2$ (30 mL×3). The extracts were dried over anhydrous MgSO$_4$, and the solvent was then removed under reduced pressure to give pure product.

Example 29

Figure 3:
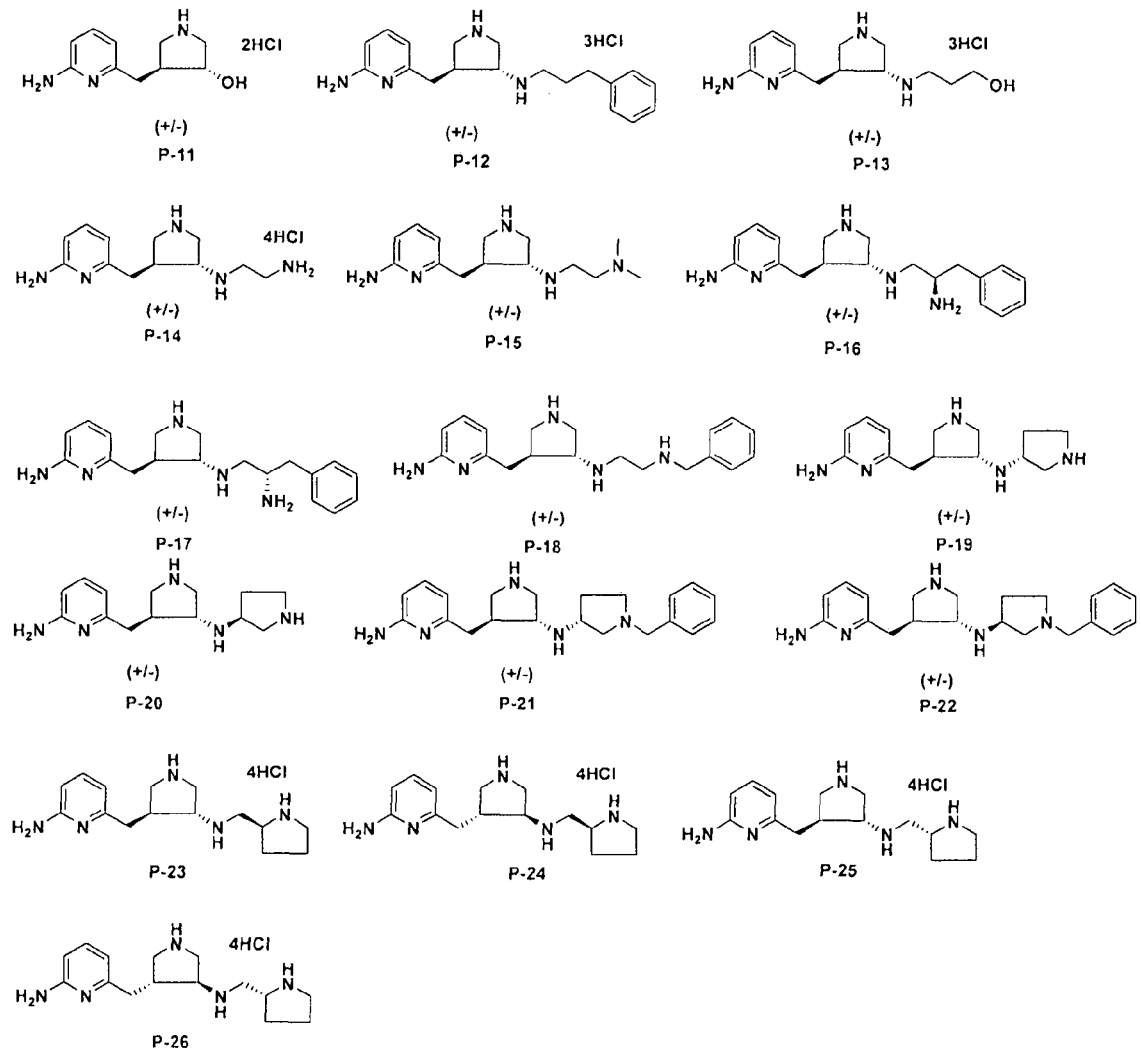
Figure 4:
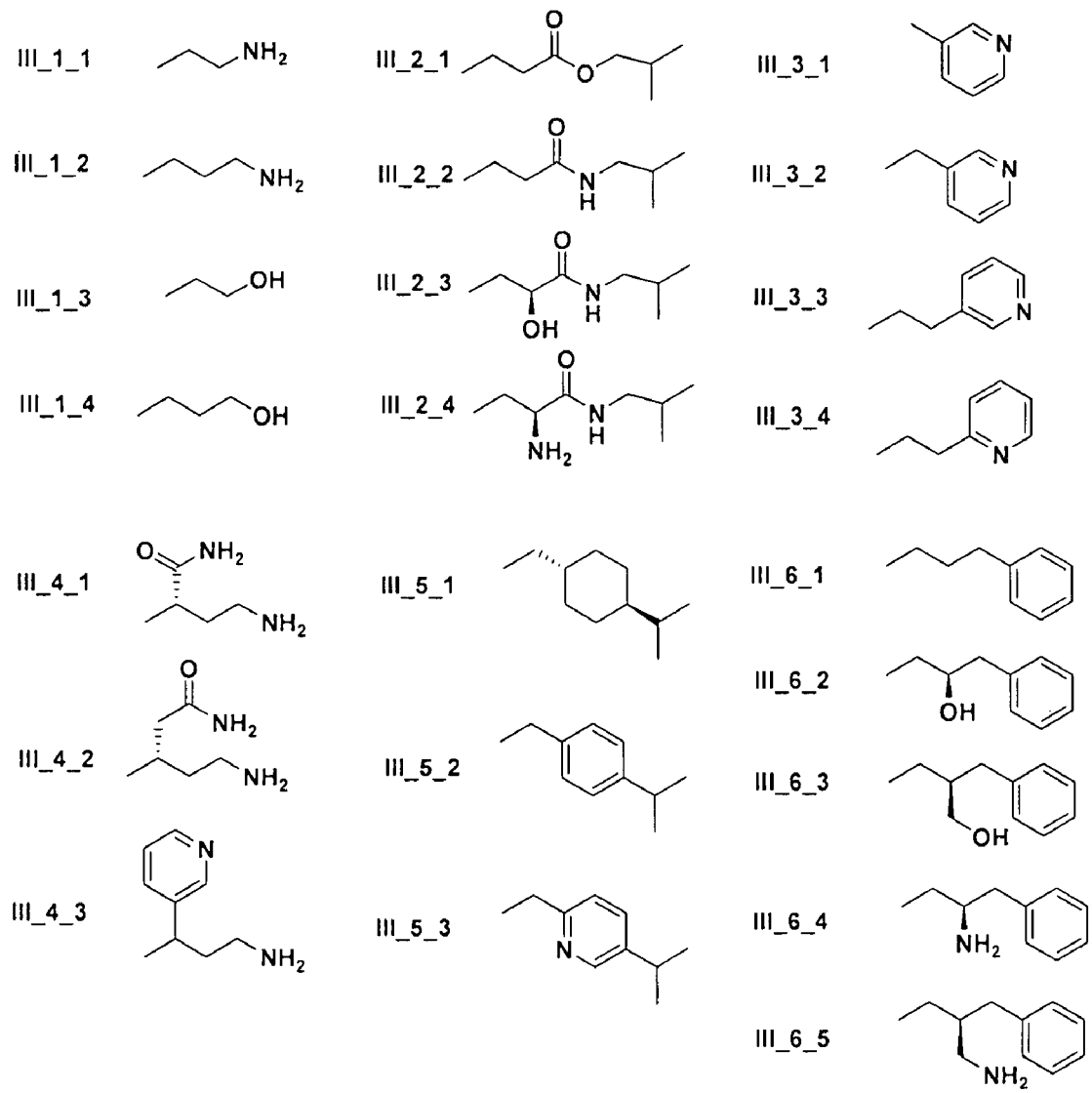
FIG. 4 provides, without limitation, various $R_2$ moieties corresponding to substructure III of compounds in accordance with this invention.

Various other compounds, including those of FIG. 3, were prepared in accordance with the synthetic routes of Schemes III and IIIa. (Other R$_2$ moieties corresponding to substructure III, whether Z is NH or O, are provided in FIG. 4.) All the chemical structures were confirmed by $^1$H NMR, $^{13}$CNMR, and mass spectra. All of the products, except P-23 through P-26, and P-36 through P-43, are racemic mixtures.

Example 30

In accordance with Scheme III and compound III-5, compounds P-13 and P-38 of FIG. 3 were prepared as shown in Scheme IIIb, below.

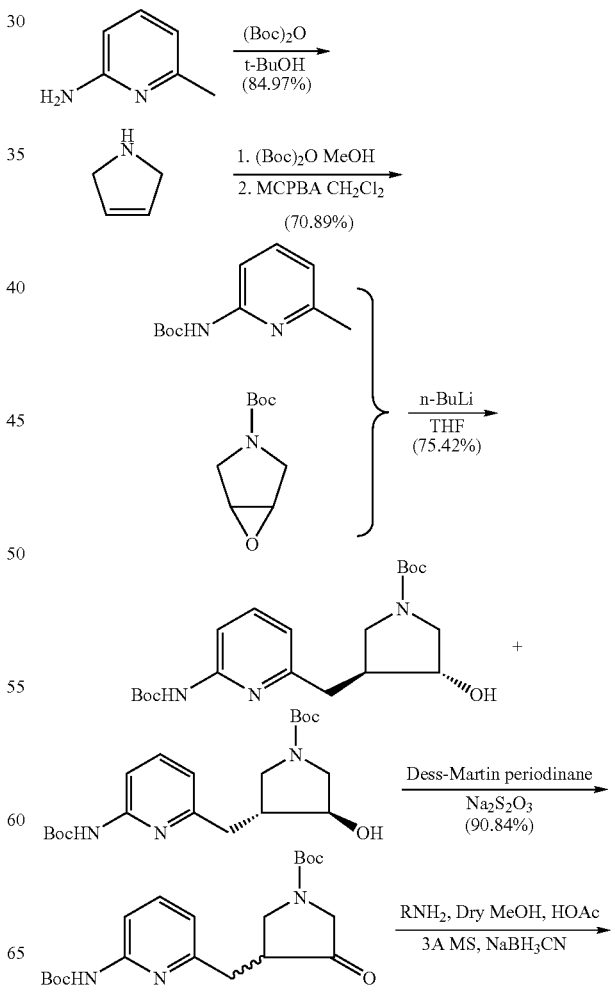

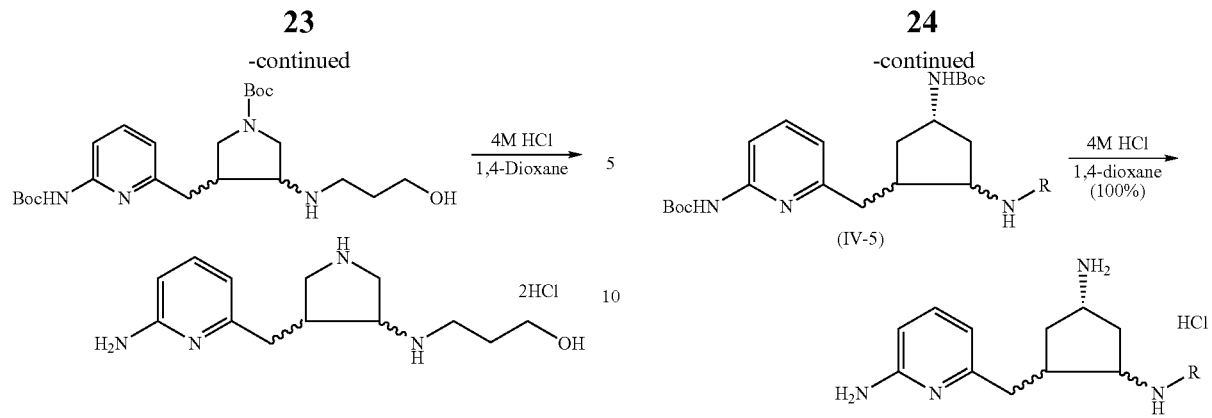

Examples 31-38 can be considered in conjunction with Scheme IV, below.

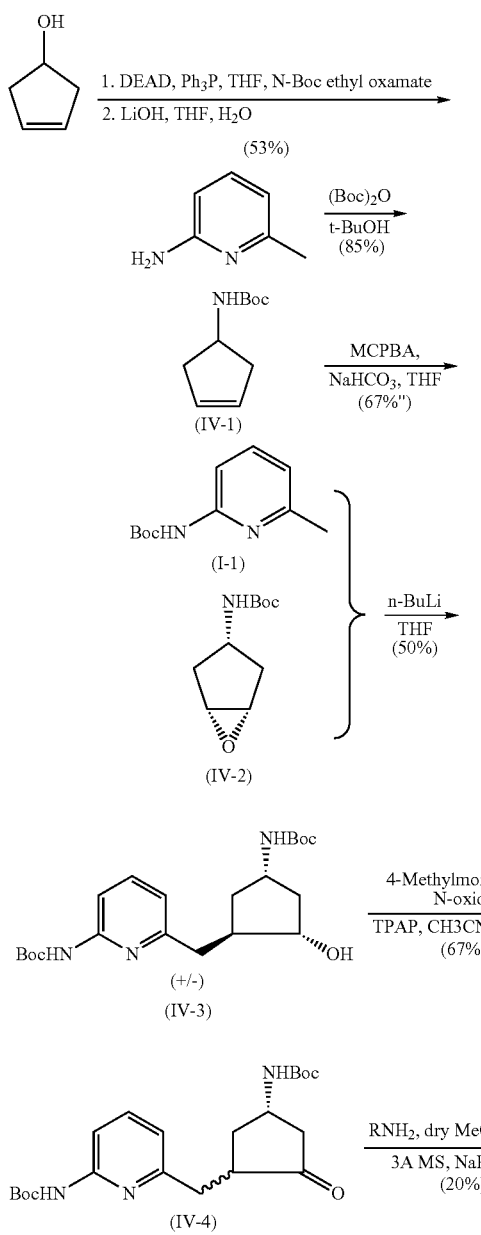

Example 31

Synthesis of cyclopent-3-enyl-carbamic acid tert-butyl ester (IV-1)

To a 3-necked round bottom flask cooled in an ice-water bath was added a solution of $Ph_3P$ (0.015 mol) in anhydrous THF (10 mL), a solution of 3-cyclopenten-1-ol (II) (0.012 mol) in anhydrous THF (10 mL), and a solution of N-Boc ethyl oxamate (0.015 mol) in anhydrous THF (10 mL). DEAD (0.015 mol) was then added dropwise to the above mixture. The reaction mixture was stirred at 0° C. for 2 h, and then allowed to react at room temperature for 48 h. The solvent was removed in vacuo and the residue was dissolved in $CH_2Cl_2$ (30 mL), and washed with water and brine (20 mL×3). The solvent was removed in vacuo, and the residue was purified by column chromatography (silica gel, 100% dichloromethane) to yield a mixture of product, (tert-butoxy-carbonyl-cyclopent-3-enyl-amino)-oxo-acetic acid ethyl ester, and N-Boc ethyl oxamate that was used without further purification.

To a stirred solution cooled in an ice-water bath of the above crude product, (tert-butoxycarbonyl-cyclopent-3-enyl-amino)-oxo-acetic acid ethyl ester, (3.80 g) in THF (35 mL) was added a solution of LiOH (0.0765 mol) in water (35 mL). The mixture was stirred in the ice-water bath for 3 h. The organic material was extracted with $CH_2Cl_2$ (30 mL×3), the organic layers were combined and washed with brine (30 mL×2), and the solvent was removed in vacuo. The residue was purified by column chromatography (silica gel, 100% dichloromethane) to obtain white crystals of pure product (53%).

Example 32

Synthesis of cis-(6-oxa-bicyclo[3.1.0]hex-3-yl)-carbamic acid tert-butyl ester (IV-2)

Solid $NaHCO_3$ (0.0167 mol) and m-CPBA (0.0128 mol) were added in portions to a stirred solution of cyclopent-3-enyl-carbamic acid tert-butyl ester IV-1 (0.0093 mol) in $CH_2Cl_2$ (60 mL). The mixture was stirred at 0° C. for the first 2 h of the reaction and then allowed to stir for about 48 h at room temperature. Aqueous 20% $Na_2SO_3$ (30 mL) was added, and the two layers were separated. The aqueous layer was extracted with $CH_2Cl_2$ (20 mL×3), and the combined organic layers were washed with 20% $Na_2SO_3$ (30 mL×1), 5% $NaHCO_3$ (30 mL×1), and water (30 mL×1). The combined organic phase was concentrated in vacuo, and the residue was purified by column chromatography (silica gel, 100% dichloromethane) to give pure product as a colorless oil (64%).

Example 33

Synthesis of [6-(4-tert-butoxycarbonylamino-2-hydroxy-cyclopentylmethyl)-pyridin-2-yl]-carbamic acid tert-butyl ester (IV-3)

A solution of (6-methyl-pyridin-2-yl)-carbamic acid tert-butyl ester I-1 (0.0028 mol) in THF (10 mL) was cooled to −78° C. under $N_2$. To the cooled solution, n-BuLi (1.6 M in hexanes, 0.0097 mol) was added dropwise over 50 min. The solution changed from colorless to orange, then to red. After being stirred for 30 min at −78° C. the solution was stirred at room temperature for 30 min at which point it became dark red. The reaction mixture was cooled to −78° C. and cis-(6-oxa-bicyclo[3.1.0]hex-3-yl)-carbamic acid tert-butyl ester IV-2 (0.0032 mol) was added over a period of 2 h. After addition was complete, the mixture was stirred at −78° C. for 2 h and then stirring continued at room temperature for 2 h. The reaction mixture was quenched with the addition of ice-water and was extracted with $CH_2Cl_2$ (20 mL×3). The combined organic layers were washed with brine (30 mL×1) and concentrated in vacuo. After column chromatography (silica gel, hexanes:EtOAc, 1:1), pure product was obtained as a white-yellow solid (50%).

Example 34

Synthesis of [6-(4-tert-butoxycarbonylamino-2-oxo-cyclopentylmethyl)-pyridin-2-yl]-carbamic acid tert-butyl ester (IV-4)

Tetrapropylammonium perruthenate (0.07 mmol, 5 mol %) was added to a stirred solution of [6-(4-tert-butoxycarbonylamino-2-hydroxy-cyclopentylmethyl)-pyridin-2-yl]-carbamic acid tert-butyl ester IV-3 (0.14 mmol) and N-methyl-morpholine-N-oxide (0.26 mmol) in dichloromethane (9 mL) and acetonitrile (1 mL) at room temperature, and was allowed to react overnight. When complete, the solvent was evaporated in vacuo and the residue was purified by column chromatography (silica gel, $CH_2Cl_2$:EtOAc, 8:2) to afford pure product as a white solid (67%).

Example 35

The synthetic procedure for [6-(2-substituted amino-4-tert-butoxycarbonylamino-cyclopentylmethyl)-pyridin-2-yl]-carbamic acid tert-butyl ester (IV-5) is analogous to that for [6-(4-substituted amino-1-benzyl-pyrrolidin-3-ylmethyl)-pyridin-2-yl]-carbamic acid tert-butyl ester (I-5).

Example 36

The synthetic procedure for 4-(6-amino-pyridin-2-ylmethyl)-$N^3$-substituted-cyclopentane-1,3-diamine (IV-6) is analogous to that for 6-[1-benzyl-4-(substituted amino)-pyrrolidin-3-ylmethyl]-pyridin-2-ylamine hydrochloride salt (I-6)

Example 37

Figure 5:
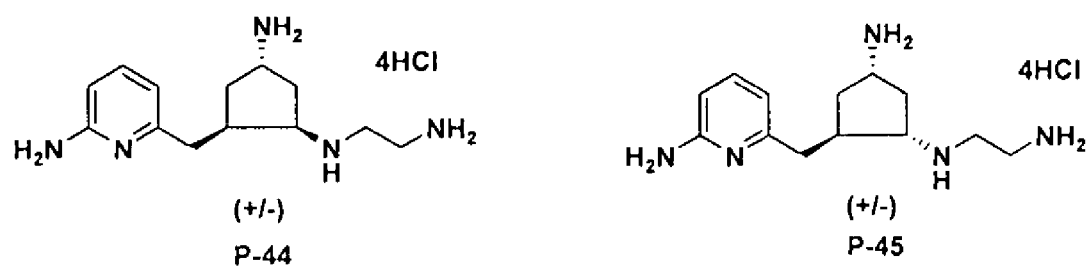
FIGS. 5 and 6 provide several cis and trans isomers of compounds in accordance with this invention.

Various other compounds, including those of FIG. 5, were prepared in accordance with the synthetic route of Scheme IV. All of the chemical structures were confirmed by $^1H$ NMR, $^{13}C$ NMR, and mass spectra. All of the products are racemic mixtures.

Example 38

In accordance with Scheme IV and compound IV-6, compounds P-44 and P-45 of FIG. 5 were prepared as provided in Scheme IVa, below.

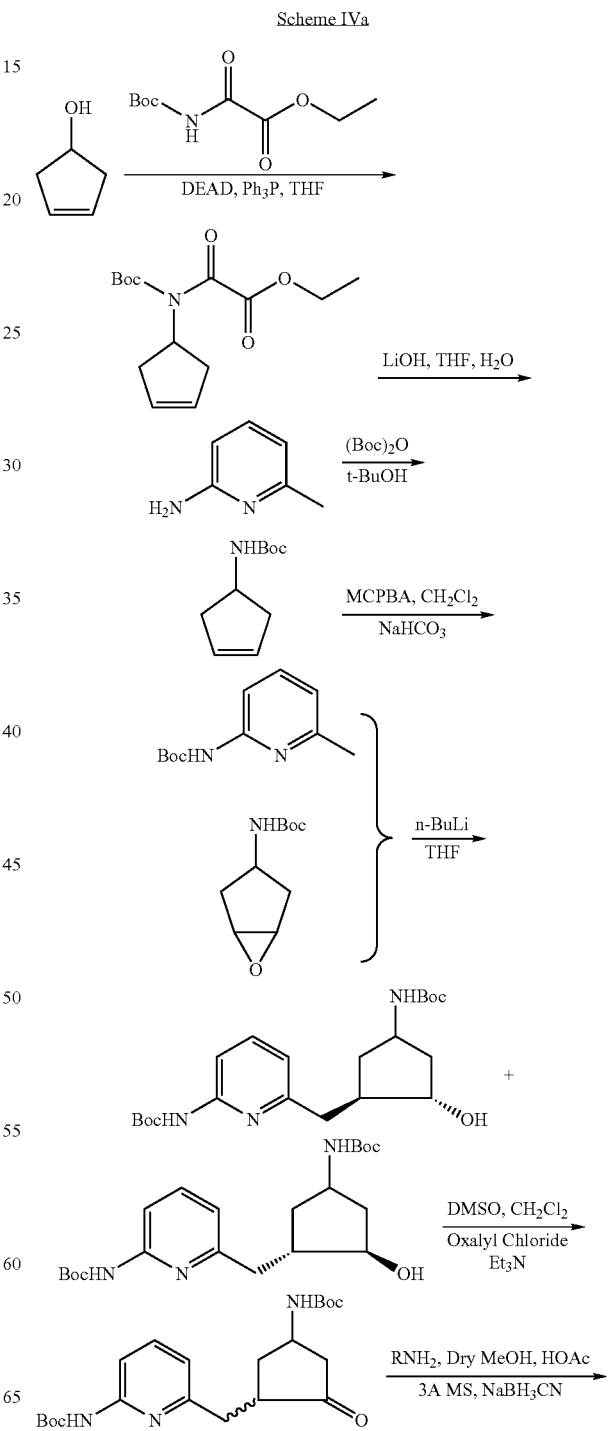

-continued

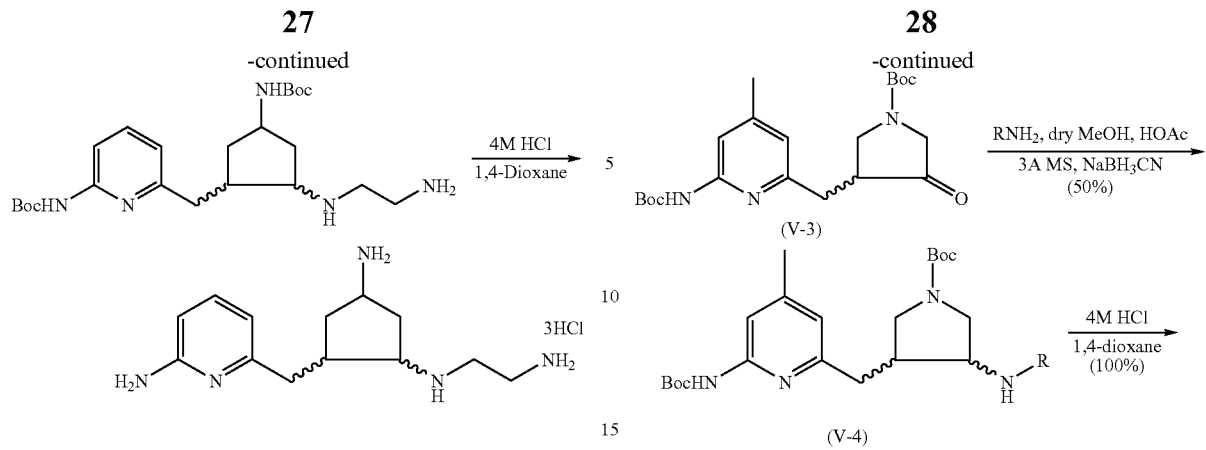

Examples 39-44 can be considered in conjunction with Scheme V, below.

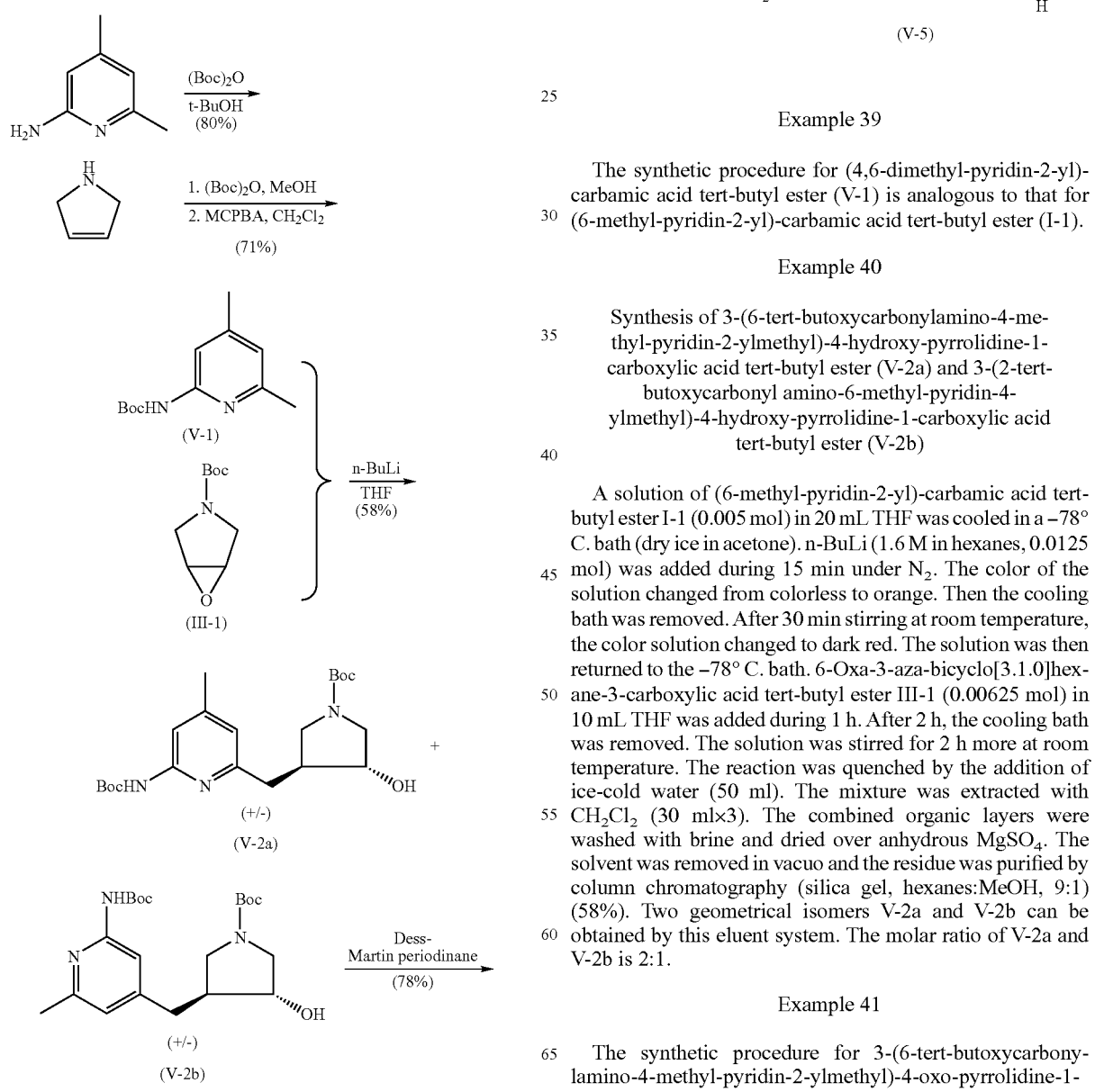

Example 39

The synthetic procedure for (4,6-dimethyl-pyridin-2-yl)-carbamic acid tert-butyl ester (V-1) is analogous to that for (6-methyl-pyridin-2-yl)-carbamic acid tert-butyl ester (I-1).

Example 40

Synthesis of 3-(6-tert-butoxycarbonylamino-4-methyl-pyridin-2-ylmethyl)-4-hydroxy-pyrrolidine-1-carboxylic acid tert-butyl ester (V-2a) and 3-(2-tert-butoxycarbonyl amino-6-methyl-pyridin-4-ylmethyl)-4-hydroxy-pyrrolidine-1-carboxylic acid tert-butyl ester (V-2b)

A solution of (6-methyl-pyridin-2-yl)-carbamic acid tert-butyl ester I-1 (0.005 mol) in 20 mL THF was cooled in a −78° C. bath (dry ice in acetone). n-BuLi (1.6 M in hexanes, 0.0125 mol) was added during 15 min under $N_2$. The color of the solution changed from colorless to orange. Then the cooling bath was removed. After 30 min stirring at room temperature, the color solution changed to dark red. The solution was then returned to the −78° C. bath. 6-Oxa-3-aza-bicyclo[3.1.0]hexane-3-carboxylic acid tert-butyl ester III-1 (0.00625 mol) in 10 mL THF was added during 1 h. After 2 h, the cooling bath was removed. The solution was stirred for 2 h more at room temperature. The reaction was quenched by the addition of ice-cold water (50 ml). The mixture was extracted with $CH_2Cl_2$ (30 ml×3). The combined organic layers were washed with brine and dried over anhydrous $MgSO_4$. The solvent was removed in vacuo and the residue was purified by column chromatography (silica gel, hexanes:MeOH, 9:1) (58%). Two geometrical isomers V-2a and V-2b can be obtained by this eluent system. The molar ratio of V-2a and V-2b is 2:1.

Example 41

The synthetic procedure for 3-(6-tert-butoxycarbonylamino-4-methyl-pyridin-2-ylmethyl)-4-oxo-pyrrolidine-1-carboxylic acid tert-butyl ester (V-3) is analogous to that for 3-(6-tert-butoxycarbonylamino-pyridin-2-ylmethyl)-4-oxo-pyrrolidine-1-carboxylic acid tert-butyl ester (III-3).

Example 42

The synthetic procedure for 3-substituted amino-4-(6-tert-butoxycarbonylamino-4-methyl-pyridin-2-ylmethyl)-pyrrolidine-1-carboxylic acid tert-butyl ester (V-4) is analogous to that for [6-(4-substituted amino-1-benzyl-pyrrolidin-3-ylmethyl)-pyridin-2-yl]-carbamic acid tert-butyl ester (I-5).

Example 43

The synthetic procedure for 4-methyl-6-(4-substituted amino-pyrrolidin-3-ylmethyl)-pyridin-2-ylamine (V-5) is analogous to that for 6-[1-benzyl-4-(substituted amino)-pyrrolidin-3-ylmethyl]-pyridin-2-ylamine (I-6).

Example 44

Figure 6:
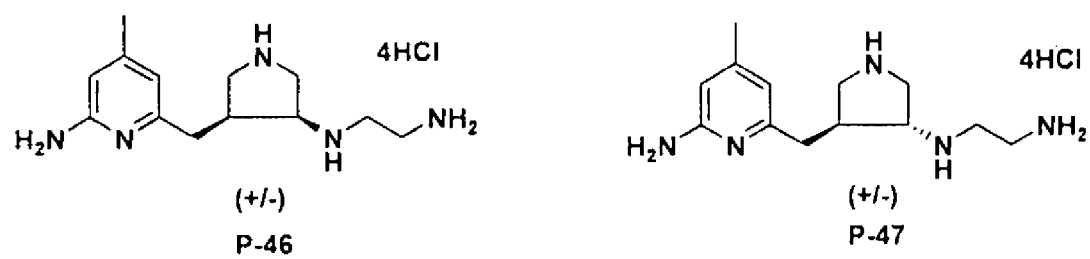

Various other compounds, including those of FIG. 6, were prepared in accordance with the synthetic route of Scheme V. All the chemical structures were confirmed by $^1$H NMR, $^{13}$CNMR, and mass spectra. All of the products are racemic mixtures.

Example 45 and compounds in accordance therewith can be considered in conjunction with Schemes VI-VII, below.

Scheme VI

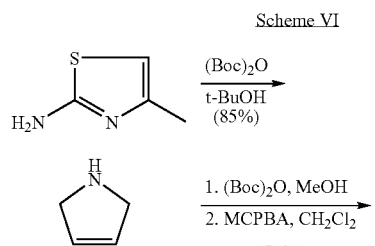

(IV-1)

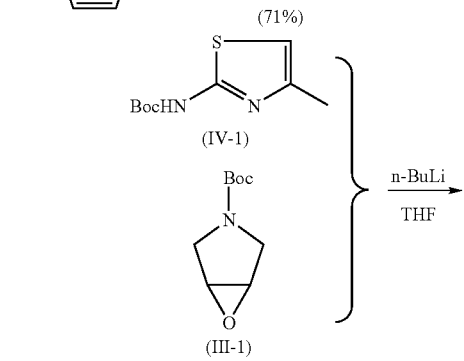

(IV-2)

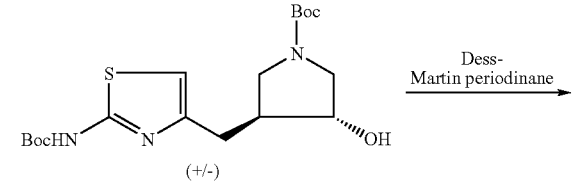

(IV-3)

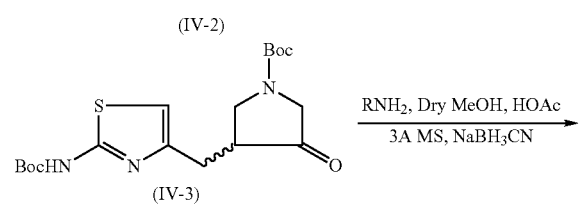

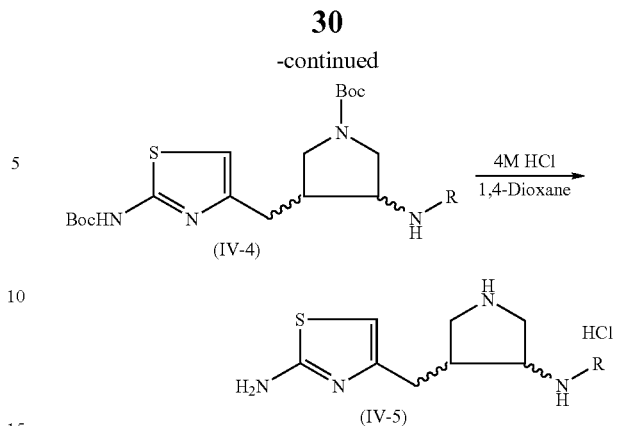

Scheme VII

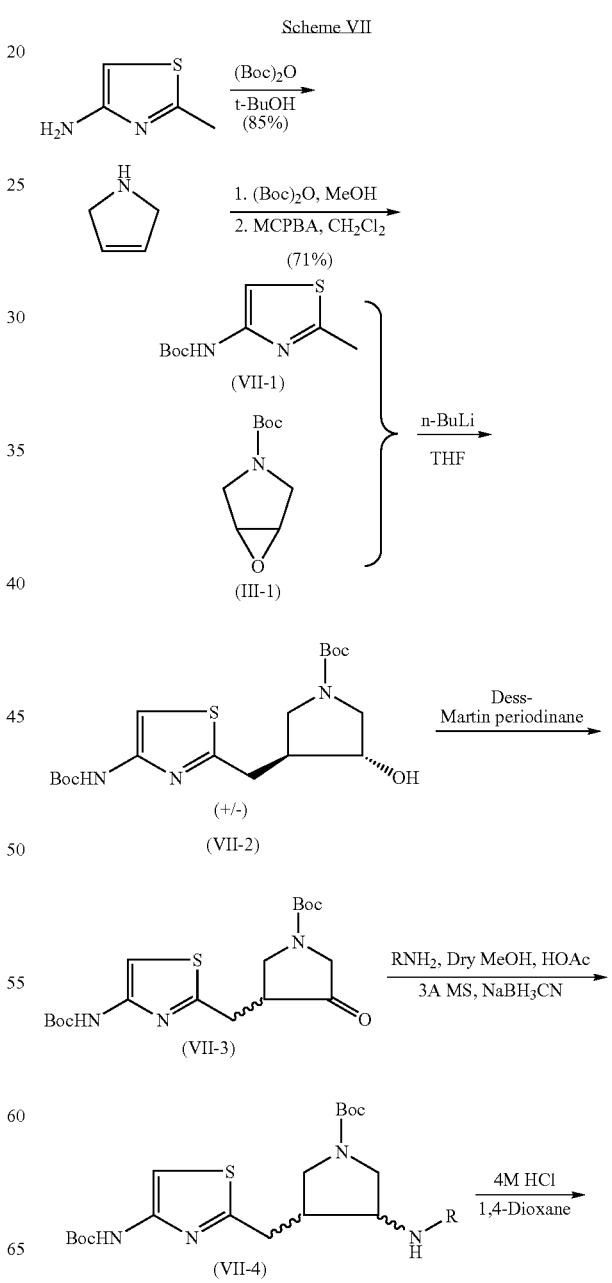

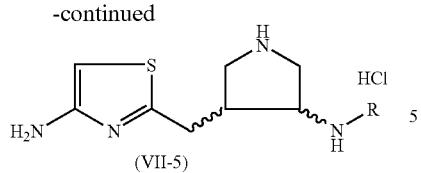

Example 45

Synthesis of (4-methyl-thiazol-2-yl)-carbamic acid tert-butyl ester (VII-1)

To a round bottom flask containing 40 mL CH$_2$Cl$_2$ was added I (695 mg, 6.09 mmol), 4-DMAP (52.3 mg, 0.43 mmol), and Boc$_2$O (1.374 g, 6.29 mmol). The reaction mixture was stirred overnight at room temperature. Concentration of the solution in vacuo was followed by purification by column chromatography (silica gel, hexanes:EtOAc, 10:1), affording the product as white crystals (54%).

Example 46

In accordance with Scheme VI, various n-substituted pyrrolyl thiazoline compounds were prepared as provided in Scheme IVa, below.

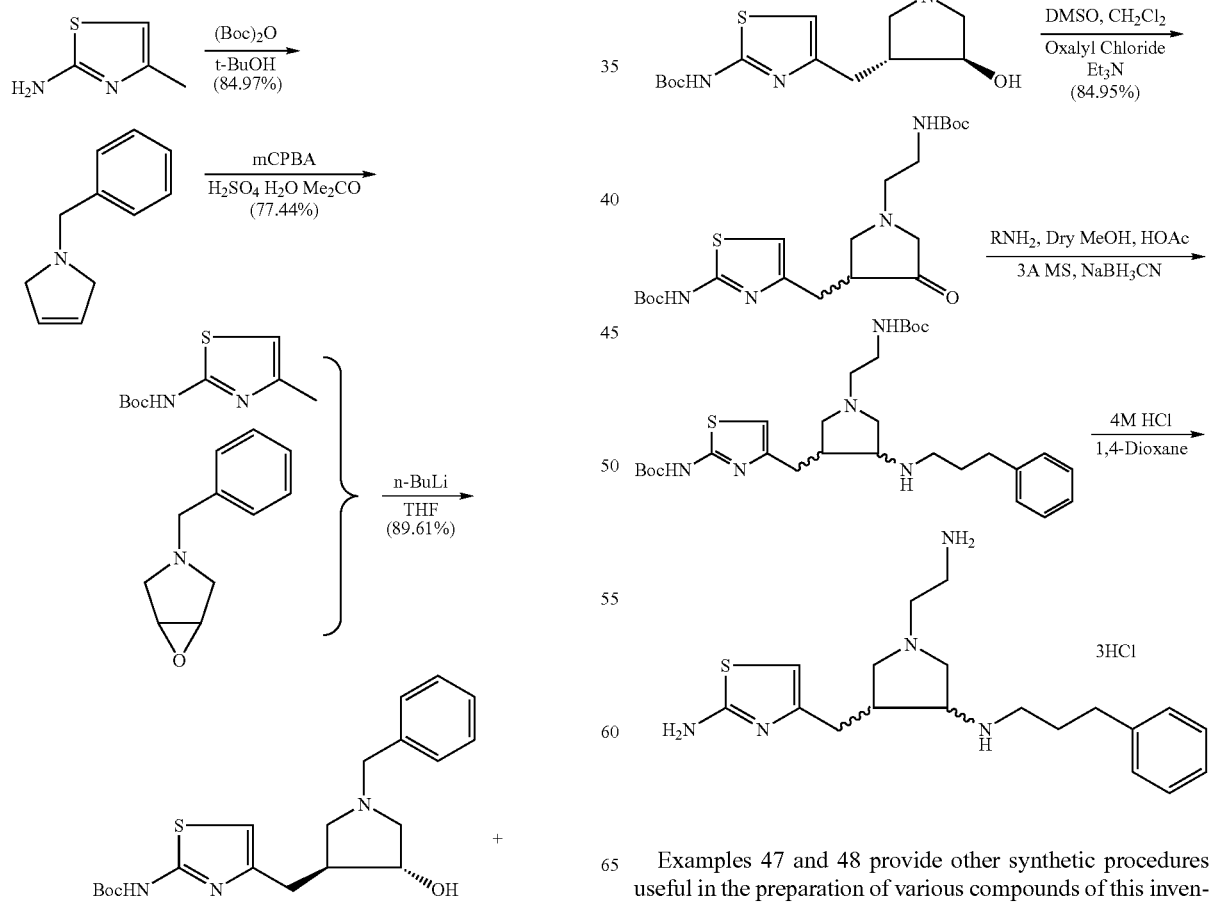

Examples 47 and 48 provide other synthetic procedures useful in the preparation of various compounds of this invention, as shown in Schemes I-VII.

Example 47

Synthesis of [6-(4-hydroxypyrrolidin-3-ylmethyl)-pyridin-2-yl]-carbamic acid tert-butyl ester, illustrating pyrrolidine reduction.

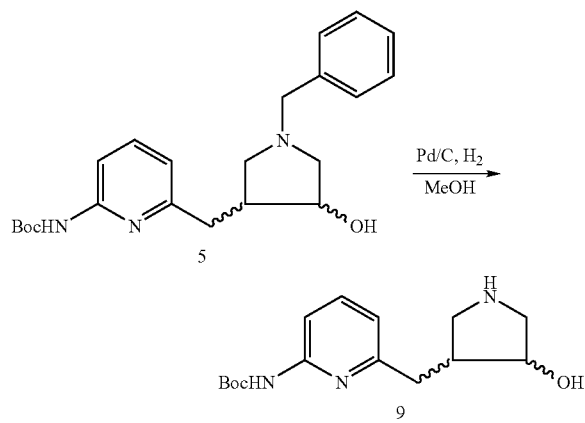

A suspension of 5 (0.002 mol) and 10% Pd—C (0.7 g) in MeOH (30 mL) was stirred at 45° C. under hydrogen (1 atm) for 7 h. Then the catalyst was removed by filtration and was washed with MeOH. The filtrate was concentrated to give 9 (100% yield). Most of the product was used in the next reaction without further purification. Some was purified by flash chromatography (silica gel, $CH_2Cl_2$:MeOH:$Et_3N$, 6:3:0.25) for structure analysis.

Example 48

Synthesis of 3-(6-tert-butoxycarbonylaminopyridin-2-ylmethyl)-4-oxo-pyrrolidine-1-carboxylic acid tert-butyl ester, illustrating pyrrolidine oxidation.

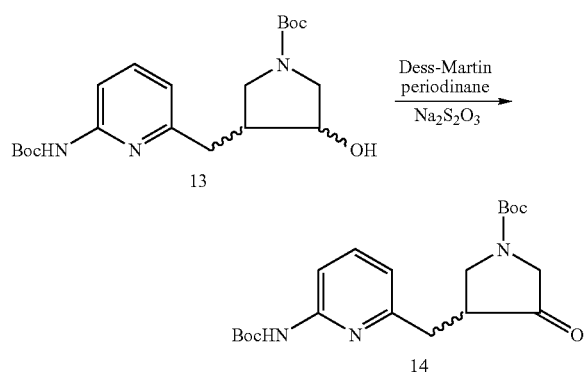

To a suspension of Dess-Martin periodinane (0.0014 mol) in 10 mL of $CH_2Cl_2$ was added a solution of 13 (0.001 mol) in 5 mL of $CH_2Cl_2$, and the reaction mixture was stirred at room temperature for 18 h. 1 M $Na_2S_2O_3$ (10 mL) was added to the reaction, and after stirring for 10 min the reaction mixture was extracted with $CH_2Cl_2$ (3×10 mL). The combined organic layers were washed with 5% aqueous $NaHCO_3$ (20 mL) and brine (20 mL). The organic layer was dried over $Na_2SO_4$ and evaporated. The mixture was purified by flash chromatography to give 14 in 96% yield (silica gel, $CH_2Cl_2$:EtOAc, 9.5:0.5).

Example 49

In accordance with the preceding, various other compounds can be prepared in an analogous fashion using comparable synthetic techniques or straightforward modifications thereof, as would be understood by those skilled in the art. For instance, compounds having substructure I comprising a thiazine (X=S, m=n=1), oxazine (X=O, m=n=1), pyrazine (X=N, m=n=1), oxazole (X=O, m=1 and n=0 or m=0 and n=1) or imidazole (X=N, m=1 and n=0 or m=0 and n=1) moiety can be prepared from the appropriate starting material using synthetic procedures of the sort described in Schemes I-VII. Likewise, compounds having substructure II comprising a cyclohexane (Y=CH, p=1, q=2 or p=2, q=1) or piperidine (Y=N, p=1, q=2 or p=2, q=1) moiety can be obtained using a suitable starting material. As would also be understood, any $R_2$ moiety of substructure III (Z=O or NH) can be introduced, limited only by the corresponding amine availability and its reactivity under the reductive amination conditions employed (Z=NH) or ether formation (Z=O) by alkylation of the corresponding alcohol directly after epoxide opening or after oxidation to the ketone followed by reduction and separation of the cis and trans alcohols.

Example 50

With regard to variation of substructure III, consider compounds in accordance with this invention, where $R_3$ can be a linear or cyclic aminoalkyl moiety. In particular, with reference to the compounds of this example, such moieties can comprise a benzyl group (X=H) or a substituted phenyl variation thereof (e.g., X can be but not limited to halogen, alkyl, or halogenated alkyl at any of the para, meta or ortho positions). Such compounds are prepared using an appropriate amine reagent (e.g., a substituted phenyl variation of amine III-9 in Scheme IIIa) for reductive amination of the corresponding oxopyrrolidinyl intermediate, in turn available via ring-opening reaction of lithiated 2-amino-4,6-dimethylpyridine with pyrroline epoxide, as demonstrated elsewhere herein.

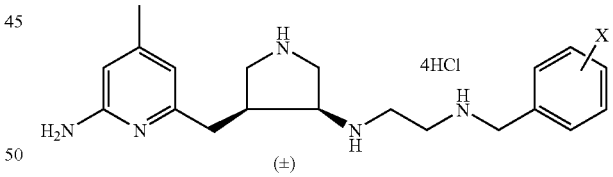

N-[4-(6-Amino-4-methyl-pyridin-2-ylmethyl)-pyrrolidin-3-yl]-N'-(2-, 3-, or 4-Xbenzyl)-ethane-1,2-diamine

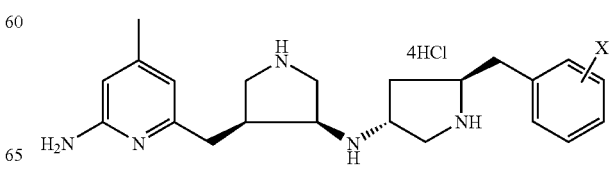

6-[4-(5-(2-, 3-, or 4-Xbenzyl-pyrrolidin-3-ylamino)-pyrrolidin-3-ylmethyl]-4-methyl-pyridin-2-ylamine Examples 51-74 can be considered in conjunction with Schemes 1'-VI' below.

Scheme I'

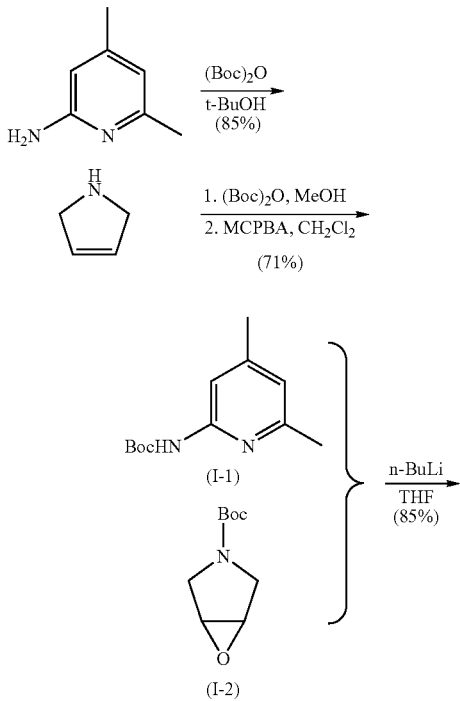

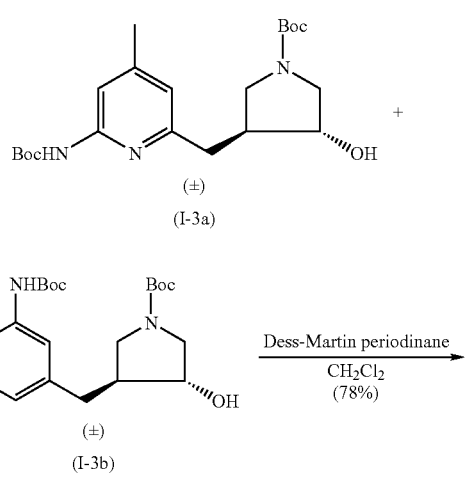

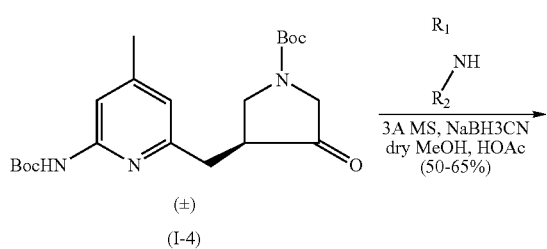

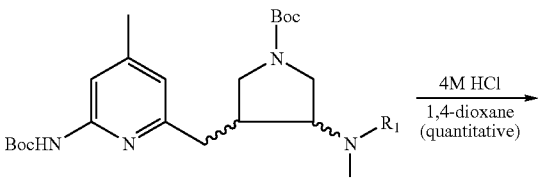

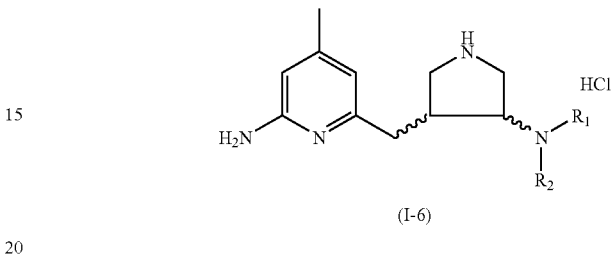

Various amines, $R_1NHR_2$ in Scheme I', for use in reductive amination reaction, described in the present synthetic schemes (where Z of general structure is N, and $R_3$ of general structure is $R_1$ and $R_2$ in Scheme I') were prepared as shown below. Each of the phenyl groups of compounds II-3a to II-3h in Scheme II', III-3 in Scheme III', IV-2 in Scheme IV', V-5a to V-5c in Scheme V', and VI-3 in Scheme VI' can be, alternatively, substituted at any of the para, meta or ortho positions with substituents including but not limited to halogen, alkyl or halogenated alkyl. Likewise, via such amines and reductive amination of an oxapyrrolidinyl intermediate, any of the phenyl groups of the compounds of FIG. 7 can be substituted.

Scheme II'

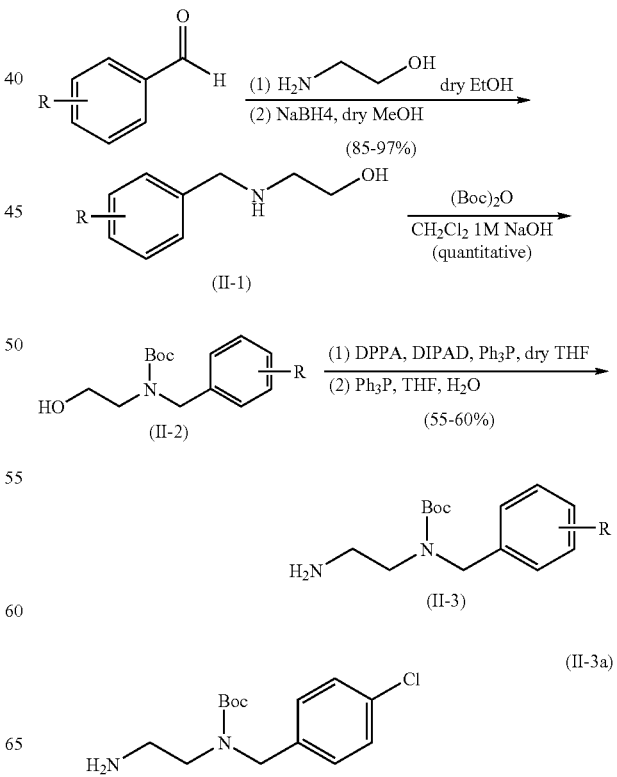

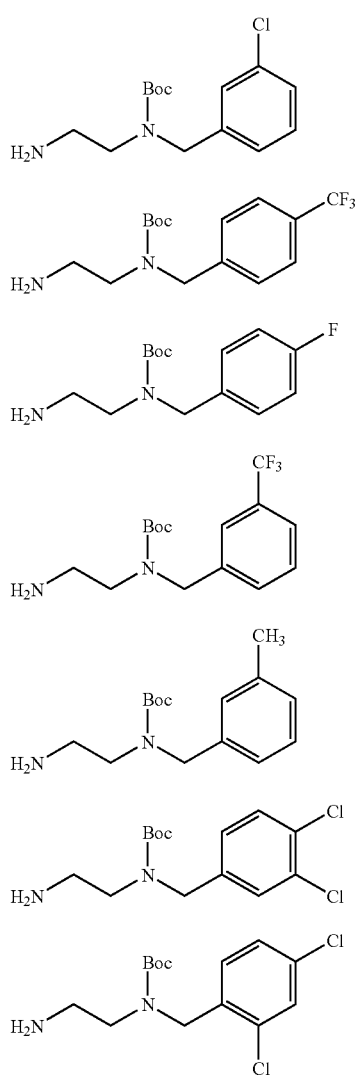
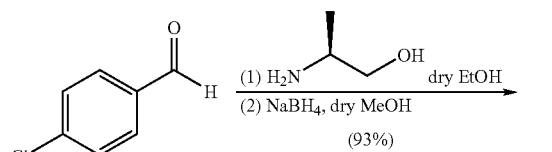
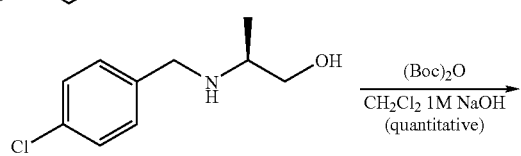
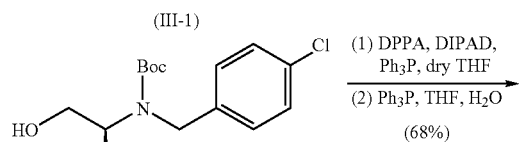
Scheme IV'
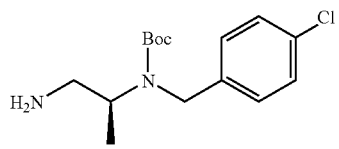
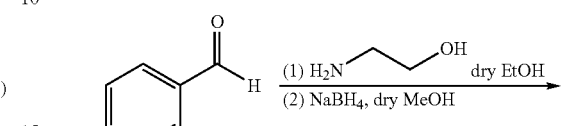
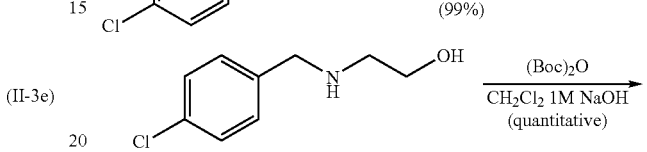
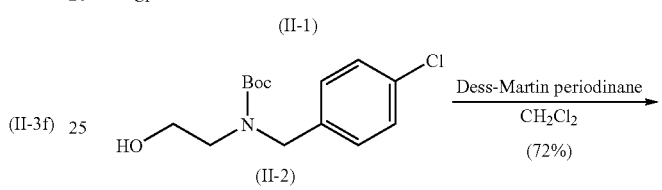
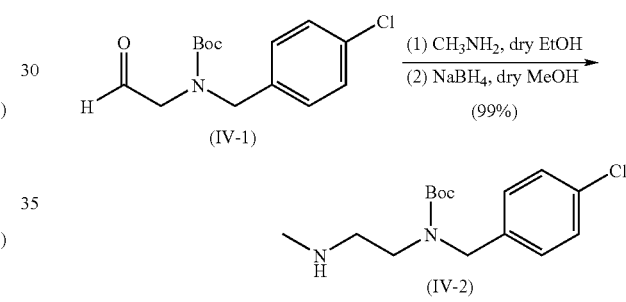
Scheme V'
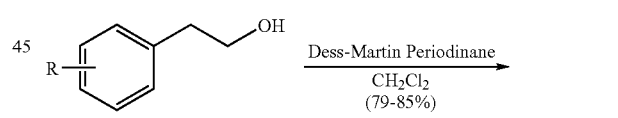
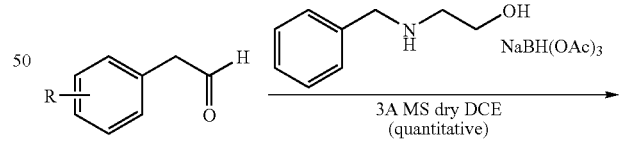
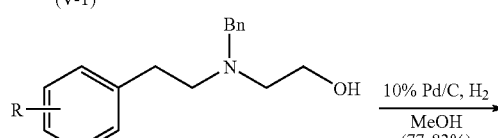
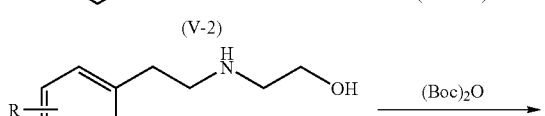

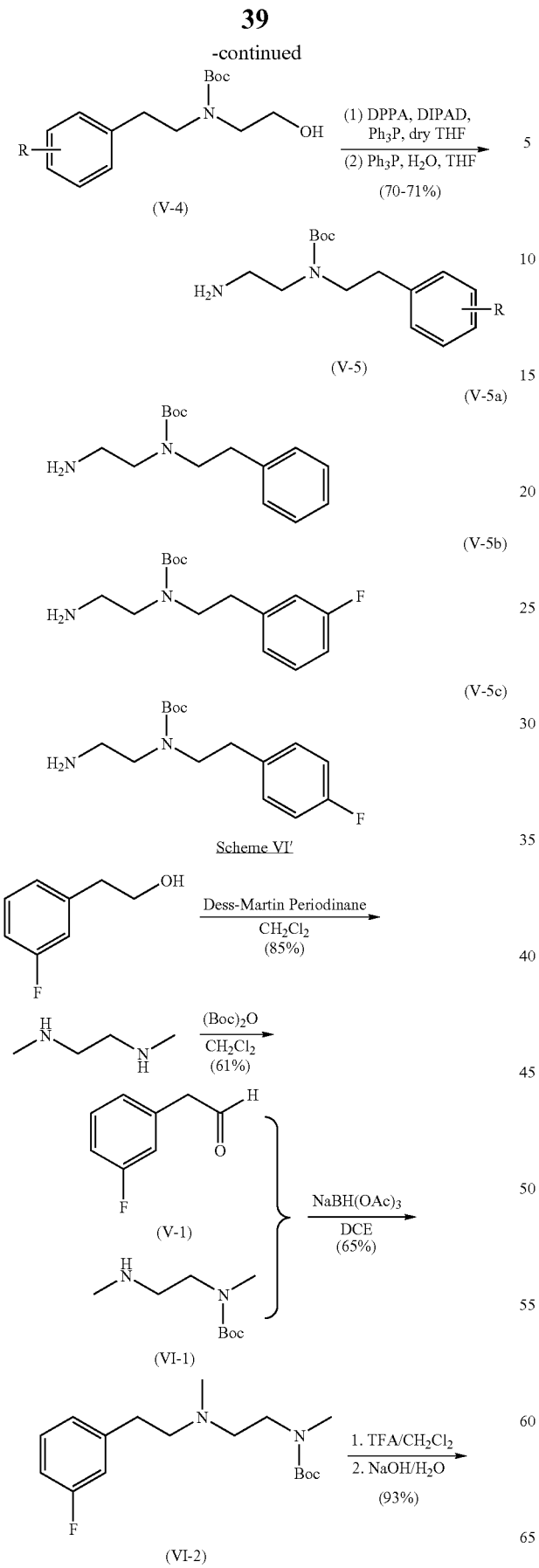

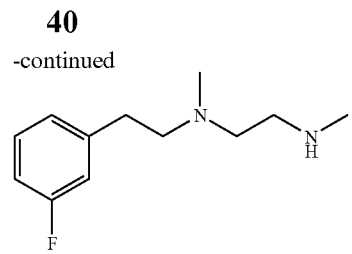

(VI-3)

Example 51

Synthesis of tert-butyl 4,6-dimethylpyridin-2-ylcarbamate (I-1)

A solution of 2-amino-4,6-dimethyl-pyridine (3.1 g, 0.025 mol) in melted tert-butanol (50 mL) was treated with di-tert-butyl dicarbonate (6.0 g, 0.0275 mol). The reaction mixture was stirred about 60° C. for 48 h, the solvent was evaporated in vacuo. The residue was purified directly by column chromatography (silica gel, Hexanes:EtOAc=8:2) to yield white solid (I-1, 4.8 g, 85%).

Example 52

Synthesis of tert-butyl 6-oxa-3-azabicyclo[3.1.0]hexane-3-carboxylate (I-2)

Di-tert-butyl dicarbonate (13.1 g, 0.06 mol) was added in portions to a solution of 3-pyrroline (2.1 g, 0.03 mol, 65% pure) in MeOH (120 mL) at 0° C. The reaction mixture was then stirred at room temperature for 24 h (TLC monitored using Hexanes:EtOAc=9:1). After evaporation of the solvent, the residue was dissolved in $CH_2Cl_2$ (120 mL). The reaction mixture was cooled to 0° C. and 3-chloroperoxybenzoic acid (MCPBA, 17.4 g, 0.078 mol, maximum 77% pure) was added in portions (5 times). After stirring the mixture at room temperature for 48 h, 20% $Na_2SO_3$ (80 mL) was added and two layers were separated. The aqueous layers were extracted with $CH_2Cl_2$ (80 mL×2). The combined organic extracts were washed with 20% $Na_2SO_3$ (60 mL×2) and water (50 mL). The solvent was then removed in vacuo. The residue was purified by column chromatography (silica gel, Hexanes: EtOAc=7:3) to yield colorless oil (I-2, 4.0 g, 71%).

Example 53

Synthesis of (±)-tert-butyl 3-{[6-(tert-butoxycarbonylamino)-4-methylpyridin-2-yl]methyl}-4-hydroxypyrrolidine-1-carboxylate (I-3a) and (±)-tert-butyl 3-{[2-(tert-butoxycarbonylamino)-6-methylpyridin-4-yl]methyl}-4-hydroxypyrrolidine-1-carboxylate (I-3b)

A solution of I-1 (1.2 g, 0.005 mol) in dry THF (20 mL) was cooled in a −78° C. bath (dry ice in acetone). n-BuLi (7.1 mL, 1.6 M in hexanes, 0.0125 mol) was added during 15 min under $N_2$ atmosphere. The color of the solution changed from colorless to orange. Then the cooling bath was removed. After 30 min stirring at room temperature, the color solution changed to dark red. The solution was then returned to the −78° C. bath. I-2 (1.2 g, 0.00625 mol) in dry THF (10 mL) was added during 1 h. After 1 h, the cooling bath was removed. The solution was stirred for 1 h more at room temperature. The reaction was quenched by the addition of ice-cold water (50 mL). The mixture was extracted with $CH_2Cl_2$ (30 mL×3). The combined organic layers were washed with brine and dried over anhydrous $MgSO_4$. The solvent was removed in vacuo and the residue was purified by column chromatography (silica gel, Hexanes:EtOAc=7:3) (1.1 g, 58%). Two geometrical isomers I-3a and I-3b can be totally separated by this eluent system ($R_f$: I-3a: 0.18, I-3b: 0.15). The molar ratio of I-3a and I-3b is 2:1. I-3a: white solid (0.79 g); I-3b: white solid (0.33 g).

Example 54

Synthesis of (±)-tert-butyl 3-{[6-(tert-butoxycarbonylamino)-4-methylpyridin-2-yl]methyl}-4-oxopyrrolidine-1-carboxylate (I-4)

To a suspension of Dess-Martin periodinane (0.5 g, 0.0012 mol) in dry $CH_2Cl_2$ (10 mL) was added a solution of I-3a (0.4 g, 0.001 mol) in dry $CH_2Cl_2$ (5 mL) via a cannula, and the reaction mixture was stirred at room temperature under $N_2$ atmosphere for 18 h. 1 M $Na_2S_2O_3$ (10 mL) was added to the reaction, and after stirring for 10 min, the reaction mixture was extracted with $CH_2Cl_2$ (10 mL×3). The combined organic layers were washed with 5% aqueous $NaHCO_3$ (10 mL×3) and brine (20 mL×1). The organic layer was dried over $Na_2SO_4$. The solvent was evaporated in vacuo. The residue was purified by column chromatography (silica gel, Hexanes: EtOAc, 8:2) to afford pale-yellow oil (I-4, 0.32 g, 78%).

Example 55

Synthesis of (±)-cis-tert-butyl 3-{2-(tert-butoxycarbonyl substituted alkylamino) ethylamino}-4-{[6-(tert-butoxycarbonylamino)-4-methylpyridin-2-yl]methyl}pyrrolidine-1-carboxylate (I-5a) and (±)-trans-tert-butyl 3-{2-(tert-butoxycarbonyl substituted alkylamino)ethylamino}-4-{[6-(tert-butoxycarbonylamino)-4-methylpyridin-2-yl]methyl}pyrrolidine-1-carboxylate (I-5b)

To a solution of I-4 (0.41 g, 0.001 mol), various amines $R_1NHR_2$ in Scheme I (0.0011 mol), such as tert-butyl 2-aminoethyl(4-chlorobenzyl)carbamate (0.31 g), acetic acid (0.09 g, 0.086 mL, 0.0015 mol), and 3 Å molecular sieves (1 g) in dry MeOH (10 mL) was added $NaBH_3CN$ (0.13 g, 0.002 mol). Then the reaction was stirred at room temperature under $N_2$ atmosphere for 36 h. The reaction mixture was then filtered through celite, and the celite pad was washed with $CH_3OH$ (10 mL×2). The filtrate was concentrated in vacuo. The residue was diluted with 1M NaOH (30 mL) and extracted with $CH_2Cl_2$ (20 mL×2). The organic layers were combined, washed with brine, dried over $MgSO_4$, and concentrated in vacuo of solvent to give crude product, which was purified by column chromatography (silica gel, Hexanes: EtOAc:$Et_3N$=9:1:0.25) to afford colorless oil (0.40 g, 60%). The cis and trans isomers can be separated with the above eluent ($R_f$: cis isomer: 0.30; trans isomer: 0.26). The molar ratio of cis and trans isomers was 45:55. I-5a, colorless oil (0.18 g). I-5b, colorless oil (0.22 g).

Example 56

Synthesis of (±)-cis-$N^1$-{-4'-[(6"-amino-4"-methylpyridin-2"-yl)methyl]pyrrolidin-3'-yl}-$N^2$-substituted alkyl ethane-1,2-diamine tetrahydrochloride (I-6a) and (±)-trans-$N^1$-{-4'-[(6"-amino-4"-methylpyridin-2"-yl)methyl]pyrrolidin-3'-yl}-$N^2$-substituted alkyl ethane-1,2-diamine tetrahydrochloride (I-6b)

I-5a or I-5b, such as cis-tert-butyl 3-(2-(tert-butoxycarbonyl(4-chlorobenzyl)amino)ethylamino)-4-((6-(tert-butoxycarbonylamino)-4-methylpyridin-2-yl)methyl)pyrrolidine-1-carboxylate (0.135 g, 0.0002 mol) or trans-tert-butyl 3-(2-(tert-butoxycarbonyl(4-chlorobenzyl)amino)ethylamino)-4-((6-(tert-butoxycarbonylamino)-4-methylpyridin-2-yl)methyl)pyrrolidine-1-carboxylate (0.135 g, 0.0002 mol) was cooled by an ice-water bath under argon. A solution of 4M HCl in 1,4-dioxane (4 mL) was then added slowly with stirring. The ice-water bath was removed after 3 h, and the reaction mixture was stirred at room temperature under argon atmosphere 34 h. The reaction mixture was concentrated in vacuo, and the residue was partitioned between water (10 mL) and ethyl acetate (10 mL). The aqueous layer was then washed with ethyl acetate (5 mL×2). After evaporation of water by high vacuum rotorvapor, the residue was dried by a lyophilizer to afford the I-6a: white solid (0.10 g) or I-6b: white solid (0.10 g).

Example 57

Synthesis of 2-(substituted benzylamino)-ethanol (II-1)

Substituted benzaldehyde (0.01 mol), such as 4-chloro benzaldehyde (1.4 g), was dissolved in dry ethanol (30 mL) and ethanolamine (0.61 g, 0.01 mol) was added. The reaction mixture was stirred overnight at 60° C. The ethanol was evaporated under reduced pressure to give a colorless oil. The oil was then dissolved in dry methanol (30 mL) and cooled in ice. Sodium borohydride ($NaBH_4$, 0.57 g, 0.015 mol) was added slowly in portions, and the resulting solution was left overnight at room temperature. The solvent was evaporated in vacuo, and the residue was dissolved in water, and extracted with $CH_2Cl_2$ (3×20 mL). The organic layers were combined and dried with $Na_2SO_4$, filtered and evaporated in vacuo to give colorless oily residue, which was purified by column chromatography (silica gel $CH_2Cl_2$:MeOH=9:1) to give 2-(4-chlorobenzylamino)-ethanol (II-1, 1.83 g, 99%).

Example 58

Synthesis of tert-butyl substituted benzyl(2-hydroxyethyl)carbamate (II-2)

A solution of di-tert-butyl dicarbonate (2.19 g, 0.01 mol) in $CH_2Cl_2$ (15 mL) was added dropwise to a solution of II-1 (0.01 mol), such as 2-(4-chlorobenzylamino)-ethanol (1.85 g) in 15 mL of $CH_2Cl_2$ and 12 mL of 1M NaOH. After stirring 24 h at room temperature, the organic layer was separated. The aqueous layer was extracted with $CH_2Cl_2$ (10 mL×2). The combined organic layers were washed with water (25 mL×2), dried over $Na_2SO_4$, evaporated in vacuo give crude product, which was purified by column chromatography (silica gel, Hexanes:EtOAc=7:3) to afford colorless oil (II-2, 2.86 g, quantitative yield).

Example 59

Synthesis of tert-butyl 2-aminoethyl(substituted benzyl)carbamate (II-3)

To a solution of triphenylphosphine ($Ph_3P$, 3.28 g, 0.0125 mol) in dry THF (10 mL) was added II-2 (0.01 mol), such as tert-butyl 4-chlorobenzyl(2-hydroxyethyl)carbamate (2.86 g), in dry THF (10 mL) at 0° C. under $N_2$ atmosphere via a cannula. Diisopropyl azodicarboxylate (DIAD, 2.63 g, 2.59 mL, 0.013 mol) was added dropwise, and the solution was stirred for 20 min at 0° C. Diphenylphosphoryl azide (DPPA, 3.44 g, 2.70 mL, 0.0125 mol) was added at 0° C., and the solution was stirred overnight at room temperature. The reaction mixture was then concentrated in vacuo. The crude residue was purified by column chromatography (silica gel, Hexanes:EtOAc=9.5:0.5) to yield colorless oil.

The above product was dissolved in THF (5 mL) and put into an ice-cold bath, $Ph_3P$ (3.15 g, 0.012 mol) and $H_2O$ (0.54 g, 0.03 mol) were added at 0° C. The reaction mixture was stirred 2 h at 0° C., and 21 h at room temperature. The solvent was evaporated in vacuo, and the residue was partitioned between water (10 mL) and $CH_2Cl_2$ (10 mL). The aqueous layer was extracted with $CH_2Cl_2$ (10 mL×2). The combined organic layers were dried over $MgSO_4$, and concentrated in vacuo. The residue was purified by column chromatography (silica gel, $CH_2Cl_2$:MeOH=9:1) to afford colorless oil (II-3, 1.71 g, 60%).

Example 60

The amines synthesized by the Scheme II are tert-butyl 2-aminoethyl(4-chlorobenzyl)carbamate (II-3a); tert-butyl 2-aminoethyl(3-chlorobenzyl)carbamate (II-3b); tert-butyl 2-aminoethyl[4-(trifluoromethyl)benzyl]carbamate (II-3c); tert-butyl 2-aminoethyl(4-fluorobenzyl)carbamate (II-3d); tert-butyl 2-aminoethyl[3-(trifluoromethyl)benzyl]carbamate (II-3e); tert-butyl 2-aminoethyl(3-methylbenzyl)carbamate (II-3f); tert-butyl 2-aminoethyl(3,4-dichlorobenzyl)carbamate (II-3g); tert-butyl 2-aminoethyl(2,4-dichlorobenzyl)carbamate (II-3h).

Example 61

Synthesis of (S)-2-(4-chlorobenzylamino)propan-1-ol (III-1)

4-Chloro-benzaldehyde (1.4 g, 0.01 mol) was dissolved in dry ethanol (30 mL) and (S)-(+)-2-amino-1-propanol (0.75 g, 0.01 mol) was added. The reaction mixture was stirred overnight at 60° C. The ethanol was evaporated under reduced pressure to give a colorless oil. The oil was then dissolved in dry methanol (30 mL) and cooled in ice. $NaBH_4$ (0.57 g, 0.015 mol) was added slowly in portions, and the resulting solution was left overnight at room temperature. The solvent was evaporated in vacuo, and the residue was dissolved in water, and extracted with $CH_2Cl_2$ (3×20 mL). The organic layers were combined and dried with $Na_2SO_4$, filtered and evaporated in vacuo to give colorless oily residue, which was purified by column chromatography (silica gel, $CH_2Cl_2$:MeOH, 9:1) to afford colorless oil (III-1, 1.85 g, 93%).

Example 62

The synthetic procedure for (S)-tert-butyl 4-chlorobenzyl (1-hydroxypropan-2-yl)carbamate (III-2) is the same as that for tert-butyl substituted benzyl(2-hydroxyethyl)carbamate (II-2) (quantitative yield).

Example 63

The synthetic procedure for (S)-tert-butyl 1-aminopropan-2-yl(4-chlorobenzyl) carbamate (III-3) is the same as that for tert-butyl 2-aminoethyl(substituted benzyl)carbamate (II-3) (68%).

Example 64

Synthesis of tert-butyl 4-chlorobenzyl(2-oxoethyl)carbamate (IV-1)

To a suspension of Dess-Martin periodinane (0.51 g, 0.0012 mol) in anhydrous $CH_2Cl_2$ (10 mL) was added a solution of tert-butyl 4-chlorobenzyl(2-hydroxyethyl)carbamate (II-2) (0.29 g, 0.001 mol) in anhydrous $CH_2Cl_2$ (5 mL). Then the reaction mixture was stirred at room temperature for 21 h under $N_2$ atmosphere. 1 M of $Na_2S_2O_3$ (10 mL) was added to the reaction mixture, and after stirring 10 min, the reaction mixture was extracted with $CH_2Cl_2$ (10 mL×3). The combined organic layers were washed with 5% aqueous $NaHCO_3$ (20 mL), and brine (20 mL). The organic layer was dried over $Na_2SO_4$, and evaporated in vacuo. The residue was then purified by column chromatography (silica gel, Hexanes:EtoAc=8:2) to afford colorless oil (IV-1, 0.20 g, 72%).

Example 65

Synthesis of tert-butyl 4-chlorobenzyl[2-(methylamino)ethyl]carbamate (IV-2)

To a solution of IV-1 (0.57 g, 0.002 mol) in MeOH (30 mL) was added $MeNH_2$ (2M in MeOH, 2 mL, 0.004 mol) at room temperature under $N_2$ atmosphere. The reaction mixture was heated at reflux for 6 h, and then cooled to −20° C. Then $NaBH_4$ (0.15 g, 0.004 mol) was added in portions. After stirred 1 h at −20° C., the reaction mixture was continued to stir 3 h at room temperature. The solvent was then evaporated under reduced pressure. The residue was dissolved in water (20 mL), and extracted with $CH_2Cl_2$ (20 mL×3). The combined organic layers were washed with brine, and dried over $MgSO_4$. The solvent was evaporated in vacuo, and the residue was purified by column chromatography (silica gel, $CH_2Cl_2$:MeOH=9:1) to afford colorless oil (VI-2, 0.59 g, 99%).

Example 66

Synthesis of 2-(substituted phenyl)-acetaldehyde (V-1)

To a suspension of Dess-Martin periodinane (2.04 g, 0.0048 mol) in anhydrous $CH_2Cl_2$ (50 mL) was added dropwise substituted phenethyl alcohol (0.004 mol), such as 3-fluorophenethyl alcohol (0.56 g, 0.5 mL). The reaction mixture was stirred at room temperature 16 h under $N_2$ atmosphere. 1M $Na_2S_2O_3$ (40 mL) was then added to the reaction mixture, and after stirring 15 min, the mixture was separated. The aqueous layer was extracted with $CH_2Cl_2$ (20 mL×2). The combined organic layers were washed with 5% $NaHCO_3$ (20 mL×2), and brine (10 mL), and dried over $Na_2SO_4$. The solvent was concentrated in vacuo. The residue was purified by column chromatography (silica gel, Hexanes:EtOAc=8:2) to afford pale-yellow volatile oil (V-1, 0.47 g, 85%).

Example 67

Synthesis of 2-[benzyl(substituted phenethyl)amino]ethanol (V-2)

A mixture of V-1 (0.003 mol), such as -[benzyl(3-fluorophenethyl) amino]ethanol (0.42 g), N-benzylethanolamine (0.5 g, 0.0033 mol), sodium triacetoxyborohydride [NaBH(OAc)$_3$, 0.90 g, 0.0042 mol] in dry 1, 2-dichloroethane (60 mL) was stirred at room temperature under N$_2$ atmosphere for 14 h. To the reaction mixture was then added 1M NaOH (40 mL). The organic layer was separated, and the aqueous layer was extracted with CH$_2$Cl$_2$ (30 mL×2). The combined organic layers were washed with brine (20 mL), and dried over MgSO$_4$. The solvent was concentrated in vacuo. The residue was purified by column chromatography (silica gel, Hexanes:EtOAc=6:4) to afford pale-yellow oil (V-2, 0.82 g, quantitative yield).

Example 68

Synthesis of 2-(3-fluorophenethylamino)ethanol (V-3)

A suspension of V-2 (0.003 mol), such as 2-[benzyl(3-fluorophenethyl)amino]ethanol (0.82 g), and 10% Palladium on activated carbon (Pd/C, 450 mg) in MeOH (30 mL) was stirred at room temperature under hydrogen atmosphere overnight. The catalyst was then filtered out through celite. The celite pad was washed with MeOH (10 mL×3). The filtrate was concentrated in vacuo. The residue was purified by column chromatography (silica gel, CH$_2$Cl$_2$:MeOH=8.5:1.5) to yield pale-yellow oil (V-3, 0.45 g, 82%).

Example 69

The synthetic procedure for tert-butyl substituted phenethyl(2-hydroxyethyl) carbamate (V-4) is the same as that for tert-butyl substituted benzyl(2-hydroxyethyl)carbamate (II-2) (quantitative yield).

Example 70

The synthetic procedure for tert-butyl 2-aminoethyl(substituted phenethyl)carbamate (V-5) is the same as that for tert-butyl 2-aminoethyl(substituted benzyl)carbamate (II-3) (70-71%). The amines synthesized by the Scheme V are tert-butyl 2-aminoethyl(phenethyl)carbamate (V-5a), tert-butyl 2-aminoethyl (3-fluorophenethyl)carbamate (V-5b), and tert-butyl 2-aminoethyl(4-fluorophenethyl)carbamate (V-5c).

Example 71

Synthesis of tert-butyl methyl[2-(methylamino)ethyl]carbamate (VI-1)

A solution of di-tert-butyl dicarbonate (2.18 g, 0.01 mol) in CH$_2$Cl$_2$ (120 mL) was added dropwise to a solution of N,N'-Dimethyl-ethane-1,2-diamine (1.76 g, 0.02 mol) in CH$_2$Cl$_2$ (40 mL) over 6 h with vigorous stirring. The reaction mixture was continued to stir for a further 18 h at room temperature. Then the solvent was concentrated in vacuo to give an oily residue, which was dissolved in 60 mL of 2M Na$_2$CO$_3$ aqueous solution, and extracted with CH$_2$Cl$_2$ (30 mL×2). The combined organic layers were washed with 2M Na$_2$CO$_3$ (30 mL×2), and dried over anhydrous MgSO$_4$. The solvent was evaporated in vacuo to yield the product, which was purified by column chromatography (silica gel, CH$_2$Cl$_2$:MeOH, 9:1) to afford colorless oil (VI-1, 1.15 g, 61%)

Example 72

Synthesis of tert-butyl 2-[(3-fluorophenethyl)(methyl)amino]ethyl(methyl) carbamate (VI-2)

A mixture of (VI-1) (0.94 g, 0.005 mol), 3-fluoro-phenylacetaldehyde (0.76 g, 0.0055 mol), and NaBH(OAc)$_3$ (1.48 g, 0.007 mol) in dry 1,2-dichloroethane (50 mL) was stirred overnight at room temperature under N$_2$ atmosphere. To the reaction mixture was added 1M NaOH (30 mL), and then the mixture was extracted with CH$_2$Cl$_2$ (30 mL×3). The combined organic layers were washed with brine, and dried over MgSO$_4$. The solvent was then evaporated in vacuo to generate the product, which was purified by column chromatography (silica gel, Hexanes:EtOAc=5:5) to afford colorless oil (VI-2, 1.0 g, 65%).

Example 73

Synthesis of N$^1$-(3-fluorophenethyl)-N$^1$,N$^2$-dimethylethane-1,2-diamine (VI-3)

To a mixture of (VI-2) (0.93 g, 0.003 mol) in anhydrous CH$_2$Cl$_2$ (4.5 mL) was added TFA (4.5 mL) at 0° C. The reaction mixture was stirred 1 h at 0° C., and 1 h at room temperature. After the reaction was done, 2M NaOH aqueous solution (30 mL) was added to adjust pH value to basic. The mixture was continued to stir 10 min. The organic layer was separated. The aqueous layer was extracted with CH$_2$Cl$_2$ (30 mL×2). The combined organic layers were washed with 2M NaOH (30 mL×2). The solvent was evaporated in vacuo. The residue was purified by column chromatography (silica gel, CH$_2$Cl$_2$:MeOH:Et$_3$N=9.75:0.25:0.25) to afford colorless oil (VI-3, 0.59 g, 93%).

Example 74

Figure 7:
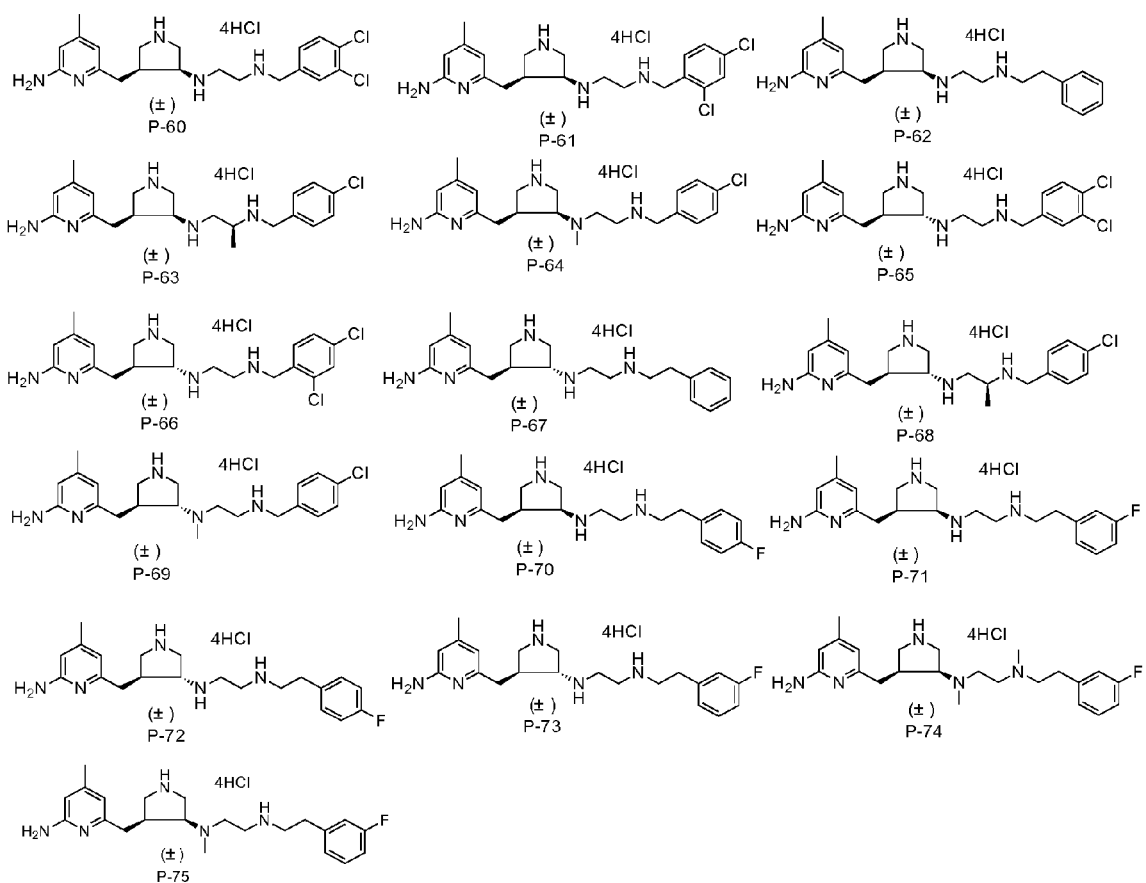
FIGS. 7 and 8 provide several 4-methylpyridine derivatives of compounds P-46 and P-47, as shown in FIG. 6.

Various other compounds, including those of FIG. 7, were prepared in accordance with the synthetic routes of Scheme 1'-VI'. All the chemical structures were confirmed by $^1$H NMR, $^{13}$CNMR, and mass spectra. All of the products are racemic mixtures.

Examples 75 and 76 can be considered in conjunction with Scheme VII', below. Compound P-69 and P-75 and its analogues can be synthesized by Scheme VII'. Each of the phenyl groups of compounds I-5 in Scheme VII' can be, alternatively, substituted at any of the para, meta or ortho positions with substituents including but not limited to halogen, alkyl or halogenated alkyl. Likewise, via such amines and reductive amination of an oxapyrrolidinyl intermediate, any of the phenyl groups of the compounds of FIG. 7 can be substituted.

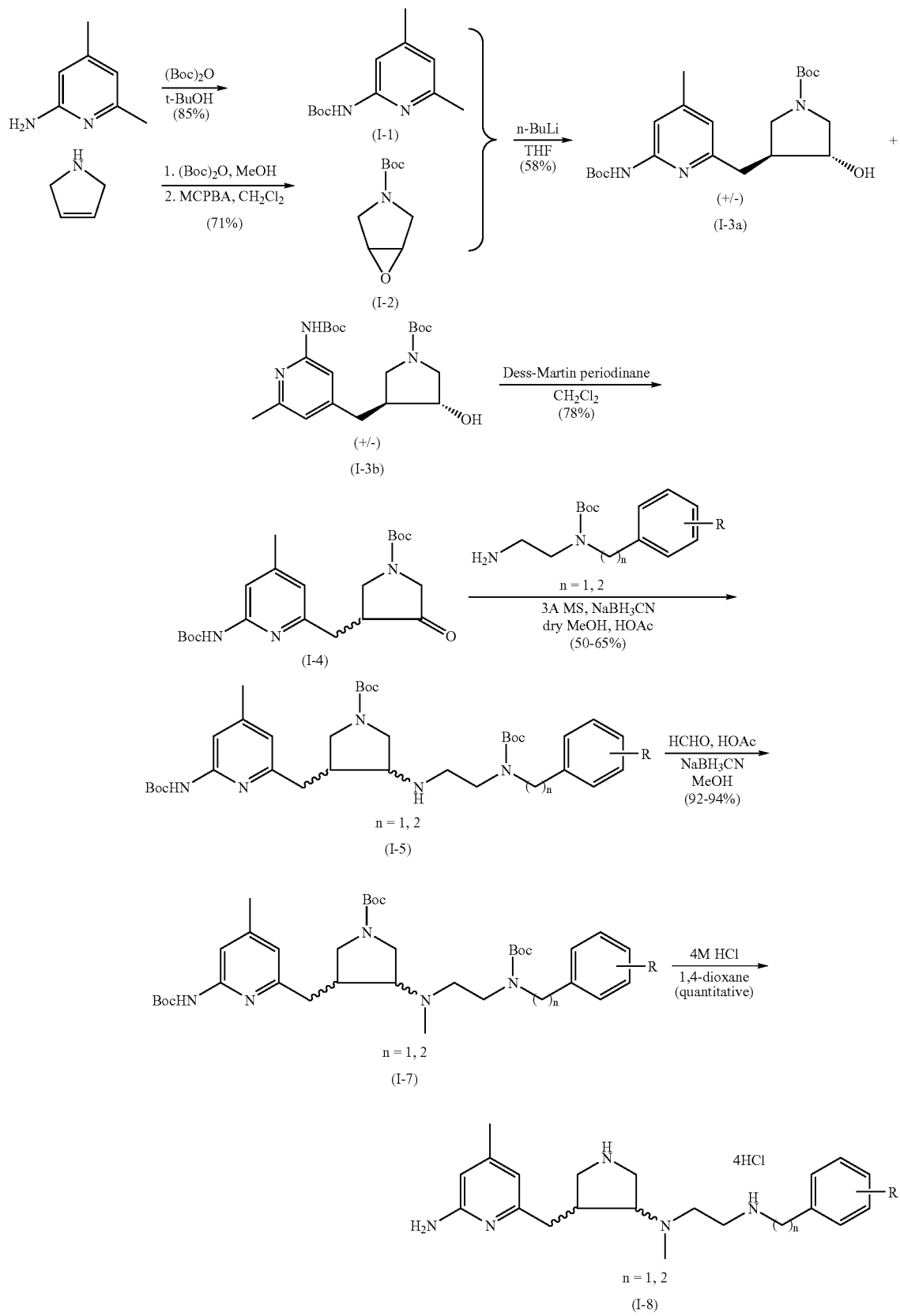

Example 75

Synthesis of (±)-cis-tert-butyl 3-{{2-[tert-butoxycarbonyl (substituted benzyl)amino]ethyl}(methyl)amino}-4-{[6-(tert-butoxycarbonylamino)-4-methylpyridin-2-yl] methyl}pyrrolidine-1-carboxylate (n=1, R=4-Cl) or (±)-cis-tert-butyl 3-{{2-[tert-butoxycarbonyl(substituted phenethyl) amino]ethyl}(methyl)amino}-4-{[6-(tert-butoxycarbonylamino)-4-methylpyridin-2-yl] methyl}pyrrolidine-1-carboxylate (n=2, R=3-F).

To a solution of (±)-cis-tert-butyl 3-{2-[tert-butoxycarbonyl(substituted benzyl)amino]ethylamino}-4-{[6-(tert-butoxycarbonylamino)-4-methylpyridin-2-yl] methyl}pyrrolidine-1-carboxylate (I-4, n=1) (0.001 mol), such as (±)-cis-tert-butyl 3-{2-[tert-butoxycarbonyl(4-chlorobenzyl)amino]ethylamino}-4-{[6-(tert-butoxycarbonylamino)-4-methylpyridin-2-yl]methyl}pyrrolidine-1-carboxylate (n=1, R=4-Cl) (0.67 g), or (±)-cis-tert-butyl 3-{2-[tert-butoxycarbonyl(substituted phenethyl)amino] ethylamino}-4-{[6-(tert-butoxycarbonylamino)-4-methylpyridin-2-yl]methyl}pyrrolidine-1-carboxylate (I-4, n=2) (0.001 mol), such as (±)-cis-tert-butyl 3-{2-[tert-butoxycarbonyl(3-fluorophenethyl)amino]ethylamino}-4-{[6-(tert-butoxycarbonylamino)-4-methylpyridin-2-yl] methyl}pyrrolidine-1-carboxylate (n=2, R 4-F) (0.67 g), dissolved in MeOH (20 mL) at 0° C. were added a 37% formaldehyde solution (0.81 g, 0.75 mL, 0.010 mol), NaBH$_3$CN (0.31 g, 0.005 mol), and acetic acid (0.12 g, 0.12 mL, 0.002 mol). The reaction mixture was then stirred at room temperature overnight. The solvent was removed under reduced pressure. The residue was dissolved in water, extracted with CH$_2$Cl$_2$ (15 mL×3). The combined organic layers were dried over MgSO$_4$, and evaporated in vacuo. The residue was purified by column chromatography (silica gel, Hexanes:EtOAc, 6:4) to generate (±)-cis-tert-butyl 3-{{2-tert-butoxycarbonyl(4-chlorobenzyl)amino]ethyl}(methyl) amino}-4-{[6-(tert-butoxycarbonylamino)-4-methylpyridin-2-yl]methyl}pyrrolidine-1-carboxylate (n=1, R=4-Cl) as colorless oil (0.65 g, 94%), or (±)-cis-tert-butyl 3-{{2-[tert-butoxycarbonyl(3-fluorophenethyl)amino]ethyl}(methyl) amino}-4-{[6-(tert-butoxycarbonylamino)-4-methylpyridin-2-yl]methyl}pyrrolidine-1-carboxylate as colorless oil (0.63 g, 92%).

Example 76

The synthetic procedure of (±)-N$^1$-{cis-4-[(6-amino-4-methylpyridin-2-yl)methyl]-1-methylpyrrolidin-3-yl}-N$^2$-(substituted benzyl)-N$^1$-methylethane-1,2-diamine tetrahydrochloride (n=1) (I-8) or of (±)-N$^1$-{(3S,4S)-4-[(6-amino-4-methylpyridin-2-yl)methyl]pyrrolidin-3-yl}-N$^2$-(substituted phenethyl)-N$^1$-methylethane-1,2-diamine tetrahydrochloride (n=2) (I-8) is the same as that for (±)-cis-N$^1$-{-4'-[(6"-amino-4"-methylpyridin-2"-yl)methyl]pyrrolidin-3'-yl}-N$^2$-substituted alkyl ethane-1,2-diamine tetrahydrochloride (I-6a) (quantitative yield).

Figure 8:
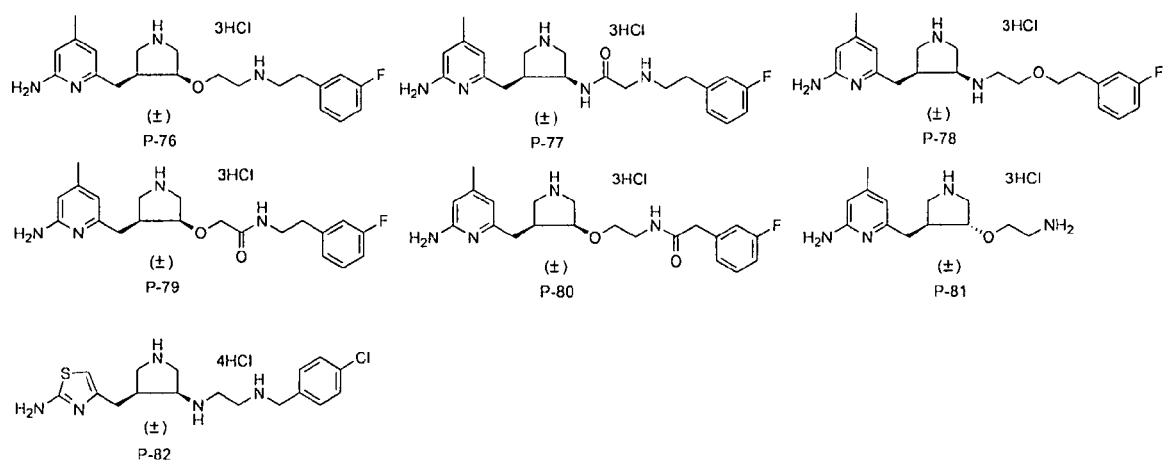
Figure 9:
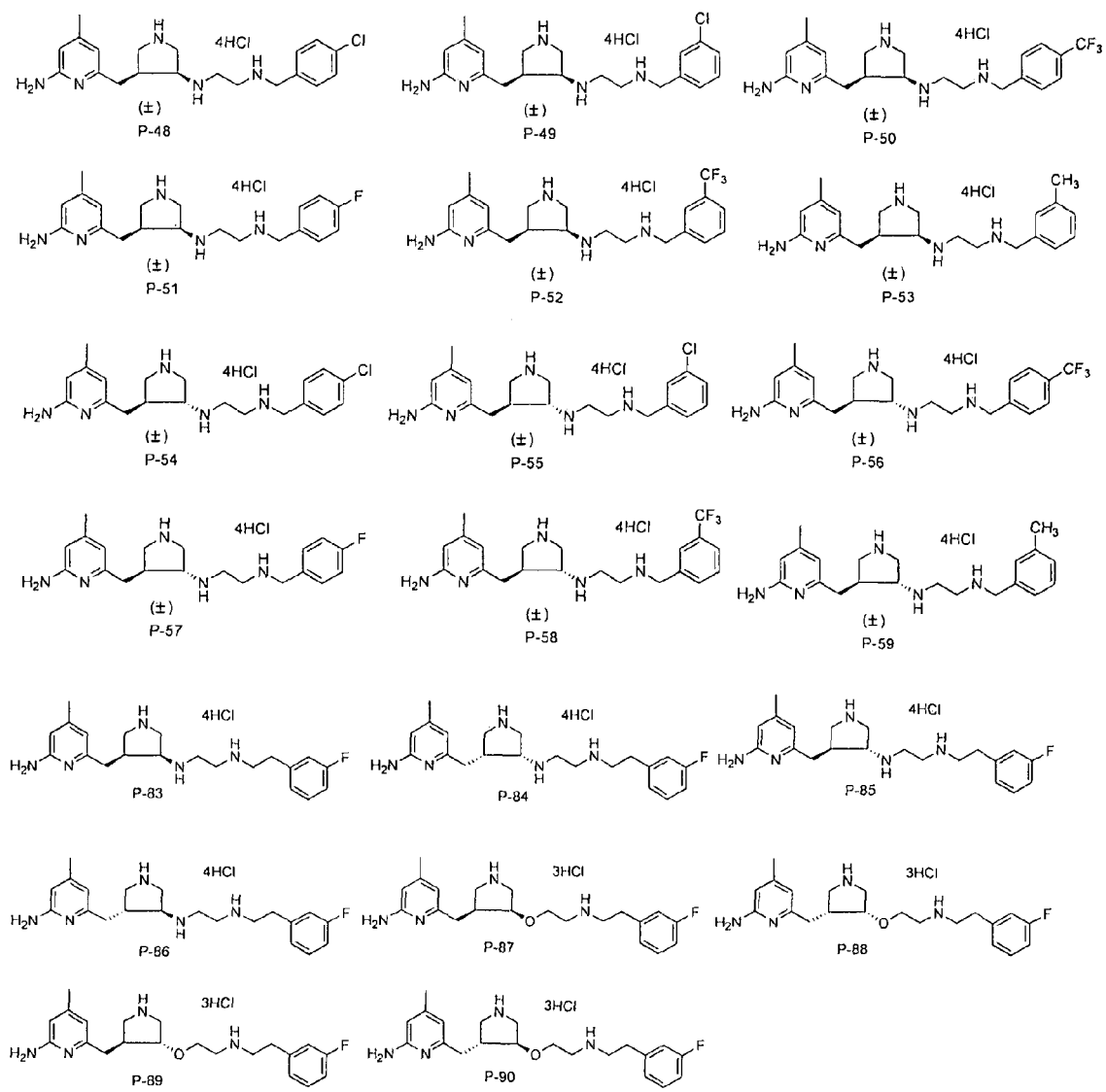
FIG. 9 provides the enantiopure isomers of compounds P-71, P-73, P-76 and the trans isomer of P-76.

Various other compounds, including those of FIG. 8, were prepared in accordance with the synthetic routes of Schemes VIII'-XII'. All the chemical structures were confirmed by $^1$H NMR, $^{13}$CNMR, and mass spectra. All of the products are racemic mixtures.

Examples 77-85 can be considered in conjunction with Scheme VIII' below. The phenyl groups of compounds P-76 in Scheme VIII' can be, alternatively, substituted at any of the para, meta or ortho positions with substituents including but not limited to halogen, alkyl or halogenated alkyl. Likewise, via such reactions showed in Scheme VIII', the phenyl groups of the compounds of FIG. 8 can be substituted.

Scheme VIII'

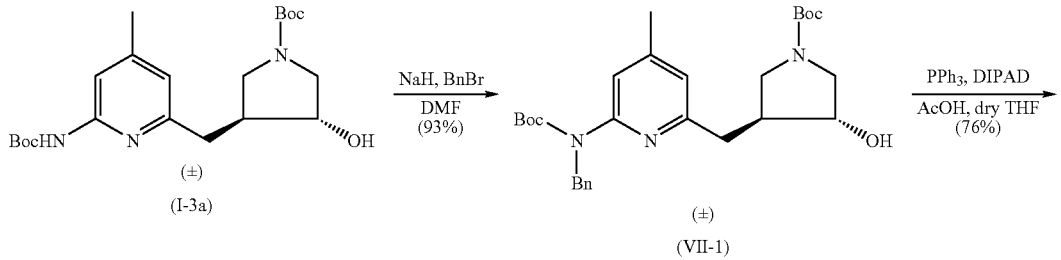

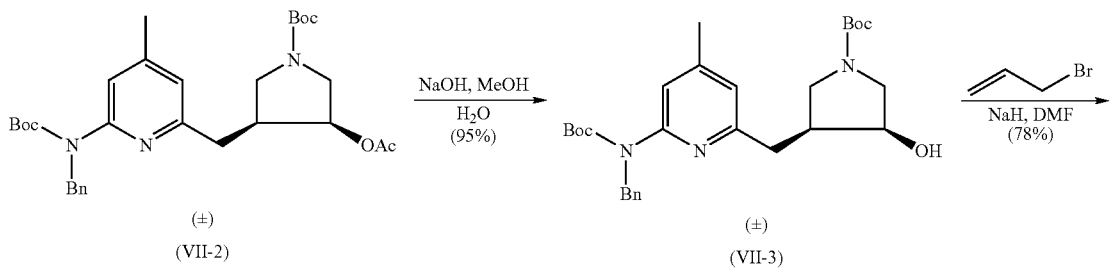

-continued
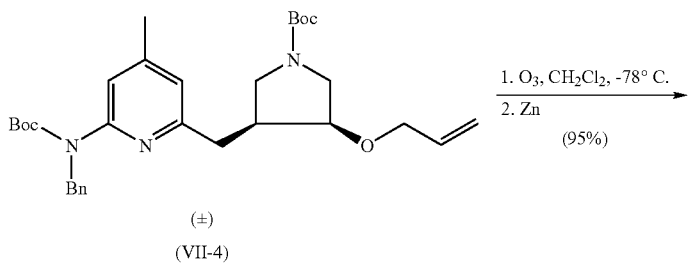
(±)
(VII-4)
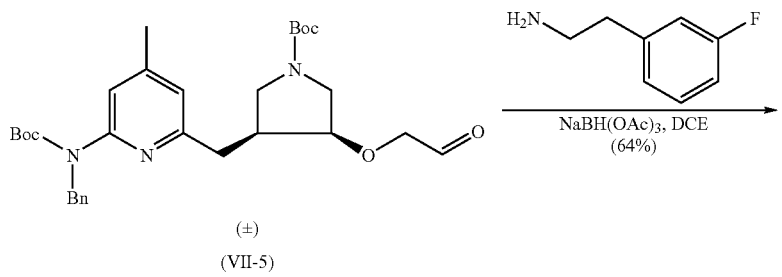
(±)
(VII-5)
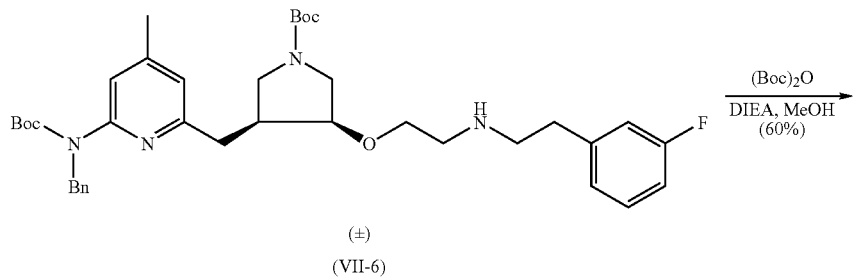
(±)
(VII-6)
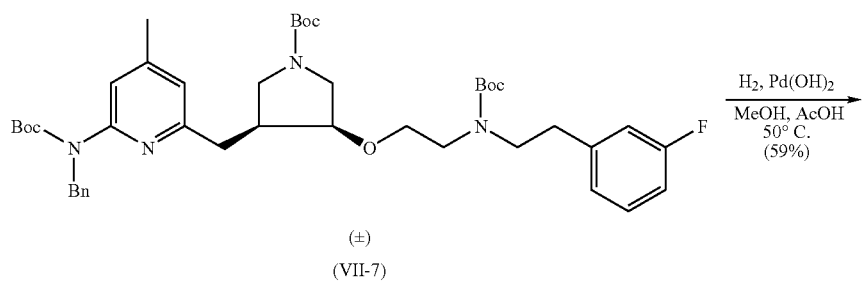
(±)
(VII-7)
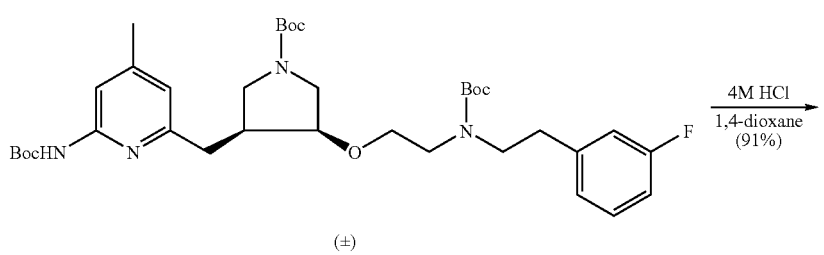
(±)
(VII-8)
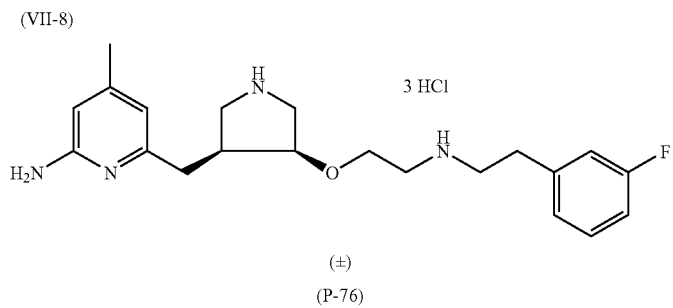
(±)
(P-76)

Example 77

Synthesis of (±)-cis-tert-butyl 3-{{6-[benzyl(tert-butoxycarbonyl)amino]-4-methylpyridin-2-yl}methyl}-4-hydroxypyrrolidine-1-carboxylate (VII-1)

To a flame-dried flask containing a solution of sodium hydride (NaH, 0.04 g, 0.001 mol) in dry DMF (5 mL) at 0° C. was added dropwise a solution of I -3a (0.5 g, 0.001 mol) in dry DMF (5 mL) via cannula. The solution was stirred at 0° C. for 15 min. Benzyl bromide (0.13 g, 0.095 mL, 0.0011 mol) was added dropwise, and the reaction mixture was stirred at room temperature overnight. The solvent was removed under reduced pressure. The residue was dissolved in water and extracted with EtOAc (15 mL×3). The combined organic layers were dried over $Na_2SO_4$, and concentrated in vacuo. The residue was purified by column chromatography (silica gel, hexanes:EtOAc 6:4) to generate colorless oil (VII-1, 0.5 g, 93%).

Example 78

Synthesis of (±)-cis-tert-butyl 3-acetoxy-4-{{6-[benzyl(tert-butoxycarbonyl)amino]-4-methylpyridin-2-yl}methyl}pyrrolidine-1-carboxylate (VII-2)

A solution of (VII-1) (0.4 g, 0.0008 mol) in dry THF (10 mL) was added to a flame dried flask containing $Ph_3P$ (0.26 g, 0.001 mol) under $N_2$ atmosphere. Acetic acid (HOAc, 0.09 g, 0.086 mL, 0.0015 mol) and DIAD (0.20 g, 0.20 mL, 0.001 mol) were added and the mixture was stirred at room temperature overnight. The solvent was removed under reduced pressure. The residue was purified by column chromatography (silica gel, hexanes:EtOAc=4:1) to generate a colorless oil (VII-2, 0.33 g, 76%).

Example 79

Synthesis of (±)-cis-tert-butyl 3-{{6-[benzyl(tert-butoxycarbonyl)amino]-4-methylpyridin-2-yl}methyl}-4-hydroxypyrrolidine-1-carboxylate (VII-3)

To a solution of VII-2 (0.32 g, 0.0006 mol) in MeOH (3 mL) was added 1 M NaOH (3 mL). The mixture was stirred at room temperature overnight. The mixture was acidified to pH=7 with 1M HCl and extracted with EtOAc (15 mL×3). The combined organic layers were dried over $Na_2SO_4$, and concentrated in vacuo. The residue was purified by column chromatography (silica gel, hexanes:EtOAc=6:4) to generate a colorless oil (VII-3, 0.28 g, 95%).

Example 80

Synthesis of (±) cis-tert-butyl 3-(allyloxy)-4-{{6-[benzyl(tert-butoxycarbonyl)amino]-4-methylpyridin-2-yl}methyl}pyrrolidine-1-carboxylate (VII-4)

To a flame-dried flask containing a solution of NaH (0.044 g, 0.0011 mol) in dry DMF (5 mL) at 0° C. was added dropwise a solution of VII-3 (0.5 g, 0.001 mol) in dry DMF (5 mL) via cannula. The solution was stirred at 0° C. for 15 min. Allyl bromide (0.15 g, 0.10 mL, 0.0012 mol) was added dropwise and the reaction mixture was stirred at room temperature overnight. The solvent was removed under reduced pressure. The residue was dissolved in water and extracted with EtOAc (15 mL×3). The combined organic layers were dried over $Na_2SO_4$, and evaporated in vacuo. The residue was purified by column chromatography (silica gel, hexanes:EtOAc=4:1) to generate a colorless oil (VII-4, 0.42 g, 78%).

Example 81

Synthesis of (±)-cis-tert-butyl 3-{{6-[benzyl(tert-butoxycarbonyl)amino]-4-methylpyridin-2-yl}methyl}-4-(2-oxoethoxy)pyrrolidine-1-carboxylate (VII-5)

A solution of VII-4 (0.40 g, 0.00075 mol) in $CH_2Cl_2$ (5 mL) was cooled to −78° C. Ozone was bubbled through the solution for 1 h. Zinc dust (0.13 g, 0.002 mol) and a 50% acetic acid aqueous solution (5 mL) were added, and the mixture was allowed to warm to room temperature and stirred for a further 2 h. The mixture was transferred to a separatory funnel and washed with saturated $NaHCO_3$ solution (15 mL×2). The aqueous layers were back-extracted with $CH_2Cl_2$ (10 mL×2). The organic layers were combined, dried over $Na_2SO_4$ and concentrated in vacuo. The residue was purified by column chromatography (silica gel, hexanes:EtOAc=1:1) to generate a pale-yellow oil (VII-5, 0.38 g, 95%).

Example 82

Synthesis of (±) cis-tert-butyl 3-{{6-[benzyl(tert-butoxycarbonyl)amino]-4-methylpyridin-2-yl}methyl}-4-[2-(3-fluorophenethylamino)ethoxy]pyrrolidine-1-carboxylate (VII-6)

To a solution of VII-5 (0.40 g, 0.00075 mol) in dry dichloroethane (DCE, 5 mL) was added 3-fluorophenethylamine (0.0016 mol) under a $N_2$ atmosphere. The reaction mixture was stirred at room temperature for 30 min before $NaBH(OAc)_3$ (0.21 g, 0.001 mol) was added. The mixture was stirred for 2 h, then poured into saturated $K_2CO_3$ aqueous solution (15 mL). The aqueous layer was extracted with $CH_2Cl_2$ (15 mL×3), and the organic layers were combined, dried over $Na_2SO_4$ and concentrated in vacuo. The residue was purified by column chromatography (silica gel, MeOH:EtOAc=1:9) to generate a pale-yellow oil (VII-6, 0.32 g, 64%).

Example 83

Synthesis of (±) cis-tert-butyl 3-{{6-[benzyl(tert-butoxycarbonyl)amino]-4-methylpyridin-2-yl}methyl}-4-{2-[tert-butoxycarbonyl(3-fluorophenethyl)amino]ethoxy}pyrrolidine-1-carboxylate (VII-7)

To a solution of VII-6 (0.26 g, 0.0004 mol) in MeOH (10 mL) was added to N,N-diisopropylethylamine (DIEA, 0.2 mL) and di-tert-butyl dicarbonate (0.22 g, 0.001 mol). The reaction mixture was stirred at room temperature for 4 h. The solvent was evaporated in vacuo, the residue was purified by column chromatography (silica gel, Hexanes:EtOAc=3:1) to generate a colorless oil (VII-7, 0.183 g, 60%)

Example 84

Synthesis of (±) cis-tert-butyl 3-{2-[tert-butoxycarbonyl(3-fluorophenethyl)amino]ethoxy}-4-{[6-(tert-butoxycarbonylamino)-4-methylpyridin-2-yl]methyl}pyrrolidine-1-carboxylate (VII-8)

To a solution of VII-6 (0.15 g, 0.0002 mol) in MeOH (3 mL) and AcOH (1 mL) was added Pd(OH)₂ on activated C (60 mg). The mixture was stirred under 1 atm H₂ at 50° C. overnight. The mixture was diluted with CH₂Cl₂ and filtered through Celite, then added to a saturated NaHCO₃ aqueous solution (15 mL). The aqueous layer was extracted with CH₂Cl₂ (15 mL×3), and the organics were combined, dried over Na₂SO₄ and concentrated in vacuo. The residue was purified by column chromatography (silica gel, hexanes:EtOAc=7:3) to generate a colorless oil (VII-8, 0.08 g, 59%).

Example 85

The synthetic procedure of (±)-6-{{cis-4-[2-(3-fluorophenethylamino)ethoxy]pyrrolidin-3-yl}methyl}-4-methylpyridin-2-amine trihydrochloride (P-76) is the same as that of (±)-cis-N¹-{-4'-[(6"-amino-4"-methylpyridin-2"-yl)methyl]pyrrolidin-3'-yl}-N²-substituted alkyl ethane-1,2-diamine tetrahydrochloride (I-6a) (91%)

Examples 86-91 can be considered in conjunction with Scheme IX' below. The phenyl groups of compounds P-77 in Scheme IX' can be, alternatively, substituted at any of the para, meta or ortho positions with substituents including but not limited to halogen, alkyl or halogenated alkyl. Likewise, via such reactions showed in Scheme IX', the phenyl groups of the compounds of FIG. 8 can be substituted.

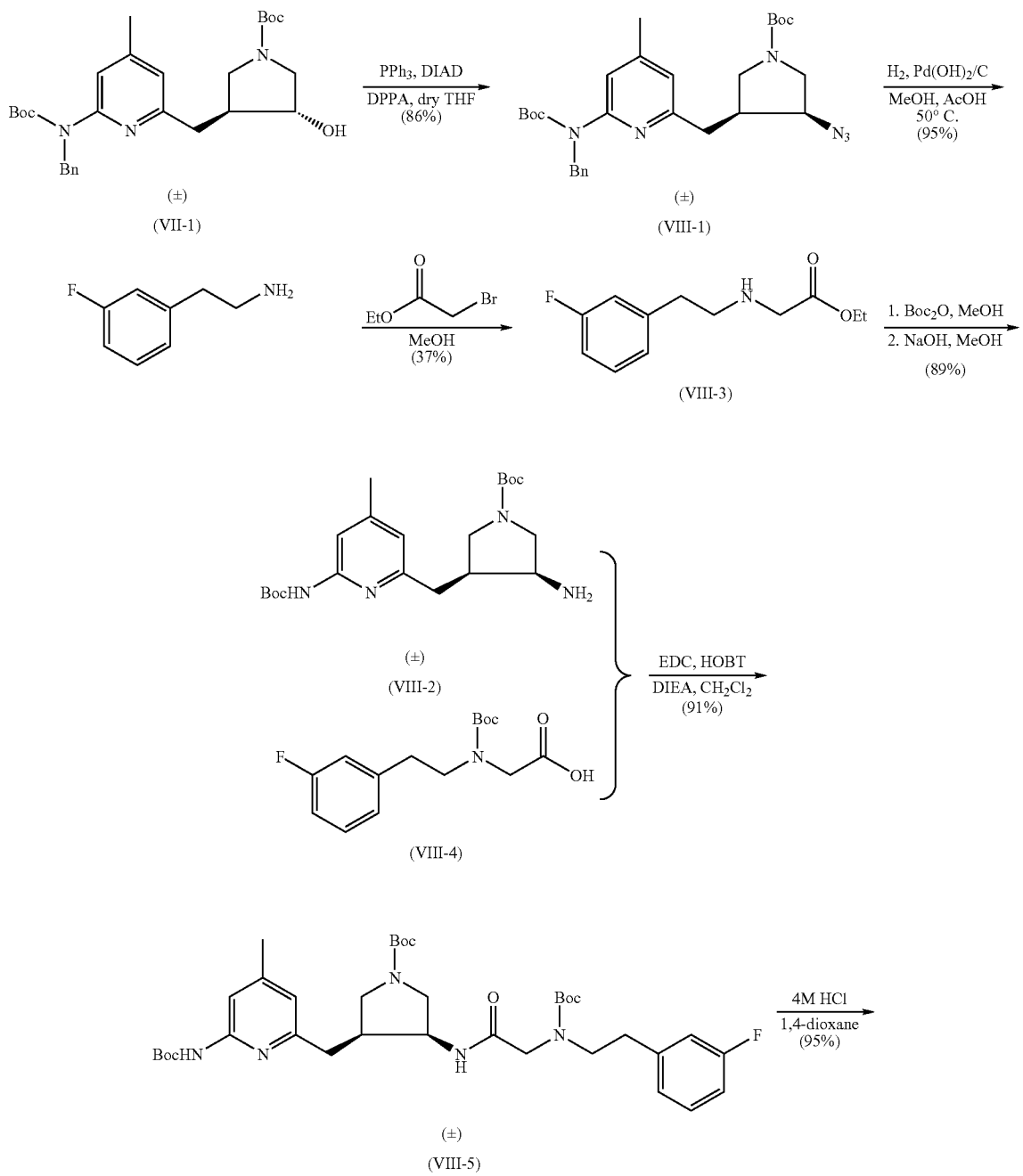

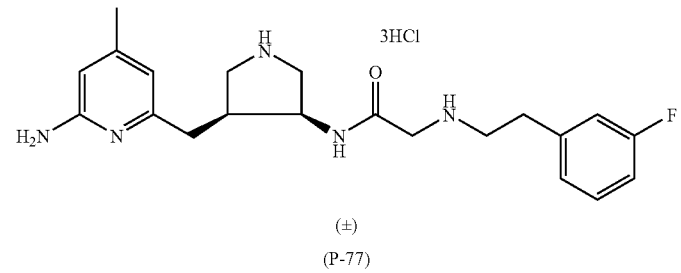

(±)
(P-77)

Example 86

Synthesis of (±) cis-tert-butyl 3-azido-4-{{6-[benzyl(tert-butoxycarbonyl)amino]-4-methylpyridin-2-yl}methyl}pyrrolidine-1-carboxylate (VIII-1)

A solution of VII-1 (0.40 g, 0.0008 mol) in dry THF (5 mL) was added to a flame-dried flask containing Ph$_3$P (0.26 g, 0:001 mol) and DIAD (0.20 g, 0.20 mL, 0.001 mol) in dry THF (5 mL). DPPA (0.41 g, 0.32 mL, 0.0015 mol) was added. The reaction mixture was stirred at room temperature overnight. The solvent was removed under reduced pressure. The residue was purified by column chromatography (silica gel, hexanes:EtOAc=5:1) to generate a colorless oil (VIII-1, 0.36 g, 86%).

Example 87

The synthetic procedure of (±) cis-tert-butyl 3-amino-4-{[6-(tert-butoxycarbonylamino)-4-methylpyridin-2-yl]methyl}pyrrolidine-1-carboxylate (VIII-2) was the same as that of (±) cis-tert-butyl 3-{2-[tert-butoxycarbonyl(3-fluorophenethyl)amino]ethoxy}-4-{[6-(tert-butoxycarbonylamino)-4-methylpyridin-2-yl]methyl}pyrrolidine-1-carboxylate (VII-8) (95%).

Example 88

Synthesis of ethyl 2-(3-fluorophenethylamino)acetate (VIII-3).

Ethyl bromoacetate (0.166 g, 0.11 mL, 0.001 mol) and 3-fluorophenethylamine (0.139 g, 0.13 mL, 0.001 mol) were stirred in MeOH (10 mL) for 48 h. The solvent was removed in vacuo, and the residue was purified by column chromatography (silica gel, hexanes:EtOAc=2:3) to generate VIII-3 (0.083 g, 37%).

Example 89

Synthesis of 2-(tert-butoxycarbonyl(3-fluorophenethyl)amino)acetic acid (VIII-4).

To a solution of VIII-3 (0.13 g, 0.0005 mol) in MeOH (10 mL) was added di-tert-butyl dicarbonate (0.11 g, 0.00075 mol). The mixture was stirred at room temperature for 4 h. TLC monitored the completion of the reaction. The solvent was evaporated in vacuo to afford oily residue. The residue was dissolved in MeOH (2 mL), and 1 M NaOH (5 mL) was added. The reaction mixture was stirred 20 h at room temperature. After the reaction was completed, the reaction mixture was poured into 2 M HCl (10 mL) and extracted with EtOAc (15 mL×3). The combined organic layers were dried over Na$_2$SO$_4$, and concentrated in vacuo. The residue was purified by column chromatography (silica gel, 100% EtOAc) to afford the pure product (VIII-4, 0.13 g, 89%)

Example 90

Synthesis of (±) cis-tert-butyl 3-{2-[tert-butoxycarbonyl(3-fluorophenethyl)amino]acetamido}-4-{[6-(tert-butoxycarbonylamino)-4-methylpyridin-2-yl]methyl}pyrrolidine-1-carboxylate (VIII-5)

To a solution of VIII-4 (0.104 g, 0.000256 mol) in dry Cl$_2$Cl$_2$ (3 mL) was added N-ethyl-N'-(3-dimethylaminopropyl)carbodiimide (EDC, 0.043 g, 0.050 mL, 0.00028 mol), 1-hydroxybenzotriazole (HOBt, 0.038 g, 0.00028 mol) and DIEA (0.036 g, 0.052 mL, 0.00028 mol). To this mixture was added a solution of VIII-2 (0.10 g, 0.000252 mol) in dry CH$_2$Cl$_2$ (3 mL). The mixture was stirred overnight. The mixture was diluted with CH$_2$Cl$_2$ (10 mL) and washed with 1 M HCl (15 mL×2), saturated NaHCO$_3$ aqueous solution (15 mL×2), and brine (15 mL), dried over Na$_2$SO$_4$ and concentrated in vacuo. The residue was purified by column chromatography (silica gel, hexanes:EtOAc=1:1) to generate the pure product (VIII-5, 0.17 g, 91%)

Example 91

The synthetic procedure of (±)-N-{cis-4-[(6-amino-4-methylpyridin-2-yl)methyl]pyrrolidin-3-yl}-2-(3-fluorophenethylamino)acetamide trihydrochloride (P-77) is the same as that of (±)-cis-N$^1$-{4'-[(6''-amino-4''-methylpyridin-2''-yl)methyl]pyrrolidin-3'-yl}-N$^2$-substituted alkyl ethane-1,2-diamine tetrahydrochloride (I-6a) (95%)

Examples 92-95 can be considered in conjunction with Scheme X' below. The phenyl groups of compounds P-78 in Scheme X' can be, alternatively, substituted at any of the para, meta or ortho positions with substituents including but not limited to halogen, alkyl or halogenated alkyl. Likewise, via such reactions showed in Scheme X', the phenyl groups of the compounds of FIG. 8 can be substituted.

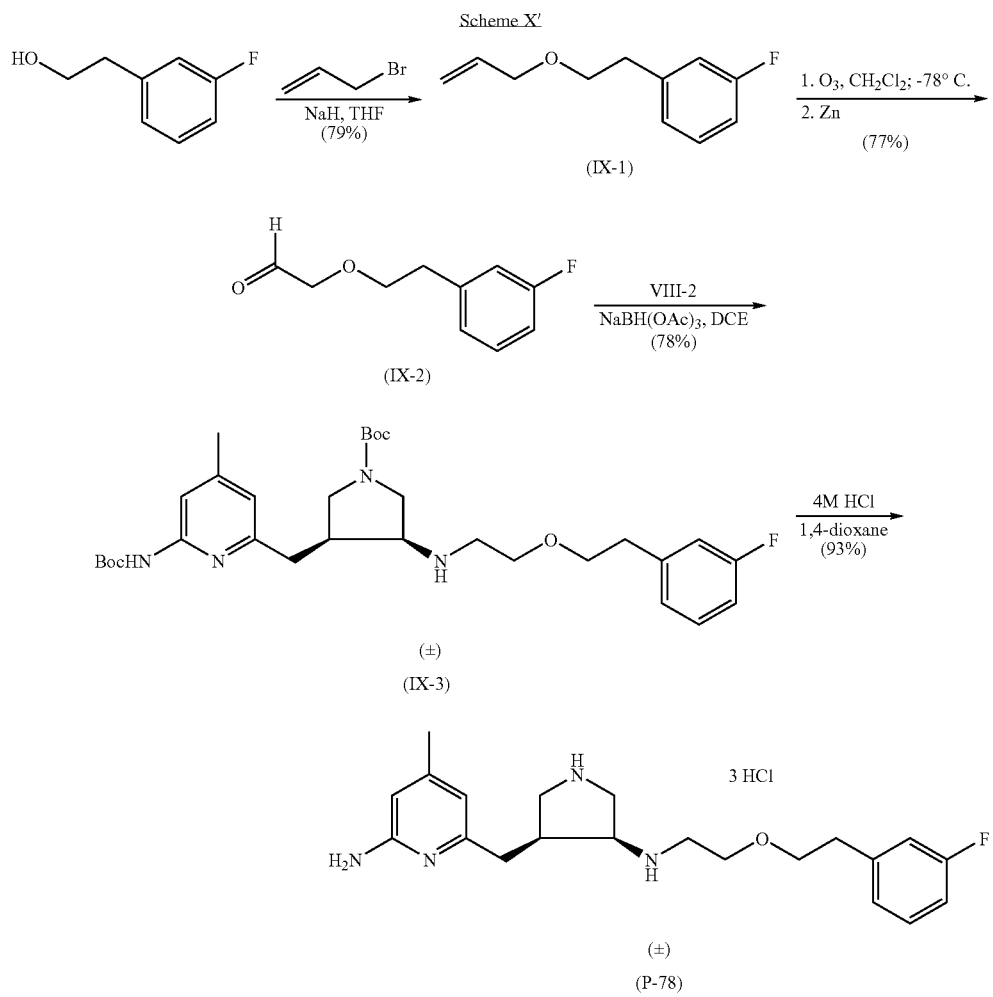

Example 92

The synthetic procedure of 1-(2-(allyloxy)ethyl)-3-fluorobenzene (IX-1) was analogous to that of VII-4, except that dry THF was used as the solvent (79%).

Example 93

The synthetic procedure of 2-(3-fluorophenethoxy)acetaldehyde (IX-2) was the same as that of VII-5 (77%).

Example 94

Synthesis of (±)-cis-tert-butyl 3-{[6-(tert-butoxycarbonylamino)-4-methylpyridin-2-yl]methyl}-4-[2-(3-fluorophenethoxy)ethylamino]pyrrolidine-1-carboxylate (IX-3).

A solution of IX-2 (0.027 g, 0.00015 mol) in dry DCE (1 mL) was added to a solution of VIII-2 (0.069 g, 0.00017 mol) in dry DCE (5 mL). The reaction mixture was stirred for 15 min at room temperature. NaBH(OAc)$_3$ (0.042 g, 0.0002 mol) was added, and the mixture was stirred for a further 2 h, then poured into saturated K$_2$CO$_3$ aqueous solution (15 mL). The aqueous layer was extracted with CH$_2$Cl$_2$ (15 mL×3), and the organic layers were combined, dried over Na$_2$SO$_4$ and concentrated in vacuo. The residue was purified by column chromatography (silica gel, MeOH:EtOAc=1:9) to generate the pure product (IX-3, 0.067 g, 78%).

Example 95

The synthetic procedure of cis-6-{{(±)-4-[2-(3-fluorophenethoxy)ethylamino]pyrrolidin-3-yl}methyl}-4-methylpyridin-2-amine (P-78) is the same as that of (±)-cis-N$^1$-{-4'-[(6"-amino-4"-methylpyridin-2"-yl)methyl]pyrrolidin-3'-yl}-N$^2$-substituted alkyl ethane-1,2-diamine tetrahydrochloride (I-6a) (95%)

Examples 96-98 can be considered in conjunction with Scheme XI' below. The phenyl groups of compounds P-79 in Scheme XI' can be, alternatively, substituted at any of the para, meta or ortho positions with substituents including but not limited to halogen, alkyl or halogenated alkyl. Likewise, via such reactions showed in Scheme XI', the phenyl groups of the compounds of FIG. 8 can be substituted.

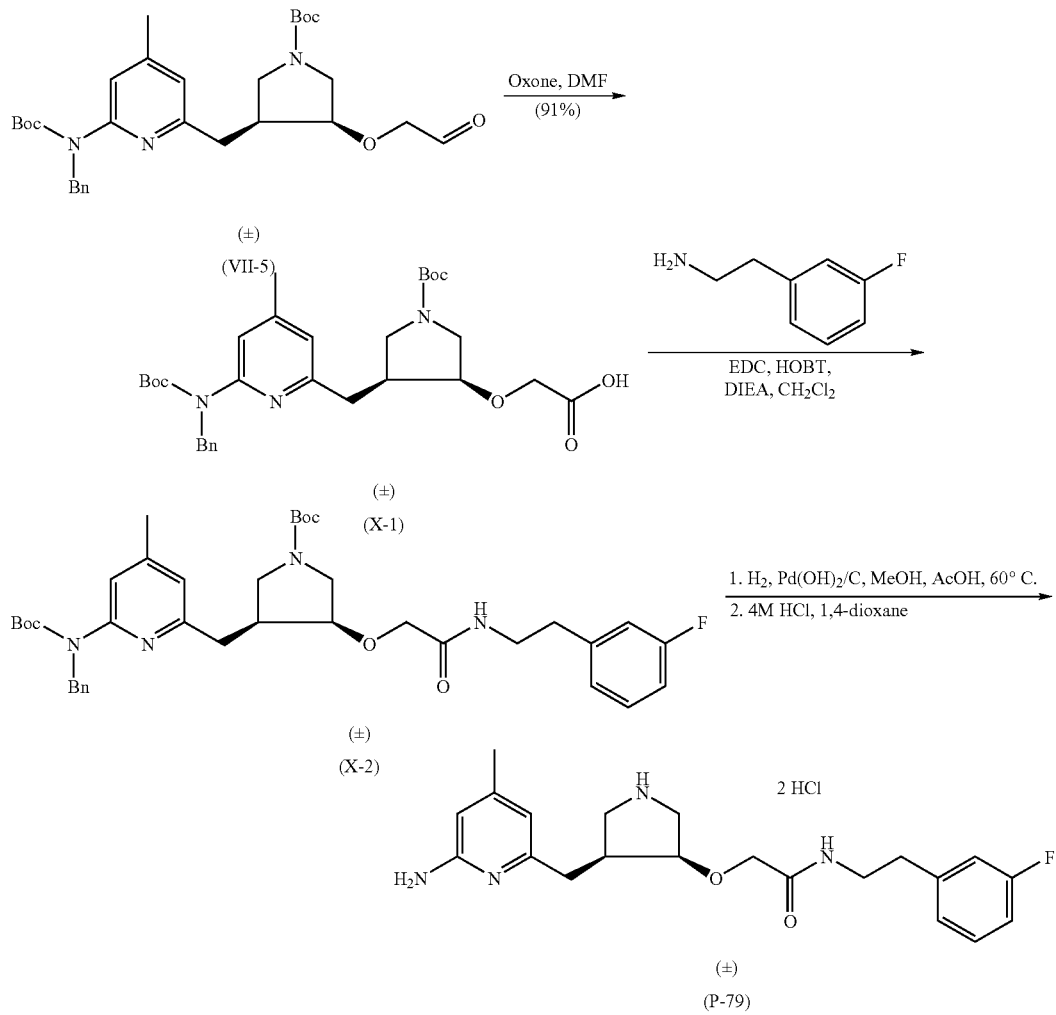

Example 96

Synthesis of (±)-2-{cis-4-{{6-[benzyl(tert-butoxycarbonyl)amino]-4-methylpyridin-2-yl}methyl}-1-(tert-butoxycarbonyl)pyrrolidin-3-yloxy}acetic acid (X-1).

To a solution of VII-5 (0.11 g, 0.0002 mol) in anhydrous DMF (4 mL) was added oxone (0.14 g, 0.00022 mol). The mixture was stirred for 3 h at room temperature. The solvent was removed under reduced pressure. The residue was dissolved in 1 M HCl aqueous solution (15 mL) and extracted with EtOAc (15 mL×3). The combined organic layers were washed with 1 M HCl (15 mL×3), dried over $Na_2SO_4$, and evaporated in vacuo. The residue was purified by column chromatography (silica gel, EtOAc:MeOH=5:1) to afford the pure product (X-1, 0.10 g, 91%).

Example 97

The synthetic procedure of (±) cis-tert-butyl 3-{{6-[benzyl(tert-butoxycarbonyl)amino]-4-methylpyridin-2-yl}methyl}-4-[2-(3-fluorophenethylamino)-2-oxoethoxy]pyrrolidine-1-carboxylate (X-2) is the same as that of (±) cis-tert-butyl 3-2-[tert-butoxycarbonyl(3-fluorophenethyl)amino]acetamido}-4-{[6-(tert-butoxycarbonyl amino)-4-methylpyridin-2-yl]methyl}pyrrolidine-1-carboxylate (VIII-5).

Example 98

The synthetic procedure of (±)-2-{cis-4-[(6-amino-4-methylpyridin-2-yl)methyl]pyrrolidin-3-yloxy}-N-(3-fluorophenethyl)acetamide (P-79) is the same as those of (±) cis-tert-butyl 3-{2-[tert-butoxycarbonyl(3-fluorophenethyl)amino]ethoxy}-4-{[6-(tert-butoxycarbonylamino)-4-methylpyridin-2-yl]methyl}pyrrolidine-1-carboxylate (VII-8) and of (±)-cis-$N^1$-{-4'-[(6"-amino-4"-methylpyridin-2"-yl)methyl]pyrrolidin-3'-yl}-$N^2$-substituted alkyl ethane-1,2-diamine tetrahydrochloride (I-6a).

Examples 99-102 can be considered in conjunction with Scheme XII' below. The phenyl groups of compounds P-80 in Scheme XII' can be, alternatively, substituted at any of the para, meta or ortho positions with substituents including but not limited to halogen, alkyl or halogenated alkyl. Likewise, via such reactions showed in Scheme XII', the phenyl groups of the compounds of FIG. 8 can be substituted.

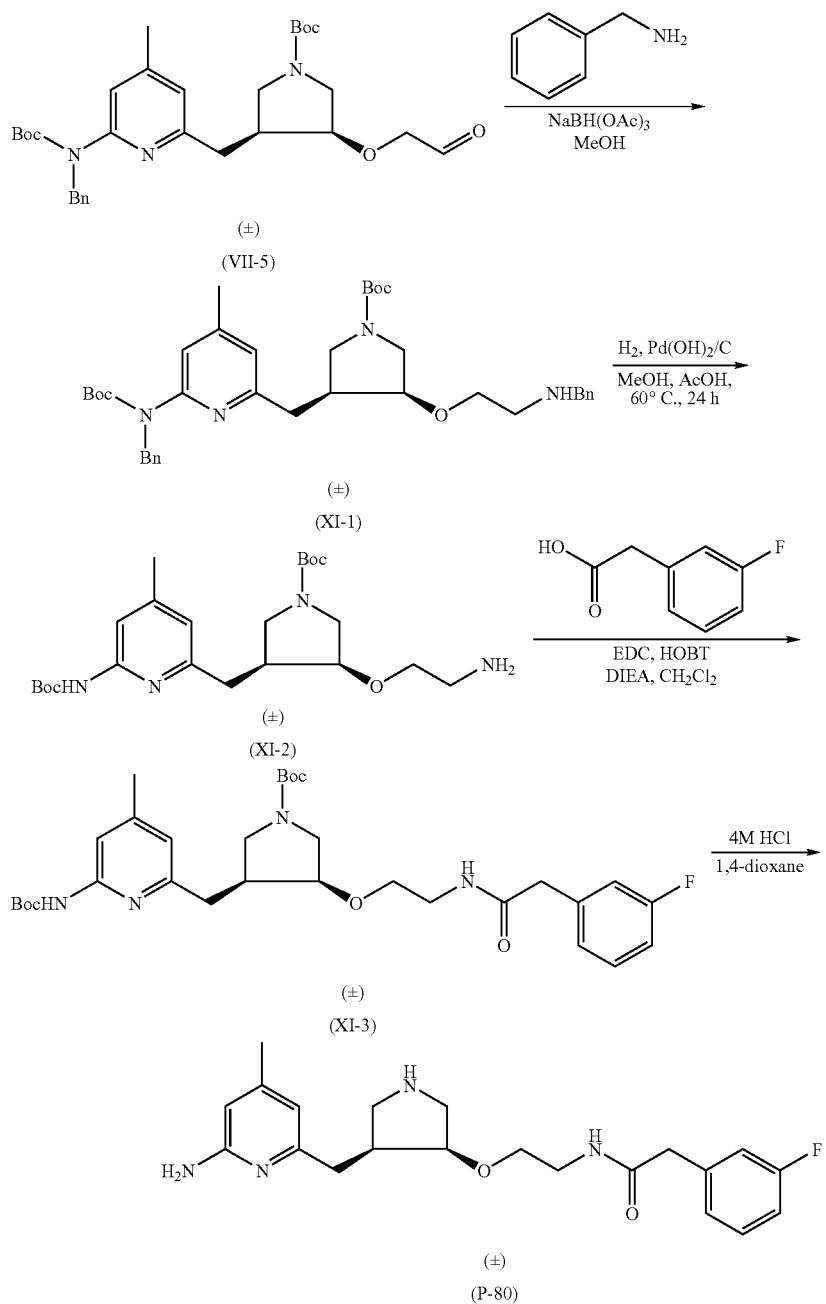

Example 99

Synthesis of (±) cis-tert-butyl 3-{{6-[benzyl(tert-butoxycarbonyl)amino]-4-methylpyridin-2-yl}methyl}-4-[2-(benzylamino)ethoxy]pyrrolidine-1-carboxylate (XI-1).

To a solution of VII-5 (0.2 mmol) in anhydrous CH$_2$Cl$_2$ (3 mL) was added benzylamine (0.3 mmol). The solution was stirred for 10 min. MeOH (2 mL), and NaBH(OAc)$_3$ (0.25 mmol) were added, and the mixture was stirred for 2 h. The mixture was poured into saturated NaHCO$_3$ aqueous solution (15 mL) and extracted with CH$_2$Cl$_2$ (15 mL×4). The organic layers were combined, dried over Na$_2$SO$_4$ and concentrated in vacuo. The residue was purified by column chromatography (silica gel, MeOH:EtOAc=1:9) to generate the pure product XI-1.

Example 100

The synthetic procedure of (±) cis-tert-butyl 3-(2-aminoethoxy)-4-{[6-(tert-butoxycarbonylamino)-4-methylpyridin-2-yl]methyl}pyrrolidine-1-carboxylate (XI-2) is the same as that of (±) cis-tert-butyl 3-{2-[tert-butoxycarbonyl (3-fluorophenethyl)amino]ethoxy}-4-{[6-(tert-butoxycarbonylamino)-4-methylpyridin-2-yl]methyl}pyrrolidine-1-carboxylate (VII-8).

Example 101

The synthetic procedure of (±) cis-tert-butyl 3-{[6-(tert-butoxycarbonylamino)-4-methylpyridin-2-yl]methyl}-4-{2-[2-(3-fluorophenyl)acetamido]ethoxy}pyrrolidine-1-carboxylate (XI-3) is the same as that of (±) cis-tert-butyl 3-{2-[tert-butoxycarbonyl(3-fluorophenethyl)amino]acetamido}-4-{[6-(tert-butoxycarbonylamino)-4-methylpyridin-2-yl]methyl}pyrrolidine-1-carboxylate (VIII-5).

Example 102

The synthetic procedure of (±)-N-{2-{cis-4-[(6-amino-4-methylpyridin-2-yl)methyl]pyrrolidin-3-yloxy}ethyl}-2-(3-fluorophenyl)acetamide dihydrochloride (P-80) is the same as that of (±)-cis-$N^1$-{-4'-[(6"-amino-4"-methylpyridin-2"-yl)methyl]pyrrolidin-3'-yl}-$N^2$-substituted alkyl ethane-1,2-diamine tetrahydrochloride (I-6a).

Examples 103-117 can be considered in conjunction with Schemes XIII'-XV' below. The introduction of the chiral auxiliary to intermediate VII-3 is a consideration for the synthesis of the enantiopure compounds. The other compounds in FIG. 7 and FIG. 8 can be synthesized by the same method. The phenyl groups of compounds in Schemes XIII'-XV' can be, alternatively, substituted at any of the para, meta or ortho positions with substituents including but not limited to halogen, alkyl or halogenated alkyl. Likewise, via such reactions showed in Schemes XIII'-XV', the phenyl groups of the compounds of FIG. 7 and FIG. 8 can be substituted.

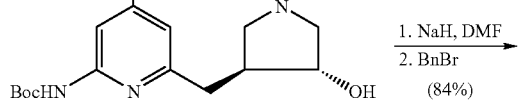

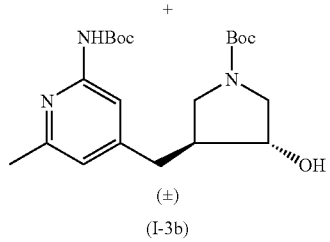

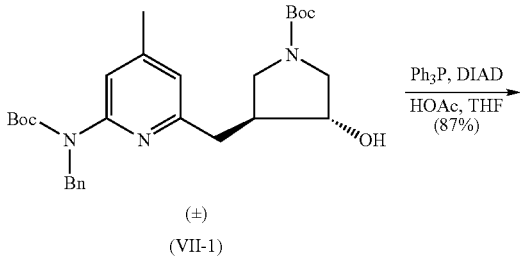

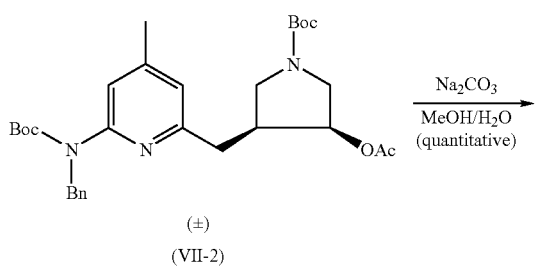

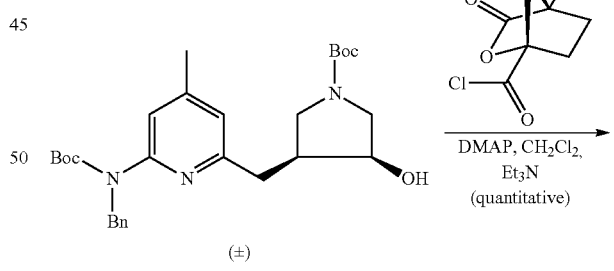

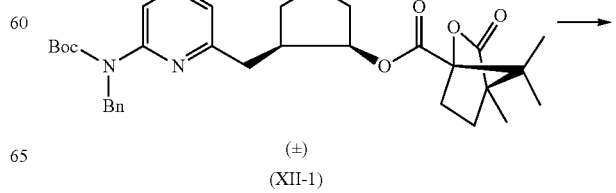

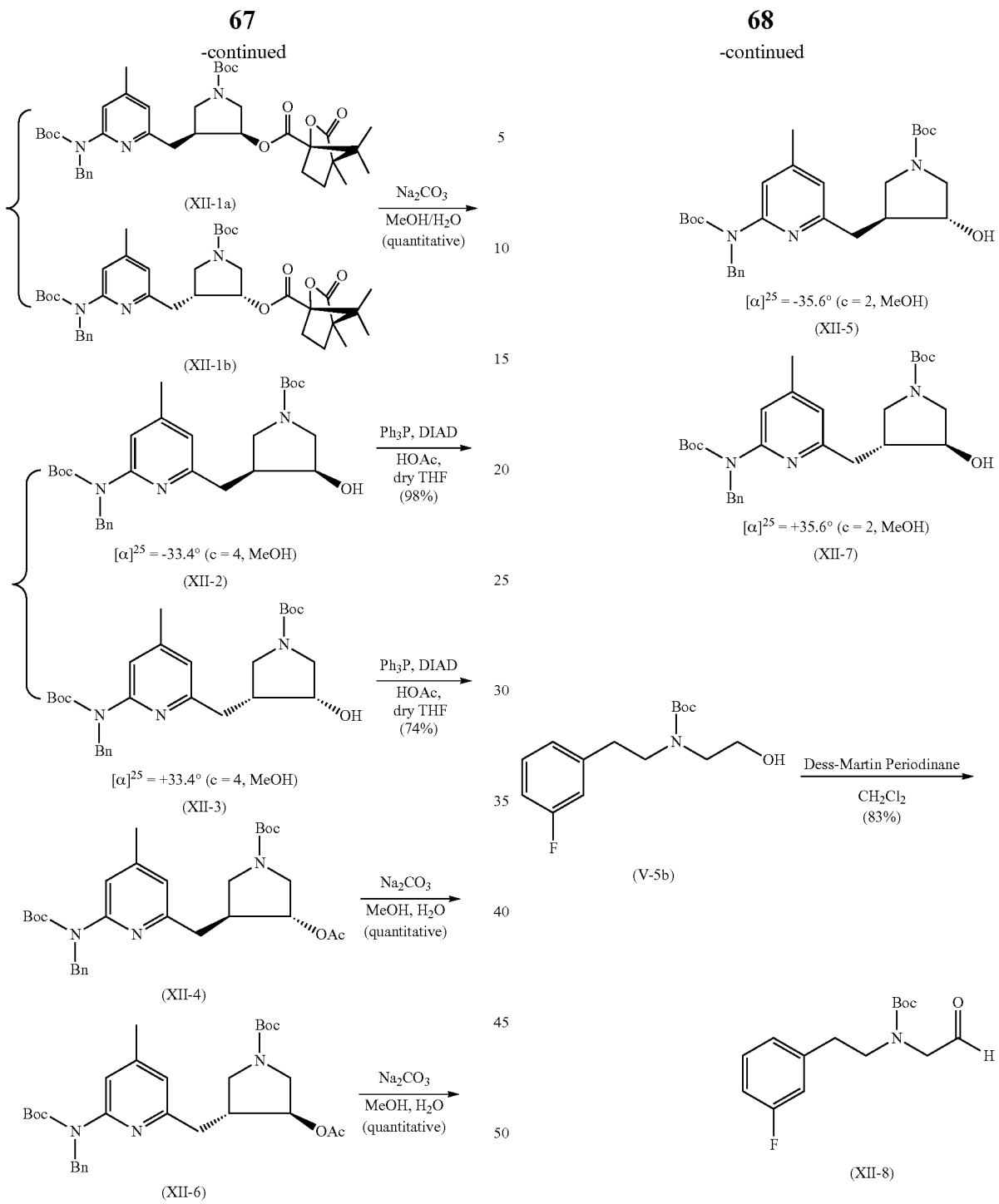
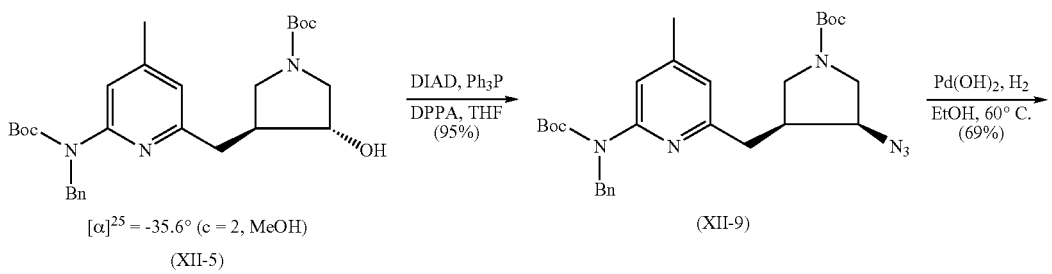
Scheme XIV'
a.

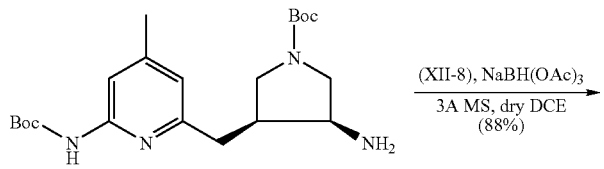
(XII-10)
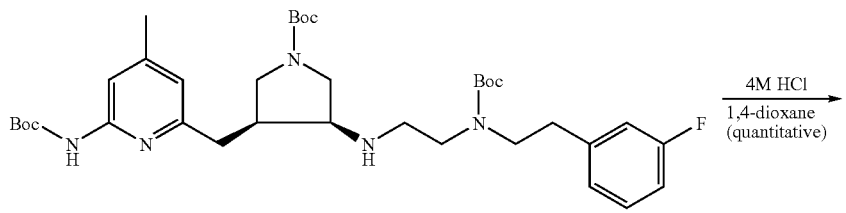
(XII-11)
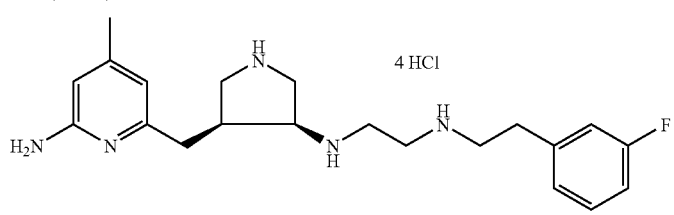
(XII-12)
b.
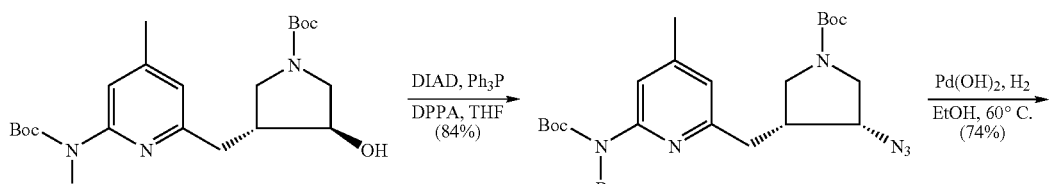
(XII-7) (XII-13)
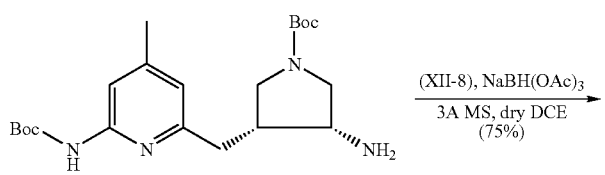
(XII-14)
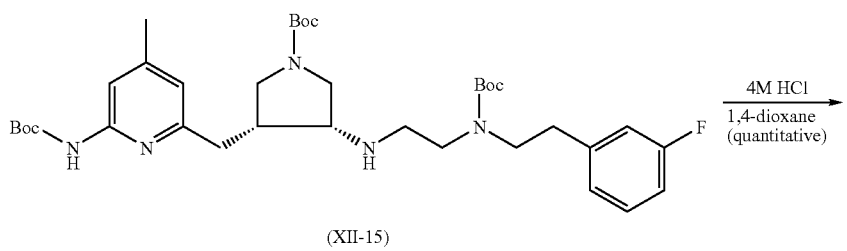
(XII-15)

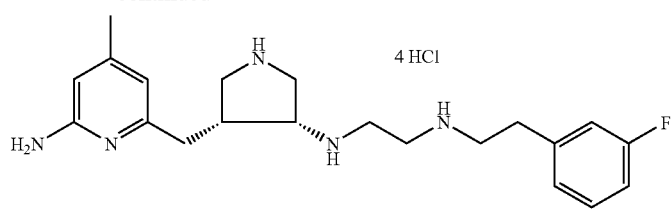
$[\alpha]^{25} = +30.4°$ (c = 1, MeOH)
(XII-16)
c.
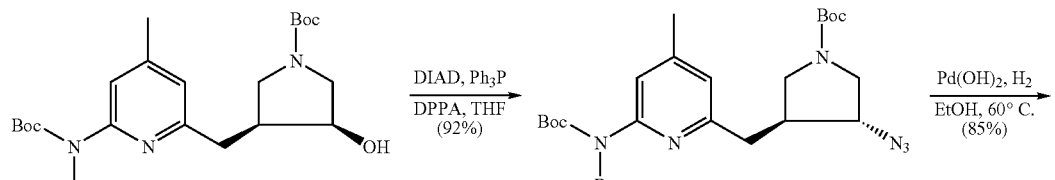
$[\alpha]^{25} = -33.4°$ (c = 4, MeOH)
(XII-2)
(XII-17)
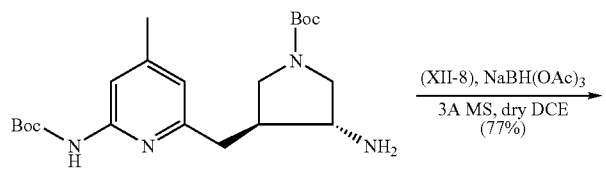
$[\alpha]^{25} = -40.7°$ (c = 2, MeOH)
(XII-18)
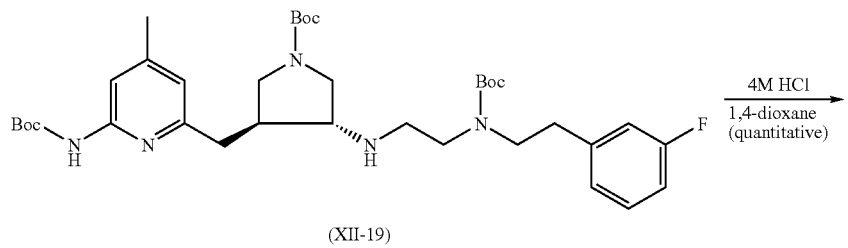
(XII-19)
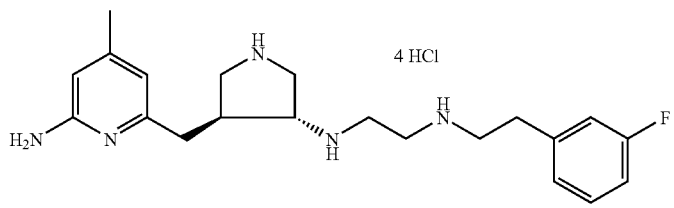
$[\alpha]^{25} = -27.0°$ (c = 1, MeOH)
(XII-20)
d.
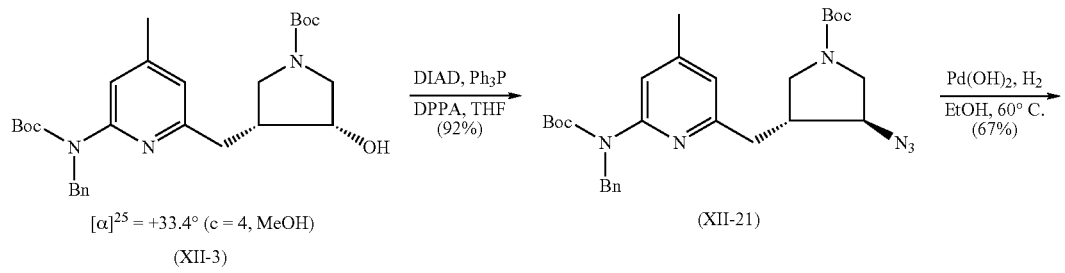
$[\alpha]^{25} = +33.4°$ (c = 4, MeOH)
(XII-3)
(XII-21)

-continued
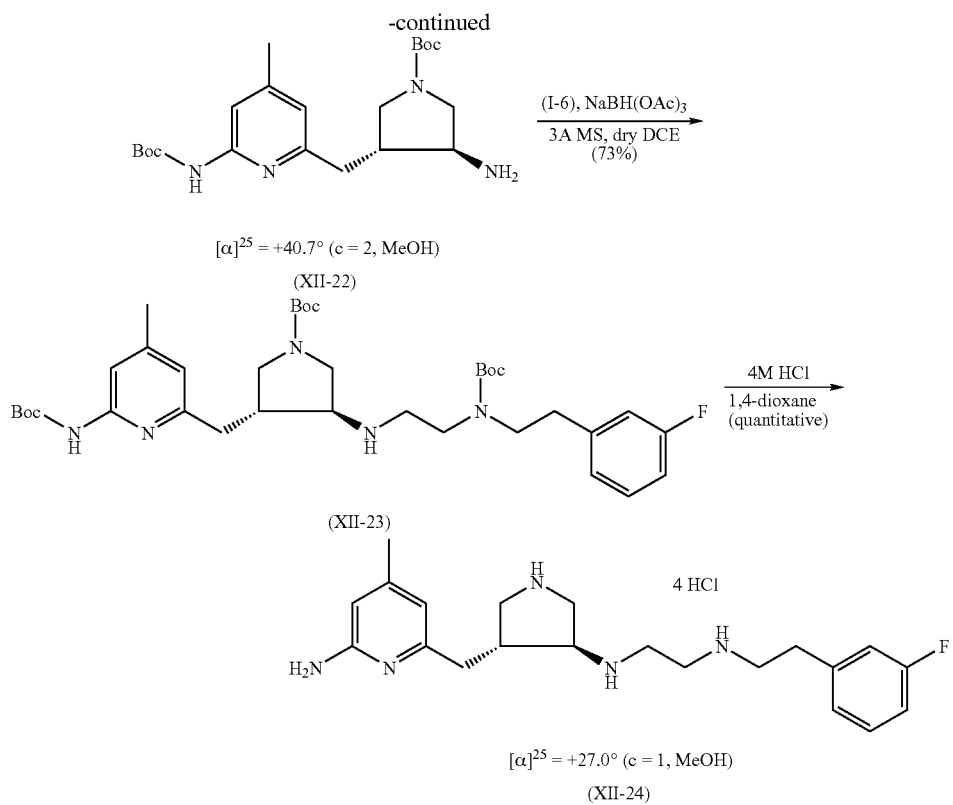
Scheme XV'
a.
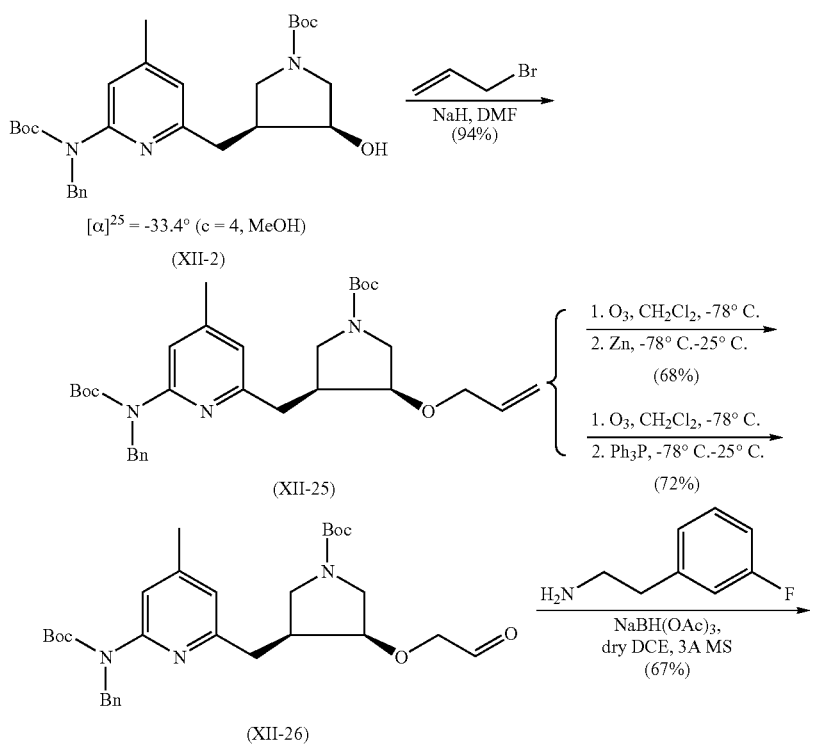

-continued
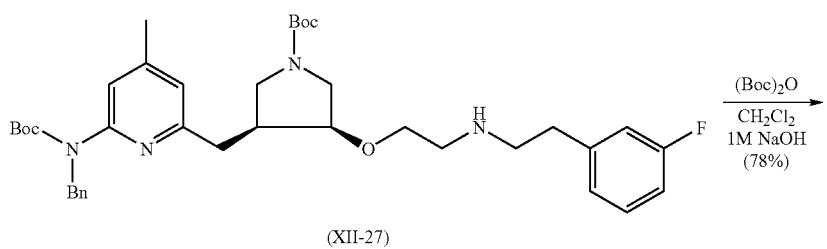
(XII-27)
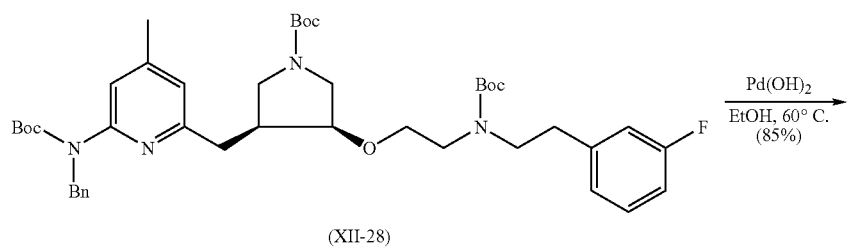
(XII-28)
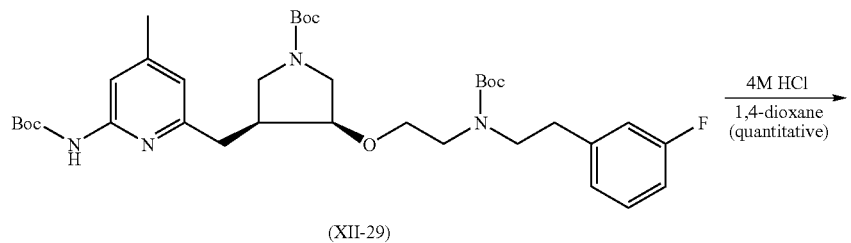
(XII-29)
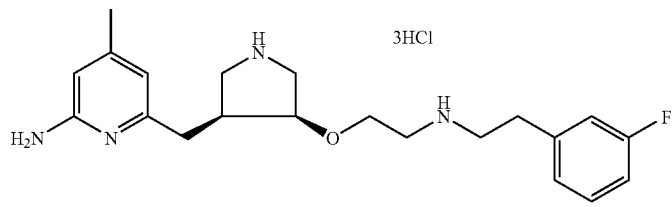
$[\alpha]^{25} = +36.4°$ (c= 1, MeOH)
(XII-30)
b.
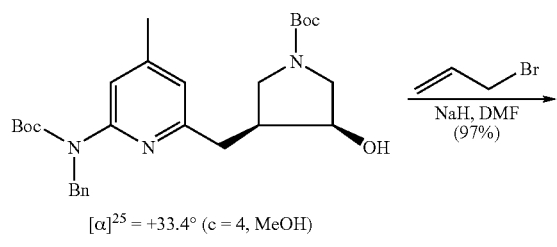
$[\alpha]^{25} = +33.4°$ (c = 4, MeOH)
(XII-6)
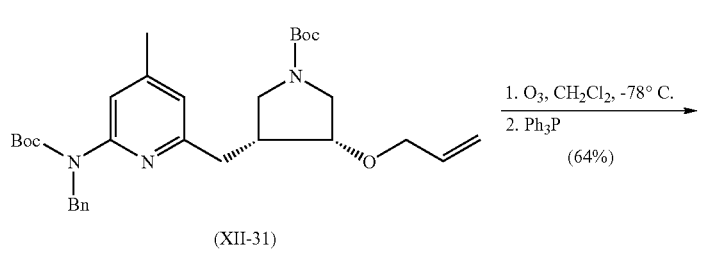
(XII-31)

-continued
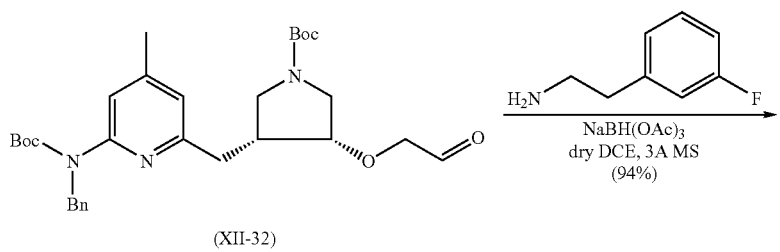
(XII-32)
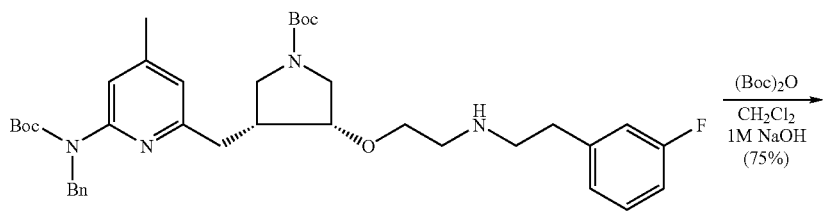
(XII-33)
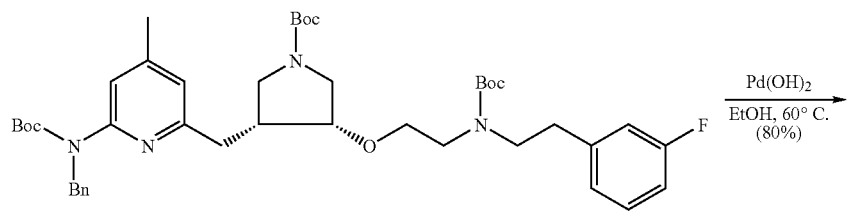
(XII-34)
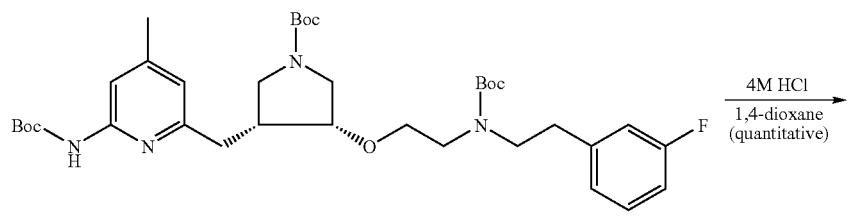
(XII-35)
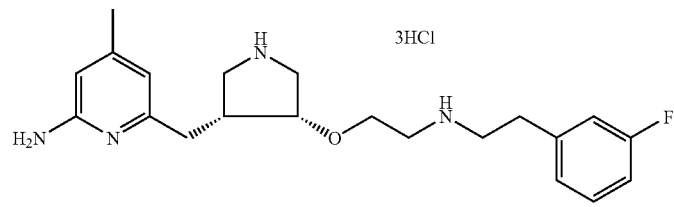
(XII-36)
$[\alpha]^{25} = -36.4°$ (c = 1, MeOH)
c.
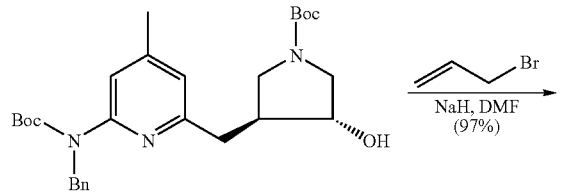
$[\alpha]^{25} = -35.6°$ (c = 2, MeOH)
(XII-5)

-continued
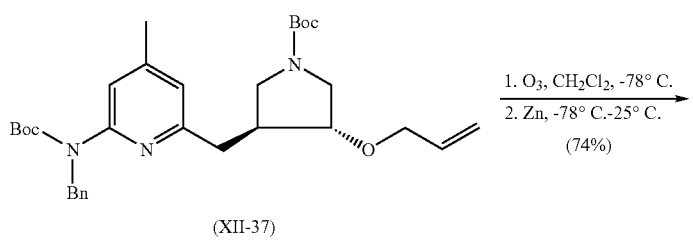
(XII-37)
1. O₃, CH₂Cl₂, -78° C.
2. Zn, -78° C.-25° C.
(74%)
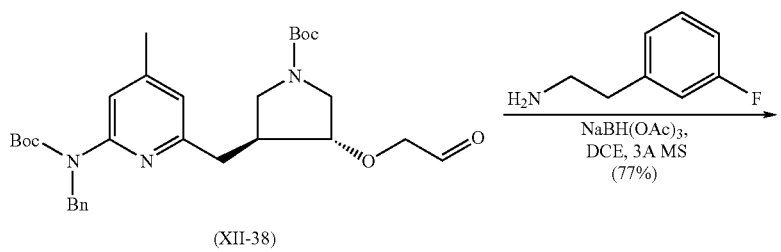
(XII-38)
H₂N–CH₂CH₂–(3-F-C₆H₄)
NaBH(OAc)₃,
DCE, 3A MS
(77%)
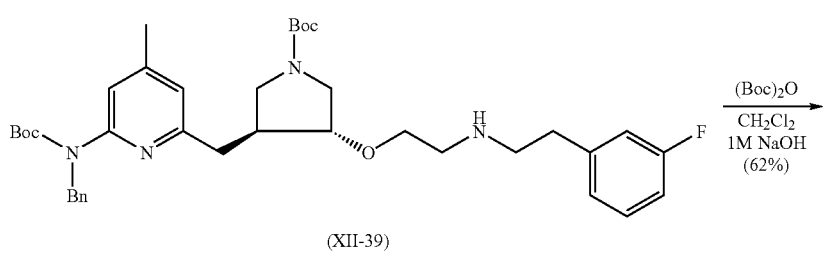
(XII-39)
(Boc)₂O
CH₂Cl₂
1M NaOH
(62%)
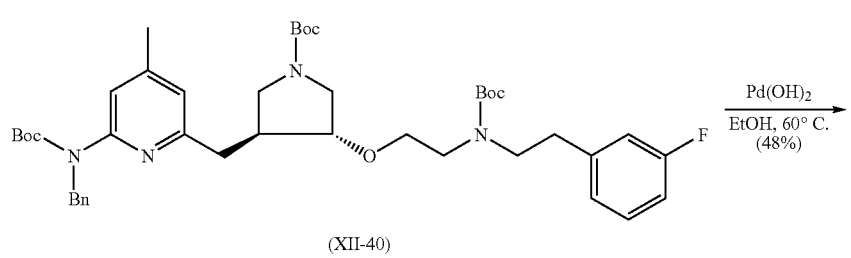
(XII-40)
Pd(OH)₂
EtOH, 60° C.
(48%)
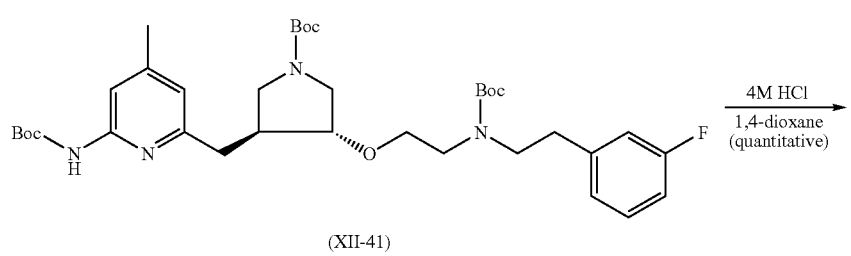
(XII-41)
4M HCl
1,4-dioxane
(quantitative)
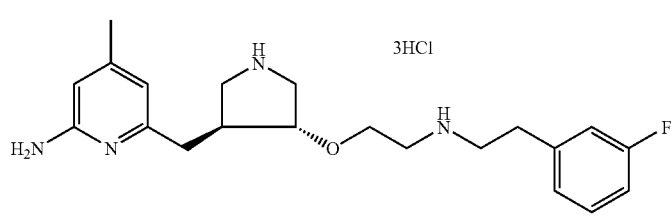
3HCl
$[\alpha]^{25} = -33.6°$ (c = 1, MeOH)
(XII-42)

-continued
d.
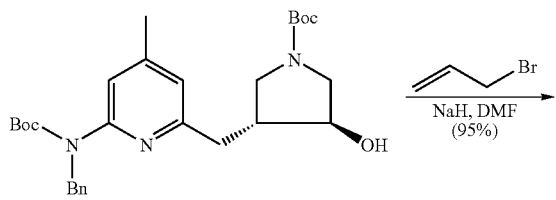
(XII-7)
$[\alpha]^{25} = +35.6°$ (c = 2, MeOH)
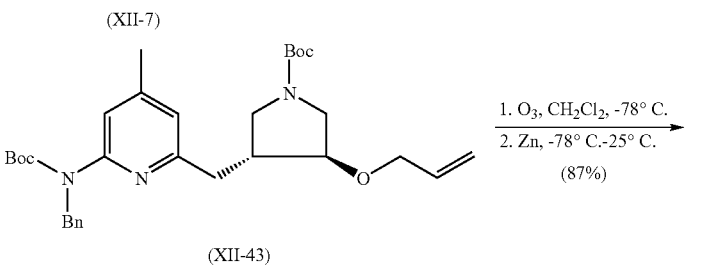
(XII-43)
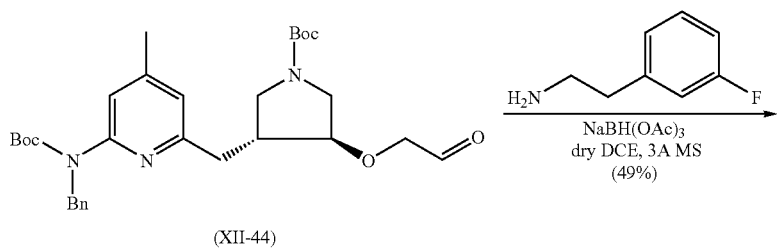
(XII-44)
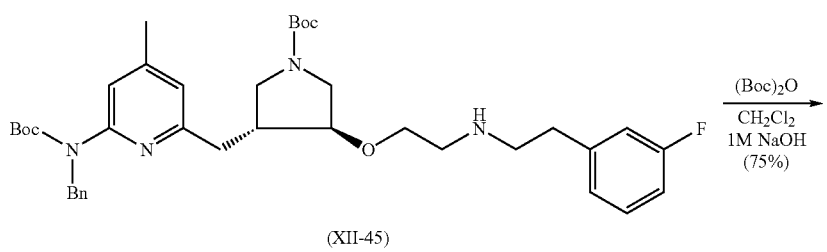
(XII-45)
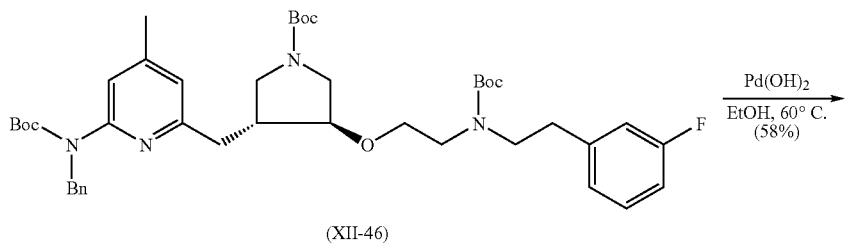
(XII-46)
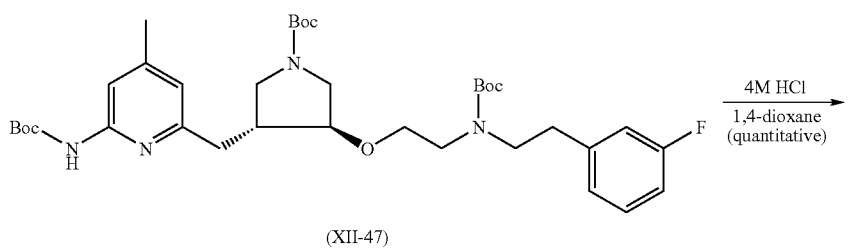
(XII-47)

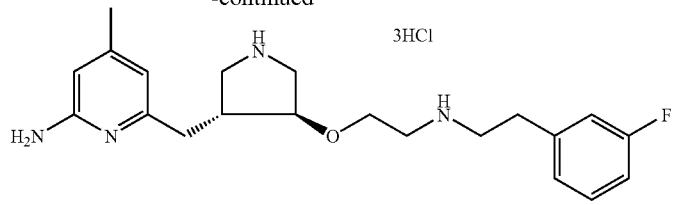

$[\alpha]^{25} = +33.6°$ (c = 1, MeOH)

(XII-48)

Example 103

Synthesis of (3S,4S)-tert-butyl 3-{{6-[benzyl(tert-butoxycarbonyl)amino]-4-methylpyridin-2-yl}methyl}-4-{(1S,4R)-4,7,7-trimethyl-3-oxo-2-oxabicyclo[2.2.1]heptane-1-carbonyloxy}pyrrolidine-1-carboxylate (XII-1a) and (3R,4R)-tert-butyl 3-{{6-[benzyl(tert-butoxycarbonyl)amino]-4-methylpyridin-2-yl}methyl}-4-{(1S,4R)-4,7,7-trimethyl-3-oxo-2-oxabicyclo[2.2.1]heptane-1-carbonyloxy}pyrrolidine-1-carboxylate (XII-1b)

To a solution of VII-3 (0.5 g, 0.001 mol) in dry $CH_2Cl_2$ (10 mL) cooled in an ice-water bath were added $Et_3N$ (0.2 g, 0.28 mL, 0.002 mol), 4-dimethylaminopyridine (DMAP, 0.012 g, 0.0001 mol), and (1S)-(–)-camphanic chloride (0.27 g, 0.00125 mol). The reaction mixture was stirred at 0° C. under a $N_2$ atmosphere for 1 h, and stirring was continued at room temperature for 6 h. The reaction mixture was quenched with saturated aqueous $NH_4Cl$ solution (10 mL). The organic layer was separated, and the aqueous layer was extracted with $CH_2Cl_2$ (10 mL×3). The combined organic layers were washed with 5% aqueous $NaHCO_3$ (10 mL×2), brine (10 mL), and dried over $Na_2SO_4$. The solvent was then concentrated in vacuo. The residue was purified by column chromatography (silica gel, hexanes:EtOAc=8:2) to afford a white solid (0.68 g, quantitative yield). The III-4a and III-4b can be further separated by column chromatography (silica gel, Cyclohexane:EtOAc=9.0:1.0. $R_f$: III-4a 0.22; III-4b: 0.19). III-4a and III-4b can also be separated by recrystallization with a mixture of $CH_3OH$ and $H_2O$ ($CH_3OH$:$H_2O$=9:1): III-5b is recrystallized from the solution, while III-5a stays in the solution. A couple of recrystallizations afford pure product. XII-1a, white solid (0.34 g); XII-1b, white solid (0.34 g).

Example 104

Synthesis of (3S,4S)-tert-butyl 3-{{6-[benzyl(tert-butoxycarbonyl)amino]-4-methylpyridin-2-yl}methyl}-4-hydroxypyrrolidine-1-carboxylate (XII-2) and (3R,4R)-tert-butyl 3-{{6-[benzyl(tert-butoxycarbonyl)amino]-4-methylpyridin-2-yl}methyl}-4-hydroxypyrrolidine-1-carboxylate (XII-3)

To a solution of XII-1a or XII-1b (1.4 g, 0.002 mol) in $CH_3OH$ (40 mL) was added at room temperature a solution of $Na_2CO_3$ (0.42 g, 0.004 mol) in $H_2O$ (10 mL). The solution was stirred at room temperature for 14 h. The solvent was evaporated in vacuo. The residue was dissolved in a mixture of EtOAc (10 mL) and $H_2O$ (10 mL). The aqueous layer was extracted with EtOAc (10 mL×3). The combined organic layers were dried over $Na_2SO_4$, and concentrated in vacuo. The residue was purified by column chromatography (silica gel, hexanes:EtOAc=6:4) to afford a colorless oil (quantitative yield). XII-2, colorless oil (1.0 g, quantitative yield). $[\alpha]^{25}$=−33.4° (c=4, $CH_3OH$). XII-3, colorless oil (1.0 g, quantitative yield), $[\alpha]^{25}$=+33.4° (c=4, $CH_3OH$).

Example 105

Synthesis of (3R,4S)-tert-butyl 3-acetoxy-4-{{6-[benzyl(tert-butoxycarbonyl)amino]-4-methylpyridin-2-yl}methyl}pyrrolidine-1-carboxylate (XII-4) and (3S,4R)-tert-butyl 3-acetoxy-4-{{6-[benzyl(tert-butoxycarbonyl)amino]-4-methylpyridin-2-yl}methyl}pyrrolidine-1-carboxylate (XII-6)

To an ice-cooled solution of $Ph_3P$ (0.34 g, 0.0013 mol) in dry THF (5 mL) was added XII-2 (0.5 g, 0.001 mol) in dry THF (15 mL) through a cannula under a $N_2$ atmosphere. DIAD (0.26 g, 0.26 mL, 0.0013 mol) was then added dropwise, and the solution was stirred for 20 min at 0° C. Acetic acid (HOAc, 0.078 g, 0.074 mL, 0.0013 mol) was then added at 0° C., and the solution was stirred at room temperature for 48 h. The solution was then concentrated, and the residue was purified directly by column chromatography (silica gel, hexanes:EtOAc=8:2) to yield a colorless oil (0.45 g, 87%). XII-4, colorless oil (0.53 g, 98%); XII-6, colorless oil (0.40 g, 74%).

Example 106

Synthesis of (3S,4R)-tert-butyl 3-{{6-[benzyl(tert-butoxycarbonyl)amino]-4-methylpyridin-2-yl}methyl}-4-hydroxypyrrolidine-1-carboxylate (XII-5) and (3R,4S)-tert-butyl 3-{{6-[benzyl(tert-butoxycarbonyl)amino]-4-methylpyridin-2-yl}methyl}-4-hydroxypyrrolidine-1-carboxylate (XII-7)

To a solution of XII-4 (0.55 g, 0.001 mol) in $CH_3OH$ (20 mL) was added at room temperature a solution of $Na_2CO_3$ (0.21 g, 0.002 mol) in $H_2O$ (5 mL). The solution was stirred at room temperature for 14 h. The solvent was evaporated in vacuo. The residue was dissolved in a mixture of EtOAc (8 mL) and $H_2O$ (8 mL). The aqueous layer was extracted with EtOAc (8 mL×3). The combined organic layers were dried over $Na_2SO_4$ and concentrated in vacuo. The residue was purified by column chromatography (silica gel, Hexanes:EtOAc=6:4) to afford a colorless oil (XII-5, 0.5 g, quantitative yield). $[\alpha]^{25}$=−35.6° (c=2, MeOH).

The procedure to prepare XII-7 is the same as that to prepare III-8. The NMR and MS are also the same as those of XII-5. XII-7, colorless oil (0.5 g, quantitative yield). $[\alpha]^{25}$=+35.6° (c=2, MeOH).

Example 107

Synthesis of tert-butyl 3-fluorophenethyl(2-oxoethyl)carbamate (XII-8).

To a suspension of Dess-Martin periodinane (0.51 g, 0.0012 mol) in anhydrous $CH_2Cl_2$ (10 mL) was added a solution of tert-butyl 3-fluorophenethyl(2-hydroxyethyl)carbamate (V-5b, 0.28 g, 0.001 mol) in anhydrous $CH_2Cl_2$ (5 mL) via a cannula, and the reaction mixture was stirred at room temperature for 18 h under a $N_2$ atmosphere. $Na_2S_2O_3$ (1 M, 10 mL) was then added to the reaction mixture. After being stirred for 10 min, the organic layer was separated. The aqueous layer was extracted with $CH_2Cl_2$ (15 mL×3). The combined organic layers were washed with 5% aqueous $NaHCO_3$ (20 mL) and brine (20 mL), and dried over $Na_2SO_4$. The solvent was evaporated. The residue was then purified by column chromatography (silica gel, hexane:EtOAc=7.5:2.5) to afford a colorless oil (XII-8, 0.24 g, 83%).

Example 108

Synthesis of (3S,4S)-tert-butyl 3-azido-4-{{6-[benzyl(tert-butoxycarbonyl)amino]-4-methylpyridin-2-yl}methyl}pyrrolidine-1-carboxylate (XII-9), (3R,4R)-tert-butyl 3-azido-4-{{6-[benzyl(tert-butoxycarbonyl)amino]-4-methylpyridin-2-yl}methyl}pyrrolidine-1-carboxylate (XII-13), (3R,4S)-tert-butyl 3-azido-4-{{6-[benzyl(tert-butoxycarbonyl)amino]-4-methylpyridin-2-yl}methyl}pyrrolidine-1-carboxylate (XII-17), and (3S,4R)-tert-butyl 3-azido-4-{{6-(benzyl[tert-butoxycarbonyl)amino]-4-methylpyridin-2-yl}methyl}pyrrolidine-1-carboxylate (XII-21)

To $Ph_3P$ (0.33 g, 0.00125 mol) in a dry THF (5 mL) solution was added XII-5 (0.5 g, 0.001 mol) in dry THF (10 mL) at 0° C. under a $N_2$ atmosphere via cannula. DIAD (0.26 g, 0.26 mL, 0.0013 mol) was added dropwise, and the solution was stirred at 0° C. for 20 min. DPPA (0.36 g, 0.28 mL, 0.0013 mol) was then added dropwise at ° C., and the reaction mixture was stirred for 22 h at room temperature. The solvent was concentrated in vacuo. The crude residue was directly purified by column chromatography (silica gel, hexanes:EtOAc=9:1) to afford a colorless oil (III-11, 0.5 g, 95%).

The procedure to prepare XII-13 is the same as that to prepare XII-9. XII-13 colorless oil (0.44 g, 84%).

The procedure to prepare XII-17 is the same as that to prepare XII-9. III-17 colorless oil (0.48 g, 92%).

The procedure to prepare XII-21 is the same as that to prepare XII-9. XII-21 colorless oil (0.48 g, 92%).

Example 109

Synthesis of (3S,4S)-tert-butyl 3-amino-4-{[6-(tert-butoxycarbonylamino)-4-methylpyridin-2-yl]methyl}pyrrolidine-1-carboxylate (XII-10), (3R,4R)-tert-butyl 3-amino-4-{[6-(tert-butoxycarbonylamino)-4-methylpyridin-2-yl]methyl}pyrrolidine-1-carboxylate (XII-14), (3R,4S)-tert-butyl 3-amino-4-{[6-(tert-butoxycarbonylamino)-4-methylpyridin-2-yl]methyl}pyrrolidine-1-carboxylate (XII-18), and (3S,4R)-tert-butyl 3-amino-4-{[6-(tert-butoxycarbonylamino)-4-methylpyridin-2-yl]methyl}pyrrolidine-1-carboxylate (XII-22)

A solution of XII-9 (0.52 g, 0.001 mol) in EtOH (20 mL) was treated with 20% wt $Pd(OH)_2$ on carbon (300 mg). The reaction mixture was stirred at 60° C. under a hydrogen atmosphere for 36 h. The catalyst was filtered through Celite. The Celite pad was washed with EtOH (10 mL×2). The combined filtrate was concentrated in vacuo. The residue was purified by column chromatography (silica gel, $CH_2Cl_2$:$CH_3OH$=9.5:0.5) to afford a pale-green oil (XII-9, 0.28 g, 69%). $[\alpha]^{25}$=–45.4° (c=–2, MeOH).

The procedure to prepare XII-14 is the same as that to prepare XII-10. XII-14 pale-green oil (0.30 g, 74%). $[\alpha]^{25}$=+45.4° (c=2, MeOH).

The procedure to prepare XII-18 is the same as that to prepare XII-10. XII-18 pale-green oil (0.35 g, 85%). $[\alpha]^{25}$=–40.7° (c=2, MeOH).

The procedure to prepare XII-22 is the same as that to prepare XII-10. XII-22 pale-green oil (0.27 g, 67%). $[\alpha]^{25}$=+40.7° (c=2, MeOH).

Example 110

Synthesis of (3S,4S)-tert-butyl 3-{2-[tert-butoxycarbonyl(3-fluorophenethyl)amino]ethylamino}-4-{[6-(tert-butoxycarbonylamino)-4-methylpyridin-2-yl]methyl}pyrrolidine-1-carboxylate (XII-11), (3R,4R)-tert-butyl 3-{2-[tert-butoxycarbonyl(3-fluorophenethyl)amino]ethylamino}-4-{[6-(tert-butoxycarbonylamino)-4-methylpyridin-2-yl]methyl}pyrrolidine-1-carboxylate (XII-15), (3R,4S)-tert-butyl 3-{2-[tert-butoxycarbonyl(3-fluorophenethyl)amino]ethylamino}-4-{[6-(tert-butoxycarbonylamino)-4-methylpyridin-2-yl]methyl}pyrrolidine-1-carboxylate (XII-19), and (3S,4R)-tert-butyl 3-{2-[tert-butoxycarbonyl(3-fluorophenethyl)amino]ethylamino}-4-{[6-(tert-butoxycarbonylamino)-4-methylpyridin-2-yl]methyl}pyrrolidine-1-carboxylate (XII-23)

A mixture of XII-10 (0.2 g, 0.0005 mol), $NaBH(OAc)_3$ (0.04 g, 0.0002 mol) and 3 Å molecular sieves (0.5 g) in dry 1,2-dichloroethane (10 mL) was added XII-8 (0.14 g, 0.0005 mol) in dry 1,2-dichloroethane (5 mL) via cannula under a $N_2$ atmosphere. After the reaction mixture was stirred at room temperature under a $N_2$ atmosphere for 30 min. $NaBH(OAc)_3$ (0.11 g, 0.0005 mol) was added. The reaction mixture was stirred at room temperature under a $N_2$ atmosphere for 16 h, and then was filtered through Celite, and the Celite pad was washed with $CH_2Cl_2$ (5 mL×2). To the filtrate was then added 1 M NaOH (10 mL). The organic layer was separated, and the aqueous layer was extracted with $CH_2Cl_2$ (10 mL×2). The combined organic layers were washed with brine (10 mL), and dried over $MgSO_4$. The solvent was evaporated, and the residue was purified by column chromatography (silica gel, Hexane:EtOAc:$Et_3N$=8:2:0.25) to afford a colorless oil (XII-11, 0.3 g, 88%).

The procedure to prepare XII-15 is the same as that to prepare XII-11. XII-15, colorless oil (0.25 g, 74%).

The procedure to prepare XII-19 is the same as that to prepare XII-11. XII-19, colorless oil (0.26 g, 77%).

The procedure to prepare XII-23 is the same as that to prepare XII-11. XII-23, colorless oil (0.25 g, 73%).

Example 111

Synthesis of N$^1$-{(3'S,4'S)-4'-[(6"-amino-4"-methylpyridin-2"-yl)methyl]pyrrolidin-3'-yl}-N$^2$-(3'-fluorophenethyl)ethane-1,2-diamine tetrahydrochloride (XII-12), N$^1$-{(3'R,4'R)-4'-[(6"-amino-4"-ethylpyridin-2"-yl)methyl]pyrrolidin-3'-yl}-N$^2$-(3'-fluorophenethyl)ethane-1,2-diamine tetrahydrochloride (XII-16), N$^1$-{(3'R,4'S)-4'-[(6"-amino-4"-methylpyridin-2"-yl)methyl]pyrrolidin-3'-yl}-N$^2$-(3'-fluorophenethyl)ethane-1,2-diamine tetrahydrochloride (XII-20), and N$^1$-{(3'S,4'R)-4'-[(6"-amino-4"-methylpyridin-2"-yl)methyl]pyrrolidin-3'-yl}-N$^2$-(3'-fluorophenethyl)ethane-1,2-diamine tetrahydrochloride (XII-24)

XII-11 (0.14 g, 0.0002 mol) was cooled in an Iice-water bath under argon. A solution of 4 M HCl in 1,4-dioxane (4 mL) was then added slowly with stirring. The ice-water bath was removed after 3 h, and the reaction mixture was stirred at room temperature under an argon atmosphere for 34 h. The reaction mixture was concentrated in vacuo, and the residue was partitioned between water (10 mL) and ethyl acetate (10 mL). The aqueous layer was then washed with ethyl acetate (5 mL×2). After evaporation of water by high vacuum rotary evaporation, the residue was dried with a lyophilizer to afford a white solid (XII-12, 0.11 g, quantitative yield). [α]$^{25}$=−30.4° (c=1, MeOH).

The procedure to prepare XII-16 is the same as that to prepare XII-12. XII-16, white solid (0.11 g, quantitative yield). [α]$^{25}$=+30.4° (c=1, MeOH).

The procedure to prepare XII-20 is the same as that to prepare XII-12. XII-20, white solid (0.11 g, quantitative yield). [α]$^{25}$=−27.0° (c=1, MeOH).

The procedure to prepare XII-24 is the same as that to prepare XII-12. XII-24, white solid (0.11 g, quantitative yield). [α]$^{25}$=+27.0° (c=1, MeOH).

Example 112

Synthesis of (3S,4S)-tert-butyl 3-(allyloxy)-4-{{6-[benzyl(tert-butoxycarbonyl)amino]-4-methylpyridin-2-yl}methyl}pyrrolidine-1-carboxylate (XII-25), (3R,4R)-tert-butyl 3-(allyloxy)-4-{{6-[benzyl(tert-butoxycarbonyl)amino]-4-methylpyridin-2-yl}methyl}pyrrolidine-1-carboxylate (XII-31), (3R,4S)-tert-butyl 3-(allyloxy)-4-{{6-[benzyl(tert-butoxycarbonyl)amino]-4-methylpyridin-2-yl}methyl}pyrrolidine-1-carboxylate (XII-37), and (3S,4R)-tert-butyl 3-(allyloxy)-4-{{6-[benzyl(tert-butoxycarbonyl)amino]-4-methylpyridin-2-yl}methyl}pyrrolidine-1-carboxylate (XII-43)

To an ice-cooled solution of NaH (0.048 g, 0.0012 mol, 60% dispersion in mineral oil) in anhydrous DMF (1 ml) was added dropwise XII-2 (0.5 g, 0.001 mol) in anhydrous DMF (5 mL) under a N$_2$ atmosphere. The suspension was then stirred vigorously for 30 min at room temperature. The color of the reaction mixture changed from colorless to pale-red. Allyl bromide (0.16 g, 0.12 mL, 0.0013 mol) was added dropwise at 0° C. The reaction mixture was stirred at room temperature for 3 h. The excess NaH was quenched with H$_2$O (5 mL). The solvent was evaporated in vacuo. The residue was further diluted with water (10 mL) and EtOAc (10 mL). The organic layer was separated. The aqueous layer was extracted with EtOAc (10 mL×3). The combined organic layers were washed with brine (10 mL×2) and dried over Na$_2$SO$_4$. The solvent was evaporated, and the residue was purified by column chromatography (silica gel, hexanes:EtOAc=8:2) to afford a colorless oil (XII-25, 0.5 g, 94%).

The procedure to prepare XII-31 is the same as that to prepare XII-25. XII-31, colorless oil (0.52 g, 97%).

The procedure to prepare XII-37 is the same as that to prepare XII-25. XII-37, colorless oil (0.52 g, 97%).

The procedure to prepare XII-43 is the same as that to prepare XII-25. XII-43, colorless oil (0.51 g, 95%).

Example 113

Synthesis of (3S,4S)-tert-butyl 3-{{6-[benzyl(tert-butoxycarbonyl)amino]-4-methylpyridin-2-yl}methyl}-4-(2-oxoethoxy)pyrrolidine 1-carboxylate (XII-26), (3R,4R)-tert-butyl 3-{{6-[benzyl(tert-butoxycarbonyl)amino]-4-methylpyridin-2-yl}methyl}-4-(2-oxoethoxy)pyrrolidine-1-carboxylate (XII-32), (3S,4R)-tert-butyl 3-{{6-[benzyl(tert-butoxycarbonyl)amino]-4-methylpyridin-2-yl}methyl}-4-(2-oxoethoxy)pyrrolidine-1-carboxylate (XII-38), and (3R,4S)-tert-butyl 3-{{6-[benzyl(tert-butoxycarbonyl)amino]-4-methylpyridin-2-yl}methyl}-4-(2-oxoethoxy)pyrrolidine-1-carboxylate (XII-44)

Method A

XII-25 (0.54 g, 0.001 mol) was dissolved in CH$_2$Cl$_2$ (30 mL) and cooled to −78° C. Ozone was bubbled through the solution until a light blue color appeared. N$_2$ was bubbled through the solution until the blue color disappeared (about 30 min). Zinc (0.1 g, 0.0015 mol) was added followed by 5 mL of 50% acetic acid aqueous solution. The suspension was allowed to slowly warm to 0° C., stirred for 30 min, and then allowed to stir at room temperature for 30 min. The reaction mixture was diluted with CH$_2$Cl$_2$ (10 mL) and H$_2$O (20 mL). The organic layer was separated, and the aqueous layer was extracted with CH$_2$Cl$_2$ (10 mL×2). The combined organic layers were washed with H$_2$O (10 mL), saturated NaHCO$_3$ aqueous solution (10 mL×2), and brine (10 mL), and then dried over MgSO$_4$. The solvent was then concentrated in vacuo. The residue was purified by column chromatography (silica gel, hexanes: EtOAc=5:5) to afford a pale-yellow oil (XII-26, 0.37 g, 68%).

Method B

XII-25 (0.54 g, 0.001 mol) was dissolved in CH$_2$Cl$_2$ (30 mL) and cooled to −78° C. Ozone was bubbled through the solution until a light blue color appeared. N$_2$ was bubbled through the solution until the blue color disappeared (about 30 min). Ph$_3$P (0.32 g, 0.0012 mol) was added to the reaction mixture. The reaction mixture was allowed to warm slowly to 0° C., was stirred for 15 min, and then allowed to stir at room temperature for 30 min. The solvent was concentrated in vacuo. The residue was purified directly by column chromatography (silica gel, hexanes:EtOAc=5:5) to afford a pale-yellow oil (XII-26, 0.39 g, 72%).

The procedure to prepare XII-32 is the same as the method A to prepare XII-26. XII-32, pale-yellow oil (0.35 g, 64%).

The procedure to prepare XII-38 is the same as the method A to prepare XII-26. XII-38, pale-yellow oil (0.40 g, 74%).

The procedure to prepare XII-44 is the same as the method A to prepare XII-26. XII-44, pale-yellow oil (0.47 g, 87%).

Example 114

Synthesis of (3S,4S)-tert-butyl 3-{{6-[benzyl(tert-butoxycarbonyl)amino]-4-methylpyridin-2-yl}methyl}-4-[2-(3-fluorophenethylamino)ethoxy]pyrrolidine-1-carboxylate (XII-27), (3R,4R)-tert-butyl 3-{{6-[benzyl(tert-butoxycarbonyl)amino]-4-methylpyridin-2-yl}methyl}-4-[2-(3-fluorophenethylamino)ethoxy]pyrrolidine-1-carboxylate (XII-33), (3S,4R)-tert-butyl 3-{{6-[benzyl(tert-butoxycarbonyl)amino]-4-methylpyridin-2-yl}methyl}-4-[2-(3-fluorophenethylamino)ethoxy]pyrrolidine-1-carboxylate (XII-39), and (3R,4S)-tert-butyl 3-{{6-[benzyl(tert-butoxycarbonyl)amino]-4-methylpyridin-2-yl}methyl}-4-[2-(3-fluorophenethylamino)ethoxy]pyrrolidine-1-carboxylate (XII-45)

A mixture of XII-26 (0.54 g, 0.001 mol), 3-fluorophenethylamine (0.15 g, 0.15 mL, 0.0011 mol), $NaBH(OAc)_3$ (0.3 g, 0.0014 mol) and 3 Å molecular sieves (1 g) in dry 1,2-dichloroethane (20 mL) was stirred at room temperature under a $N_2$ atmosphere for 14 h. The reaction mixture was then filtered through Celite. The Celite pad was washed with $CH_2Cl_2$ (5 mL×2). To the combined organic layers was added 1M NaOH (20 mL). The organic layer was separated, and the aqueous layer was extracted with $CH_2Cl_2$ (10 mL×2). The combined organic layers was washed with brine (10 mL), and dried over $MgSO_4$. The solvent was concentrated in vacuo. The residue was purified by column chromatography (silica gel, hexanes:EtOAc $Et_3N$=6:4:0.25) to afford a pale-yellow oil (III-29, 0.44 g, 67%).

The procedure to prepare XII-33 is the same as that to prepare XII-27. XII-33, pale-yellow oil (0.62 g, 94%).

The procedure to prepare XII-39 is the same as that to prepare XII-27. XII-39, pale-yellow oil (0.51 g, 77%).

The procedure to prepare XII-45 is the same as that to prepare XII-27. XII-45, pale-yellow oil (0.33 g, 49%).

Example 115

3.15 Synthesis of (3S,4S)-tert-butyl 3-{{6-[benzyl(tert-butoxycarbonyl)amino]-4-methylpyridin-2-yl}methyl}-4-{2-[tert-butoxycarbonyl(3-fluorophenethyl)amino]ethoxy}pyrrolidine-1-carboxylate (XII-28), (3R,4R)-tert-butyl 3-{{6-[benzyl(tert-butoxycarbonyl)amino]-4-methylpyridin-2-yl}methyl}-4-{2-[tert-butoxycarbonyl(3-fluorophenethyl)amino]ethoxy}pyrrolidine-1-carboxylate (XII-34), (3S,4R)-tert-butyl 3-{{6-[benzyl(tert-butoxycarbonyl)amino]-4-methylpyridin-2-yl}methyl}-4-{2-[tert-butoxycarbonyl(3-fluorophenethyl)amino]ethoxy}pyrrolidine-1-carboxylate (XII-40), and (3R,4S)-tert-butyl 3-{{6-[benzyl(tert-butoxycarbonyl)amino]-4-methylpyridin-2-yl}methyl}-4-{2-[tert-butoxycarbonyl(3-fluorophenethyl)amino]ethoxy}pyrrolidine-1-carboxylate (XII-46)

A solution of di-tert-butyl dicarbonate (0.22 g, 0.001 mol) in $CH_2Cl_2$ (5 mL) was added dropwise to a solution of XII-27 (0.66 g, 0.001 mol) in $CH_2Cl_2$ (5 mL) and 1 M NaOH (3 mL). The reaction mixture was stirred at room temperature for 24 h. The organic layer was separated. The aqueous layer was extracted with $CH_2Cl_2$ (10 mL×2). The combined organic layers was washed with water (10 mL×2), and dried over $Na_2SO_4$. The solvent was evaporated in vacuo. The residue was purified by column chromatography (silica gel, hexanes:EtOAc=7.5:2.5) to afford a colorless oil (XII-28, 0.60 g, 78%).

The procedure to prepare XII-34 is the same as that to prepare XII-28. XII-34, colorless oil (0.57 g, 75%).

The procedure to prepare XII-40 is the same as that to prepare XII-28. XII-40, colorless oil (0.47 g, 62%).

The procedure to prepare XII-46 is the same as that to prepare XII-28. XII-46, colorless oil (0.57 g, 75%).

Example 116

Synthesis of (3S,4S)-tert-butyl 3-{2-[tert-butoxycarbonyl(3-fluorophenethyl)amino]ethoxy}-4-{[6-(tert-butoxycarbonylamino)-4-methylpyridin-2-yl]methyl}pyrrolidine-1-carboxylate (XII-29), (3R,4R)-tert-butyl 3-{2-[tert-butoxycarbonyl(3-fluorophenethyl)amino]ethoxy}-4-{[6-(tert-butoxycarbonylamino)-4-methylpyridin-2-yl]methyl}pyrrolidine-1-carboxylate (XII-35), (3R,4S)-tert-butyl 3-{2-[tert-butoxycarbonyl(3-fluorophenethyl)amino]ethoxy}-4-{[6-(tert-butoxycarbonylamino)-4-methylpyridin-2-yl]methyl}pyrrolidine-1-carboxylate (XII-41), and (3S,4R)-tert-butyl 3-{2-[tert-butoxycarbonyl(3-fluorophenethyl)amino]ethoxy}-4-{[6-(tert-butoxycarbonylamino)-4-methylpyridin-2-yl]methyl}pyrrolidine-1-carboxylate (XII-47)

A solution of XII-28 (0.38 g, 0.0005 mol) in EtOH (20 mL) was treated with 20% wt $Pd(OH)_2$ on carbon (150 mg). The reaction mixture was stirred at 60° C. under a hydrogen atmosphere for 36 h. The catalyst was filtered through Celite. The Celite pad was washed with EtOH (10 mL×2). The combined filtrates were concentrated in vacuo. The residue was diluted with $CH_2Cl_2$ (10 mL) and 1 M NaOH (10 mL). The organic layer was separated, and the aqueous layer was extracted with $CH_2Cl_2$ (10 mL×2). The combined organic layers were concentrated in vacuo. The residue was purified by column chromatography (silica gel, hexanes:EtOAc=7:3) to afford a colorless oil (XII-29, 0.29 g, 85%).

The procedure to prepare XII-35 is the same as that to prepare XII-29. XII-35, colorless oil (0.27 g, 80%).

The procedure to prepare XII-41 is the same as that to prepare XII-29. XII-41, colorless oil (0.048 g, 48%).

The procedure to prepare III-47 is the same as that to prepare III-29. III-47, colorless oil (0.59 g, 58%).

Example 117

Synthesis of 6-{{(3'S,4'S)-4'-[2"-(3"'-fluorophenethylamino)ethoxy]pyrrolidin-3'-yl}methyl}-4-methylpyridin-2-amine trihydrochloride (XII-30), 6-{{(3'R,4'R)-4'-[2"-(3"'-fluorophenethylamino)ethoxy]pyrrolidin-3'-yl}methyl}-4-methylpyridin-2-amine trihydrochloride (XII-36), 6-{{(3'S,4'R)-4'-[2"-(3"'-fluorophenethylamino) ethoxy]pyrrolidin-3'-yl}methyl}-4-methylpyridin-2-amine trihydrochloride (XII-42), 6-{{(3'R,4'S)-4'-[2"-(3"'-fluorophenethylamino) ethoxy]pyrrolidin-3'-yl}methyl}-4-methylpyridin-2-amine trihydrochloride (XII-48)

XII-29 (0.13 g, 0.0002 mol) was cooled in an ice-water bath under argon. A solution of 4 M HCl in 1,4-dioxane (4 mL) was then added slowly with stirring. The ice-water bath was removed after 3 h, and the reaction mixture was stirred at room temperature under an argon atmosphere for 34 h. The reaction mixture was concentrated in vacuo, and the residue was partitioned between water (10 mL) and ethyl acetate (10 mL). The aqueous layer was then washed with ethyl acetate (5 mL×2). After evaporation of water by high vacuum rotary evaporation, the residue was dried with a lyophilizer to afford a white solid (III-32, 0.11 g, quantitative yield). $[\alpha]^{25}$=+36.4° (c=1, MeOH)

The procedure to prepare XII-36 is the same as that to prepare XII-30. XII-36, white solid (0.11 g, quantitative yield). $[\alpha]^{25}$=−36.4° (c=1, MeOH)

The procedure to prepare III-42 is the same as that to prepare III-30. II-42, white solid (0.11 g, quantitative yield). $[\alpha]^{25}$=−33.6° (c=1, MeOH)

The procedure to prepare III-48 is the same as that to prepare III-30. III-48, white solid (0.11 g, quantitative yield). $[\alpha]^{25}$=+33.6° (c=1, MeOH)

Example 118

In accordance with the preceding, various other compounds can be prepared in an analogous fashion using comparable synthetic techniques or straightforward modifications thereof, as would be understood by those skilled in the art. For instance, compounds having substructure I comprising a thiazine (X=S, m=n=1), oxazine (X=O, m=n=1), pyrazine (X=N, m=n=1), thiazole (X=S, m=1 and n=0, or m=0, and n=1), oxazole (X=O, m=1 and n=0 or m=0 and n=1), imidazole (X=N, m=1 and n=0, or m=0 and n=1), pyrrole (X=CH, m=1 and n=0, or m=0 and n=1), pyrimidine (X=N, m=2 and n=0, or m=0 and n=2) moiety can be prepared from the appropriate starting material using synthetic procedures similar to those described in Schemes 1'-VI'. Likewise, compounds having substructure II comprising a cyclohexane (Y=CH, p=1 and q=2 or p=2 and q=1) or piperidine (Y=N, p=1 and q=2 or p=2 and q=1) moiety can be obtained using a suitable starting material. As would also be understood, any $R_2$ moiety of substructure III (Z=O or NH) can be introduced, limited only by the corresponding amine availability and its reactivity under the reductive amination conditions employed.

With regard to variation of substructure III, consider compounds in accordance with this invention, where $R_3$ can be a linear or cyclic aminoalkyl moiety. In particular, with reference to the compounds of this example, such moieties can comprise a phenethyl cyclopentane group (X=H), or a substituted phenethyl cyclopentane variation thereof (e.g., X=F, Cl, and/or $CF_3$ at any of the para, meta or ortho positions), or a benzyl-pyrrolidin-3-yl group, or a substituted benzyl-pyrrolidin-3-yl variation thereof (e.g., X=F, Cl, and/or $CF_3$ at any of the para, meta or ortho positions). Such compounds are prepared using an appropriate amine reagent for reductive amination of the corresponding oxopyrrolidinyl intermediate, in turn available via ring-opening reaction of lithiated 2-amino-4,6-dimethylpyridine with pyrroline epoxide, as demonstrated elsewhere herein.

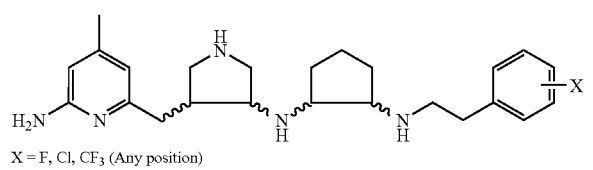

X = F, Cl, $CF_3$ (Any position)

N-[4-(6-Amino-4-methyl-pyridin-2-ylmethyl)-pyrrolidin-3-yl]-N'-substituted phenethyl-cyclopentane-1,2-diamine

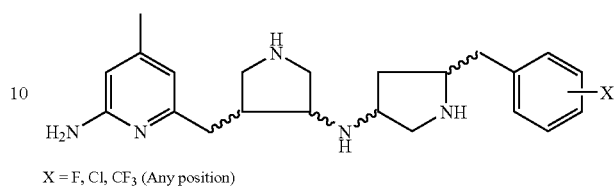

X = F, Cl, $CF_3$ (Any position)

6-[4-(5-Substituted benzyl-pyrrolidin-3-ylamino)-pyrrolidin-3-ylmethyl]-4-methyl-pyridin-2-ylamine Examples 119-122 can be considered in conjunction with Scheme XVI' below. The phenyl groups of compounds in Scheme XVI' can be, alternatively, substituted at any of the para, meta or ortho positions with substituents including but not limited to halogen, alkyl or halogenated alkyl group.

Scheme XVI' a.

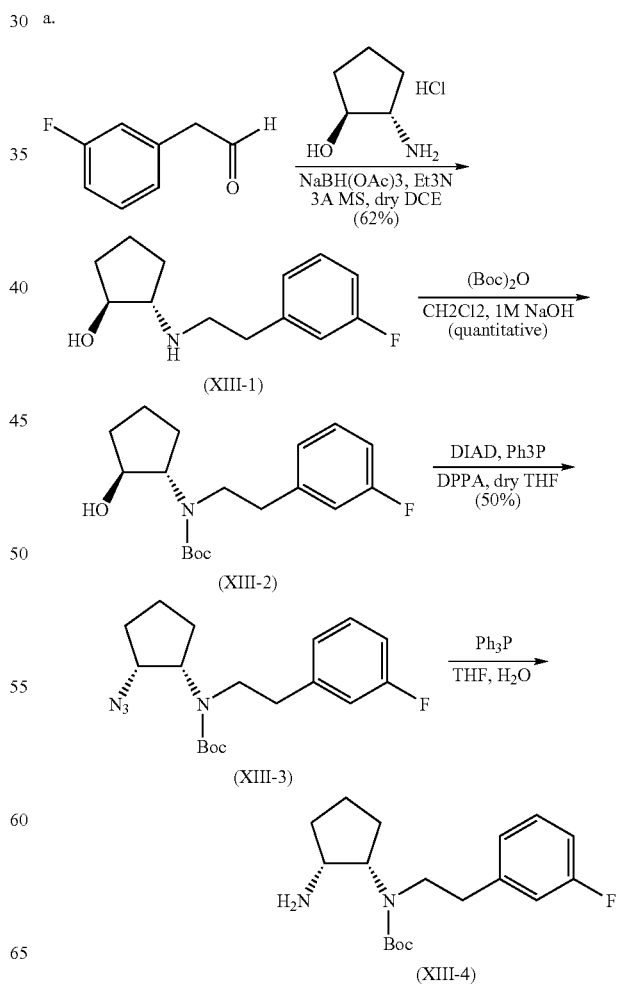

b.

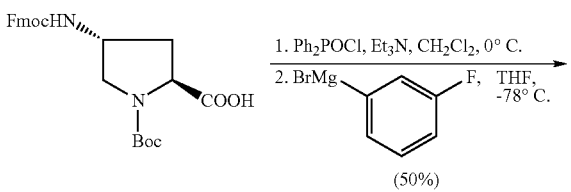

(50%)

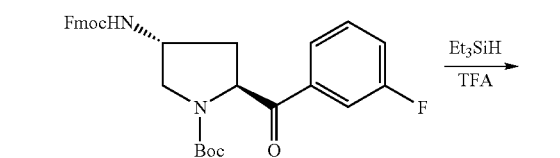

(XIII-5)

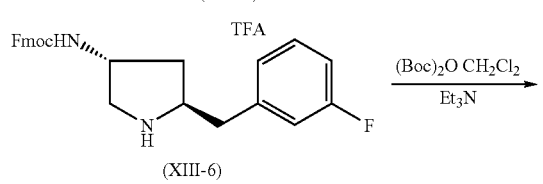

(XIII-6)

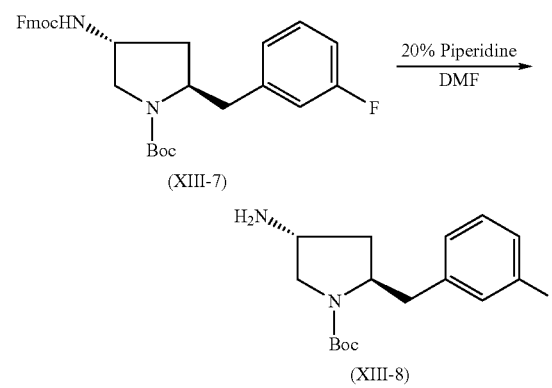

(XIII-7)

(XIII-8)

c.

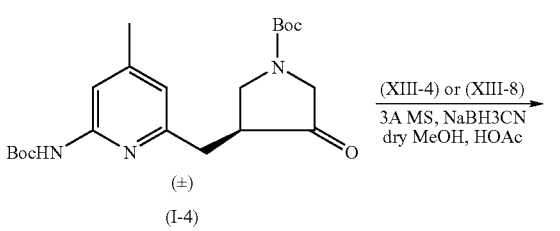

(±)
(I-4)

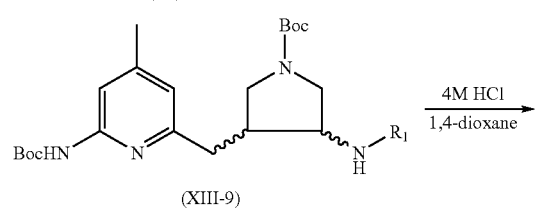

(XIII-9)

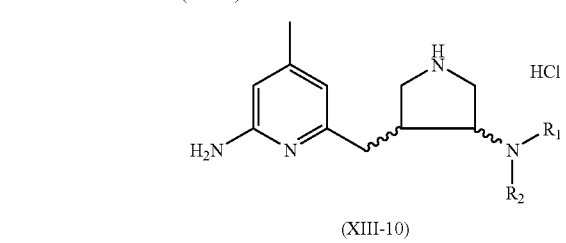

(XIII-10)

Example 119

Synthesis of (1S,2S)-2-(3-fluorophenethylamino)cyclopentanol (XIII-1)

trans-(1S,2S)-2-Aminocyclopentanol hydrochloride (1.51 g, 0.011 mol) and triethylamine ($Et_3N$, 1.32 g, 1.81 g, 0.013 mol), 3 Å molecular sieves (3 g) were dissolved in dry DCE (30 mL). The mixture was stirred at room temperature under a $N_2$ atmosphere for 10 min. $NaBH(OAc)_3$ (2.76 g, 0.013 mol) and I-4 (1.38 g, 0.01 mol) was then added, and the react ion mixture was stirred at room temperature under a $N_2$ atmosphere overnight. NaOH (1 M, 20 mL) was then added, and the organic layer was separated. The aqueous layer was extracted with $CH_2Cl_2$ (20 mL×2). The combined organic layers were washed with 1 M NaOH (20 mL) and $H_2O$ (20 mL), and then dried over $Na_2SO_4$. The solvent was concentrated in vacuo. The residue was purified by column chromatography (silica gel, $CH_2Cl_2$:MeOH=9.5:0.5) to afford a pale-yellow oil (1.38 g, 62%)

Example 120

The synthetic procedure of tert-butyl 3-fluorophenethyl [(1S,2S)-2-hydroxycyclopentyl]carbamate is the same as that of II-2 (quantitative yield).

Example 121

The synthetic procedure of tert-butyl (1S,2R)-2-aminocyclopentyl(3-fluorophenethyl)carbamate is the same as that of II-3.

Example 122

Synthesis of (2S,4R)-tert-butyl 4-{[(9H-fluoren-9-yl)methoxy]carbonylamino}-2-(3-fluorobenzoyl)pyrrolidine-1-carboxylate (XIII-5).

N-Boc-trans-4-N-Fmoc-amino-L-proline (0.24 g, 0.19 mL, 0.001 mol) in $CH_2Cl_2$ (10 mL) was treated with diphenylphosphinic chloride (0.001 mol) at 0° C. in the presence of $Et_3N$ (0.10 g, 0.14 mL, 0.001 mol) for 2 h. EtOAc (10 mL) was then added to the mixture, which was then washed successively with $H_2O$ (5 mL), saturated $NaHCO_3$ aqueous solution (5 mL), and brine (5 mL), and dried over $Na_2SO_4$. The organic layer was concentrated in vacuo, and the resulting residue was dissolved in THF (10 mL). The solution was then cooled to −78° C. 3-Fluorophenylmagnesium bromide solution (1.0 M in THF, 1 mL, 0.001 mol) was added, and the mixture was gradually warmed to room temperature before being poured into a mixture of 0.1 M phosphate buffer (pH=7.2, 5 mL) and 1 M HCl aqueous solution (5 mL) at 0° C. The aqueous layer was extracted with $CH_2Cl_2$ (10 mL×3). The combined organic layers were washed successively with saturated aqueous $NaHCO_3$ (10 mL) and brine (10 mL) and dried over $Na_2SO_4$. The solvent was evaporated in vacuo, and the residue was purified by column chromatography (silica gel, hexanes:EtOAc=7:3) to afford a white solid (XIII-5, 0.27 g, 50%).

Example 123

Enzyme inhibitory assay. All of the NOS isoforms used are recombinant enzymes overexpressed in *E. coli* from different sources. The murine macrophage iNOS was expressed and purified according to the following procedure: (Hevel, J. M.; White, K. A.; Marletta, M. A. Purification of the Inducible Murine Macrophage Nitric Oxide Synthase. J. Biol. Chem. 1991, 266, 22789-22791.)

iNOS expression: An overnight culture of pCWiNOS was used to inoculate (1:100) larger cultures of Terrific Broth media (12 g/L tryptone, 24 g/L yeast extract, 4 mL/L glycerol, 17 mM $KH_2PO_4$, and 72 mM $K_2HPO_4$) containing 50 µg/mL ampicillin and 34 µg/mL chloramphenicol at 37° C. At an $OD_{600}$ of ~0.5, the culture was cooled to 25° C. and induced by the addition of 1 mM IPTG (final concentration). After approximately 24 h of growth at 25° C., the cells were pelleted at 5300×g, transferred to 50 mL conical tubes, and stored at −80° C.

iNOS purification: Cell pellets from 1.0 L of culture were resuspended in sonication buffer (50 mM Hepes, pH 7.4, 10% glycerol, 10 µg/mL benzamidine, 5 µg/mL leupeptin, 0.2 mM of PMSF, and 1 µg/mL each of pepstatin, chymostatin, and antipain) and lysed by sonication. Centrifugation for 20 min at 13000×g yielded supernatant which contained iNOS active enzyme. iNOS supernatant was loaded onto 1 g of a 2',5'-ADP-Sepharose 4B resin column. The column was then washed with 20 ml iNOS purification buffer (10 mM $K_2HPO_4$, 10% glycerol, 0.5 mM L-arginine, pH 7.4) and 10 µM $BH_4$. Inducible NOS was eluted with 30 ml iNOS purification buffer supplemented with 10 mM 2'(3')-AMP, 10 µM $BH_4$, and 0.3 M NaCl. The eluent was concentrated to 5 ml by ultrafiltration. The above concentration operation was repeated three times more with 10 ml Hepes buffer supplemented with 10 µM $BH_4$, to give purified inducible NOS.

Rat nNOS was expressed according to the procedure of Roman et al. (Roman, L. J.; Sheta, E. A.; Martasek, P.; Gross, S. S.; Liu, Q.; Masters, B. S. S. High-Level Expression of Functional Rat Neuronal Nitric Oxide Synthase in *Escherichia coli*. Proc. Natl. Acad. Sci. U.S.A. 1995, 92, 8428-8432.)

nNOS expression: An overnight culture of pCWnNOS was used to inoculate (1:100) larger cultures of Terrific Broth media (10 g/L tryptone, 20 g/L yeast extract, 4 ml/L glycerol, 19.5 mM $KH_2PO_4$, 30.5 mM $Na_2HPO_4$) containing 50 µg/mL ampicillin and 34 µg/mL chloramphenicol at 37° C. At an $OD_{600}$ of ~1.0, the culture was cooled 25° C. and induced by the addition of 0.5 mM IPTG, 450 µM d-aminolevulinic acid, 1 mM ATP, 3 µM riboflavin. After approximately 48 h of post-induction incubation in the dark at 25° C. the cells were pelleted at 5300×g, transferred to 50 mL conical tubes, and stored at −80° C.

The nNOS was purified according to the procedure of Gerber et al. (Gerber, N. C.; Montellano, P. R. Neuronal Nitric Oxide Synthase: Expression in *Escherichia coli*, Irreversible Inhibition by Phenyldiazene, and Active Site Topology. J. Biol. Chem. 1995, 270, 17791-17796).

nNOS purification: Cell pellets from 2.0 L of culture were resuspended in sonication Buffer A (50 mM Tris Base Buffer, pH 8.0, 10% glycerol), 2 mg/ml lysozyme. 0.5 mM L-arginine. 1 mM EDTA, 0.1 mM PMSF, 1 µg/ml antipain, and 1 µM each of leupeptin, pepstatin, and pepstatin) and lysed by sonication. Centrifugation for 1 h at 100000×g yielded supernatant which contained nNOS active enzyme. The supernatant was brought to 2 mM $CaCl_2$ and the protein was loaded onto a 15 ml calmodulin-Sepharose column equilibrated with Buffer A containing 2 mM $CaCl_2$. The column was washed with 100 ml Buffer B (50 mM Hepes, 5 mM DTT, and 10% DTT) containing 2 mM $CaCl_2$, 0.5 mM L-arginine, and 10 µM $BH_4$, and eluted with 30 ml Buffer B supplemented with 0.3 M NaCl, 5 mM EGTA, 0.5 mM L-arginine, and 10 µM $BH_4$. The protein was then loaded onto a 5 ml 2',5'-ADP-Sepharose column equilibrated with Buffer B supplemented with 0.3 M NaCl, 0.5 mM L-arginine, and 10 µM $BH_4$. The column was washed with 25 ml Buffer B containing 0.5 mM L-arginine and 10 µM $BH_4$, and then 25 ml of Buffer B only supplemented with 10 µM $BH_4$ (without L-arginine). Neuronal NOS was eluted with 20 ml Buffer B supplemented with 10 mM 2'(3')-AMP, 10 µM $BH_4$ and 0.3 M NaCl. The 20 ml eluent was then concentrated to 5 ml by ultrafiltration. The above concentration operation was repeated twice more with 10 ml Buffer B supplemented with 10 µM $BH_4$ to give the purified neuronal NOS.

Bovine eNOS was expressed and isolated by Martasek et al. (Martasek, P.; Liu, Q.; Roman, L. J.; Gross, S. S.; Sessa, W. C.; Masters, B. S. S. Characterization of Bovine Endothelial Nitric Oxide Synthase Expressed in *Escherichia coli*. Biochem. Biophys. Res. Commun. 1996, 219, 359-365). The procedure is below:

Expression of bovine eNOS: An overnight culture of BoveNOSpCW was used to inoculate 0.5 liter (in a 2.8-liter Fernbach flask) of modified TB (20 g of yeast extract, 10 g of bacto-tryptone, 2.65 g of $KH_2PO_4$, 4.33 g of $Na_2HPO_4$ and 4 ml of glycerol per liter) containing ampicillin (50 mg/ml) and chloramphenicol (35 mg/ml). The cultures were grown to an OD600 of z0.8 at 22° C. (200 rpm) and induced with 0.5 mM IPTG. One hour before IPTG induction, d-aminolevulinic acid (0.5 mM final) was added and, at the time of IPTG induction, riboflavin (3 mM final) and ATP (1 mM final) were also added. After induction, the flasks were kept in the dark at 22° C. (200 rpm). The cells were harvested 48 h after induction, and the cell pellet was frozen at −80° C. until purification was carried out.

Purification of bovine eNOS. The purification was typically carried out with eNOS from 2 liters of *E. coli* culture. The eNOS protein was purified using a modification of the published protocol for nNOS (14). The cells were resuspended in buffer C [50 mM Tris-Cl, pH 7.8, 1 mM EDTA, 1 mM DTT, 10% glycerol (v/v), 150 mM NaCl, 0.1 mM phenylmethylsulfonyl fluoride, 1 mM leupeptin and 1 mM pepstatin], lysed by pulsed sonication and then centrifuged to sediment the cell debris. The supernatant was applied to a 2',5'-ADP Sepharose 4B column equilibrated in buffer D [50 mM Tris-Cl, pH 7.8, 0.1 mM EDTA, 0.1 mM dithiothreitol, 150 mM NaCl, 10% glycerol (v/v)]. The column was washed with 20 column volumes of buffer B and again with 20 column volumes of buffer B containing 600 mM NaCl. Finally, protein was eluted with buffer B containing 600 mM NaCl and 5 mM 2'-AMP. The fractions were screened for absorption in the Soret region ($A_{400}$) and hemoprotein-containing fractions were pooled and concentrated (Centriprep 50, Amicon). Repeated dilution/concentration [50 mM Tris-Cl, pH 7.8, 0.1 mM EDTA, 0.1 mM dithiothreitol, 10% glycerol (vol/vol)] was used to reach a final concentration of 150 mM NaCl and commensurately reduce the 2'-AMP content. If harvested 24 h after IPTG induction, only a 47% yield was obtained relative to that after 48 h of IPTG treatment. The cytosolic extracts contained 6-10 mg of eNOS per liter, as determined by CO-difference spectra, and the 2',5'-ADP Sepharose 4B column pool yielded 3.6-6.0 mg (>>60% recovery). The purified eNOS is stored in the presence of 1 mM L-arginine.

eNOS washing: eNOS contains a significant amount of L-arginine, which will interfere with the enzyme assay. The L-arginine can be removed by several dilution and concentration steps using an Amico concentrator. The dilution buffer is 10 ml Tris-HCl 50 mM containing 0.1 mM EDTA, 400 mM NaCl, 10% glycerol and 1 mM beta-mercaptoethanol. The above dilution and concentration operation was repeated three times to give purified eNOS.

Nitric oxide formation from NOS was monitored by the hemoglobin capture assay as described previously. (Hevel, J. M.; Marletta, M. A. Nitric Oxide Synthase Assays. Methods Enzymol. 1994, 133, 250-258).

Procedure for iNOS: Into a disposable cuvette (1.5 ml) was added 10 µL of 0.6 mM L-arginine (the final concentration is 10 µM), 6 µL of inhibitor, 10 µL of 6.24 mM NADPH, 6 µL of 12.5 g/L hemoglobin-A0 (ferrous form), 6 µl of 1 mM $BH_4$, 556 µL of 100 mM Hepes buffer, 6 µL of iNOS, and the time-dependent increase in the 401 nm absorbance was monitored at 30° C.

Procedure for nNOS and eNOS: Into a disposable cuvette (1.5 ml) was added 10 µL of 0.6 mM L-arginine (the final concentration is 10 µM), 6 µL of inhibitor, 10 µL of 50 mM $CaCl_2$, 10 µL of 40,000 units/mL calmodulin, 10 µL of 6.24 mM NADPH, 6 µL of 12.5 g/L hemoglobin-A0 (ferrous form), 6 µl of 1 mM $BH_4$, 536 µL of 100 mM Hepes buffer, 6 µL of nNOS or eNOS, and the time-dependent increase in the 401 nm absorbance was monitored at 30° C. The $IC_{50}$ values were obtained by measuring the percentage of inhibition in the presence of 10 µM L-arginine with at least five concentrations of inhibitor. The apparent Ki values were calculated according to the following inhibition equation: % inhibition=100[I]/{[I]+Ki(1+[S]/Km)} (Segel, I. H. Enzyme Kinetics; John Wiley and Sons: New York, 1975; p 105). The parameters of Km values for L-arginine were 1.3 µM (nNOS), 8.3 µM (iNOS), and 1.7 µM (eNOS). The selectivity of an inhibitor is defined as the ratio of the respective Ki values. The data of Tables 1a-b show that the compounds of this invention potently inhibit NOS activity, and selectively inhibit nNOS over other enzyme isoforms.

TABLE 1a

The NOS enzyme assay results

| | $IC_{50}$(µM) | | | calc. Ki(µM) | | | Selectivity** | |
|---|---|---|---|---|---|---|---|---|
| | nNOS[a] | iNOS[b] | eNOS[c] | nNOS | iNOS | eNOS | n/i | n/e |
| P-1 | 682.33 | 2026.6 | | 78.5 | 919.16 | | 11.71 | |
| P-2 | 121.55 | 132.45 | | 13.98 | 60.07 | | 4.3 | |
| P-3 | 1654.48 | 3857.3 | | 190.34 | 1749.5 | | 9.19 | |
| P-4 | 416.75 | 1343.7 | | 47.94 | 609.43 | | 12.71 | |
| P-5 | 2650.77 | 5562.4 | | 304.96 | 2522.81 | | 8.27 | |
| P-6 | 108.17 | 230.71 | | 12.44 | 104.64 | | 8.41 | |
| P-7 | 34.61 | 965.19 | | 3.98 | 437.76 | | 109.99 | |
| P-8 | 117.1 | 1437.2 | | 13.47 | 651.85 | | 48.39 | |
| P-9 | 248.98 | 649.38 | | 28.64 | 294.53 | | 10.28 | |
| P-10 | 724.04 | 2756.9 | | 83.3 | 1250.38 | | 15.01 | |
| P-11 | 60.32 | 56 | 2345.69 | 6.94 | 25.24 | 340.83 | 3.64 | 49.11 |
| P-12 | 115.47 | 317.07 | 586.35 | 13.28 | 143.81 | 85.20 | 10.83 | 6.42 |
| P-13 | 248.08 | 515.43 | 4705.49 | 28.54 | 233.77 | 683.70 | 8.19 | 23.96 |
| P-14 | 76.17 | 170.64 | 5961.51 | 8.76 | 77.39 | 866.20 | 8.83 | 98.88 |
| P-15 | 136.29 | 679.28 | 1663.47 | 15.68 | 308.09 | 241.7 | 19.65 | 15.41 |
| P-16 | 120.46 | 658.24 | >10,000* | 13.86 | 298.55 | >1,453 | 21.54 | >104.83 |
| P-17 | 178.79 | 918.56 | >10,000* | 20.57 | 416.61 | >1,453 | 20.25 | >70.64 |
| P-18 | 125.62 | 366.23 | >70,000* | 14.45 | 166.1 | >10.171 | 11.49 | >703.88 |
| P-19 | 181.9 | 558.76 | 3167.01 | 20.93 | 253.43 | 460.16 | 12.11 | 22.00 |
| P-20 | 111.66 | 516.05 | 4304.36 | 12.85 | 234.06 | 625.42 | 18.21 | 48.67 |
| P-21 | 212.14 | 629.56 | 1173.58 | 24.4 | 285.54 | 170.52 | 11.70 | 6.99 |
| P-22 | 155.74 | 460.84 | 748.02 | 17.92 | 209.01 | 108.69 | 11.66 | 6.07 |
| P-23 | 96.91 | 228.65 | | 11.15 | 103.7 | | 9.30 | |
| P-24 | 125.67 | 674.16 | | 14.46 | 305.77 | | 21.15 | |
| P-25 | 21.25 | 40.79 | | 2.44 | 18.5 | | 7.58 | |
| P-26 | 107.06 | 375.32 | | 12.32 | 170.23 | | 13.82 | |
| P-27 | 27.54 | 366.41 | 608.88 | 3.17 | 166.19 | 88.47 | 52.43 | 27.9 |
| P-28 | 82.07 | 315.45 | 2522.94 | 9.44 | 143.07 | 366.58 | 15.16 | 38.8 |
| P-29 | 3.38 | 128.76 | 2990.05 | 0.39 | 58.40 | 434.45 | 150.0 | 1114.0 |
| P-30 | 28.97 | 429.14 | 962.96 | 3.33 | 194.64 | 139.92 | 58.45 | 42.02 |
| P-31 | 21.04 | 524.33 | >10,000* | 2.42 | 237.81 | >1,453 | 98.27 | >600 |
| P-32 | 19.98 | 654.63 | >10,000* | 2.3 | 296.9 | >1,453 | 129.09 | >632 |
| P-33 | 10.22 | 354.75 | >70,000* | 1.18 | 160.9 | >10,171 | 136.36 | >8619.5 |
| P-34 | 10.95 | 383.54 | 1669.65 | 1.26 | 173.95 | 242.6 | 138.06 | 192.54 |
| P-35 | 11.79 | 440.03 | 2918.87 | 1.36 | 199.58 | 424.11 | 146.75 | 311.85 |
| P-36 | 29 | 488.92 | 740.14 | 3.34 | 221.75 | 107.54 | 66.39 | 32.20 |
| P-37 | 653.63 | 505.85 | 1253.43 | 75.2 | 229.43 | 182.12 | 3.05 | 2.42 |
| P-38 | 23.84 | 936.7 | 1248.2 | 2.74 | 424.84 | 181.36 | 155.05 | 66.19 |
| P-39 | 196.15 | 716.41 | 638.41 | 22.6 | 324.93 | 92.76 | 14.38 | 4.10 |
| P-40 | 29.94 | 181.65 | | 3.44 | 82.39 | | 23.95 | |
| P-41 | 49.19 | 58.3 | | 5.66 | 26.44 | | 4.67 | |
| P-42 | 19.03 | 154.38 | | 2.19 | 70.02 | | 31.97 | |
| P-43 | 39.51 | 92.52 | | 4.55 | 41.96 | | 9.22 | |
| P-44 | 21.46 | 114.5 | | 2.47 | 51.93 | | 21.02 | |
| P-45 | 40.09 | 157.68 | | 4.61 | 71.52 | | 15.51 | |
| P-46 | 0.83 | 12.11 | 1609.82 | 0.095 | 5.5 | 233.91 | 58 | 2462.2 |
| P-47 | 5.34 | 70.62 | 1808.28 | 0.61 | 32.03 | 262.74 | 52.5 | 430.7 |

[a]rat nNOS;
[b]murine iNOS;
[c]bovine eNOS;
*Indicates no inhibition was observed up to the concentration listed;
**where n/i is Ki(iNOS)/Ki(nNOS) and n/e is Ki(eNOS)/Ki(nNOS).

a: rat nNOS; b: murine iNOS; c: bovine eNOS; *Indicates no inhibition was observed up to the concentration listed; ** Where n/i is Ki(iNOS)/Ki(nNOS) and n/e is Ki(eNOS)/Ki (nNOS).

TABLE 1b nNOS enzyme inhibition, con't.

| Compounds[a] | $K_i$(uM) | | | Selectivity | |
|---|---|---|---|---|---|
| | nNOS | iNOS | eNOS | n/i | n/e |
| P-48 | 0.085 | 8.95 | 85.16 | 105.6 | 1004.2 |
| P-49 | 0.104 | 9.48 | 83.19 | 91.1 | 800 |
| P-50 | 0.197 | 14.09 | 84.39 | 71.5 | 428.4 |
| P-51 | 0.144 | 7.97 | 130.24 | 55.4 | 904.5 |
| P-52 | 0.206 | 13.55 | 116.11 | 65.8 | 563.6 |
| P-53 | 0.159 | 9.01 | 71.63 | 56.7 | 450.5 |
| P-54 | 0.53 | 44.85 | 118.34 | 84.4 | 222.7 |
| P-55 | 0.25 | 44.11 | 95.18 | 178.6 | 385.3 |
| P-56 | 0.74 | 40.42 | 61.19 | 54.6 | 82.7 |
| P-57 | 0.87 | 27.35 | 78.75 | 31.3 | 90.1 |
| P-58 | 0.74 | 58.72 | 108.55 | 79 | 146.1 |
| P-59 | 0.66 | 83.9 | 201.61 | 127.1 | 305.5 |
| P-60 | 0.157 | 3.56 | 40.81 | 22.6 | 260 |
| P-61 | 0.110 | 7.7 | 29.91 | 70 | 272 |
| P-62 | 0.024 | 5.4 | 78.45 | 222 | 3228.4 |
| P-63 | 0.136 | 12.20 | 40.04 | 90 | 294.4 |
| P-64 | 0.393 | 22.79 | 125.19 | 58 | 319 |
| P-65 | 0.414 | 23.76 | 63.22 | 57.4 | 153 |
| P-66 | 0.483 | 44.23 | 76.13 | 91.6 | 158 |
| P-67 | 0.088 | 18.17 | 123.90 | 206.5 | 1408 |
| P-68 | 0.589 | 20.46 | 16.47 | 34.7 | 28 |
| P-69 | 1.891 | 75.36 | 58.14 | 40 | 31 |
| P-70 | 0.027 | 4.597 | 17.716 | 170.3 | 656.2 |
| P-71 | 0.014 | 4.064 | 27.949 | 290.3 | 1996.4 |
| P-72 | 0.119 | 22.593 | 44.094 | 189.9 | 370.5 |
| P-73 | 0.048 | 26.586 | 49.069 | 553.9 | 1022.3 |
| P-74 | 1.214 | 56.638 | 48.873 | 46.7 | 40.27 |
| P-75 | 0.326 | 38.235 | 92.433 | 117.3 | 283.5 |
| P-76 | 0.015 | 2.4 | 25 | 160 | 1700 |
| P-77 | 0.053 | 1.4 | 26 | 26.4 | 500 |
| P-78 | 0.4 | 1.4 | 20 | 3.5 | 50 |
| P-79 | 2.3 | 13 | 125 | 5.7 | 54.3 |
| P-80 | 5 | 19 | 85 | 3.8 | 17 |
| P-81 | 5 | 8.5 | 1.5 | 1.7 | 0.3 |
| P-82 | 1.7 | 3.4 | 3 | 2 | 1.8 |
| P-83 | 0.049 | 3.6 | 24.6 | 74 | 505 |
| P-84 | 0.005 | 3.7 | 19.0 | 734 | 3788 |
| P-85 | 0.0177 | 15 | 53.4 | 852 | 3020 |
| P-86 | 0.160 | 25 | 32.3 | 155 | 202 |
| P-87 | 0.116 | 7.5 | 26.2 | 64 | 225 |
| P-88 | 0.0072 | 5.8 | 19.2 | 807 | 2676 |
| P-89 | 0.063 | 18.71 | 36.19 | 296 | 573 |
| P-90 | 0.1935 | 18.06 | 18.78 | 93 | 97 |

[a]Structures were shown above

We claim:
1. A neuronal nitric oxide synthase inhibitor compound of a formula

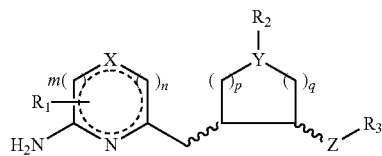

wherein X is selected from CR, N, O and S, and R is selected from H, methyl and substituted methyl moieties; m and n are integers independently selected from 0, 1 and 2, and 0<(m +n)≦2, and said heterocyclic ring is aromatic; $R_1$ is selected from H, alkyl, substituted alkyl and halogen moieties; Y is selected from CH, O, N and $^+NR_4$; p and q are integers independently selected from 0, 1 and 2, and 1<(p +q)≦4; Z is selected from NH, O and NHC(O); $R_2$ is selected from H, alkyl, amino, hydroxyl, and substituted alkyl moieties; $R_3$ is selected from alkyl, substituted alkyl, hydroxyalkyl, substituted hydroxyalkyl, arylalkylaminoalkyl, substituted arylalkylaminoalkyl, arylalkyloxaalkyl substituted arylalkyloxaalkyl, arylalkylamidoalkyl, substituted arylalkylamidoalkyl, aminoalkyl, and substituted aminoalkyl moieties; $R_4$ is H; and cis and trans stereoisomers and salts thereof.

2. The compound of claim 1 wherein X is CR when (m+n) =2, and X is S when (m+n)=1.

3. The compound of claim 2 wherein Y is $^+NR_4$, and p and q are 1.

4. The compound of claim 3 wherein Z is selected from NH and O, and $R_3$ comprises a an aminoalkyl or substituted aminoalkyl moiety.

5. The compound of claim 4 wherein said $R_3$ moiety is selected from primary, secondary, tertiary, linear and cyclic amino groups and combinations thereof.

6. The compound of claim 5 wherein $R_2$ is selected from H and aminoalkyl moieties.

7. The compound of claim 1 wherein R is methyl.

8. The compound of claim 7 wherein Y is $^+NR_4$.

9. The compound of claim 8 wherein Z is NH or O, $R_2$ is selected from H, aminoalkyl and substituted aminoalkyl moieties, and $R_3$ is selected from aminoalkyl, substituted aminoalkyl, arylalkylaminoalkyl and substituted arylalkylaminoalkyl moieties.

10. The compound of claim 2 wherein Y is CH, and p and q are 1.

11. The compound of claim 10 wherein Z is selected from NH and O, $R_2$ is selected from H, aminoalkyl and substituted aminoalkyl moieties, and $R_3$ is selected from aminoalkyl, substituted aminoalkyl, arylalkylaminoalkyl and substituted arylalkylaminoalkyl moieties.

12. A neuronal nitric oxide synthase inhibitor compound of a formula

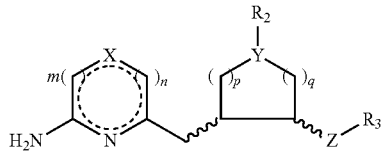

wherein X is $CR_1$ and $R_1$ is selected from H, methyl, and substituted methyl moieties; m and n are integers independently selected from 0, 1 and 2, and 0<(m +n)≦2; Y is selected from CH, N and $^+NR_4$; p and q are integers independently selected from 1 and 2; $R_2$ is selected from H, alkyl, substituted alkyl, aminoalkyl, substituted aminoalkyl, hydroxyalkyl, and substituted hydroxyalkyl moieties; Z is selected from NH, O and NHC(O); $R_3$ is selected from alkyl, substituted alkyl, hydroxyalkyl, substituted hydroxyalkyl, aminoalkyl, substituted aminoalkyl, arylalkylaminoalkyl and substituted arylalkylaminoalkyl moieties; $R_4$ is H; and cis and trans stereoisomers and salts thereof.

13. The compound of claim 12 wherein $R_1$ is selected from methyl and substituted methyl moieties, and m and n are 1.

14. The compound of claim 12 wherein $R_2$ is H.

15. The compound of claim 14 wherein Z is selected from NH and O, and $R_3$ is selected from phenylethylaminoalkyl and substituted phenylethylaminoalkyl moieties.

16. The compound of claim 15 wherein $R_1$ is selected from H and methyl moieties.

17. A neuronal nitric oxide synthase inhibitor compound of a formula

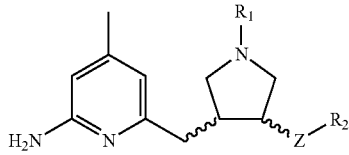

wherein $R_1$ is selected from H, alkyl, substituted alkyl, aminoalkyl, substituted aminoalkyl, hydroxyalkyl, and substituted hydroxyalkyl moieties; Z is selected from NH, O and NHC(O); and $R_2$ is selected from alkyl, substituted alkyl, hydroxyalkyl, substituted hydroxyalkyl, aminoalkyl, substituted aminoalkyl moieties arylalkylaminoalkyl and substituted arylalkylaminoalkyl; and cis and trans stereoisomers and salts thereof.

18. The compound of claim 17 wherein $R_1$ is H.

19. The compound of claim 18 wherein $R_2$ is selected from arylalkylaminoalkyl and substituted arylalkylaminoalkyl moieties.

20. The compound of claim 19 wherein Z is selected from NH and O.

* * * * *

UNITED STATES PATENT AND TRADEMARK OFFICE
CERTIFICATE OF CORRECTION

PATENT NO.        : 7,994,326 B2                                    Page 1 of 1
APPLICATION NO.   : 11/906283
DATED             : August 9, 2011
INVENTOR(S)       : Silverman et al.

It is certified that error appears in the above-identified patent and that said Letters Patent is hereby corrected as shown below:

In the specification:

Column 1, lines 12-14:
"The United States Government has certain rights to this invention pursuant to grant No. GM049725 from the National Institutes of Health to Northwestern University." should read --This invention was made with government support under grant number GM049725 awarded by the National Institutes of Health. The government has certain rights in the invention.--

Column 58, line 36:
"Cl2Cl2 (3 mL) was added" should read --CH2Cl2 (3 mL) was added--

Signed and Sealed this
Fifteenth Day of November, 2011

David J. Kappos
*Director of the United States Patent and Trademark Office*